(12) United States Patent
Malamas et al.

(10) Patent No.: US 7,482,349 B2
(45) Date of Patent: Jan. 27, 2009

(54) AMINO-5,5-DIPHENYLIMIDAZOLONE DERIVATIVES FOR THE INHIBITION OF β-SECRETASE

(75) Inventors: Michael S. Malamas, Jamison, PA (US); James J. Erdei, Philadelphia, PA (US); Iwan S. Gunawan, Somerset, NJ (US); Ping Zhou, Plainsboro, NJ (US); Yinfa Yan, Bedminster, NJ (US); Dominic A. Quagliato, Bridgewater, NJ (US)

(73) Assignee: Wyeth, Madison, NJ (US)

( * ) Notice: Subject to any disclaimer, the term of this patent is extended or adjusted under 35 U.S.C. 154(b) by 576 days.

(21) Appl. No.: 11/153,633

(22) Filed: Jun. 15, 2005

(65) Prior Publication Data

US 2005/0282825 A1 Dec. 22, 2005

Related U.S. Application Data

(60) Provisional application No. 60/580,286, filed on Jun. 16, 2004.

(51) Int. Cl.
C07D 401/10 (2006.01)
C07D 403/10 (2006.01)
C07D 405/14 (2006.01)
A61K 31/4178 (2006.01)

(52) U.S. Cl. .......... 514/255.05; 514/256; 514/341; 514/397; 544/224; 544/335; 544/336; 546/274.4; 548/312.4

(58) Field of Classification Search ............ 544/224, 544/335, 336; 546/274.4; 548/312.4; 514/255.05, 514/256, 341, 397
See application file for complete search history.

(56) References Cited

U.S. PATENT DOCUMENTS

| | | | |
|---|---|---|---|
| 4,140,793 | A | 2/1979 | Ward |
| 4,225,613 | A | 9/1980 | Ward |
| 6,054,457 | A | 4/2000 | Setoi et al. |
| 6,399,824 | B1 | 6/2002 | Hofmeister et al. |
| 6,656,957 | B1 | 12/2003 | Allgeier et al. |
| 6,689,804 | B2 | 2/2004 | Wu et al. |
| 6,974,829 | B2 | 12/2005 | Tung et al. |
| 7,285,682 | B2 | 10/2007 | Hu |
| 2005/0282826 | A1 | 12/2005 | Malamas et al. |
| 2006/0111370 | A1 | 5/2006 | Zhu et al. |
| 2006/0160828 | A1 | 7/2006 | Malamas et al. |
| 2006/0173049 | A1 | 8/2006 | Malamas et al. |
| 2006/0183790 | A1 | 8/2006 | Cole et al. |
| 2006/0183792 | A1 | 8/2006 | Fobare et al. |
| 2007/0004730 | A1 | 1/2007 | Zhou |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0191431 | A1 | 8/2007 | Zhou |
| 2007/0203116 | A1 | 8/2007 | Quagliato et al. |

| | | |
|---|---|---|
| 2008/0051390 A1 | 2/2008 | Malamas et al. |

FOREIGN PATENT DOCUMENTS

| | | |
|---|---|---|
| EP | 0861831 A1 | 9/1998 |
| GB | 2013192 A | 8/1979 |
| WO | WO 97/45417 A1 | 12/1997 |
| WO | WO 98/45267 | 10/1998 |
| WO | WO 01/87829 A1 | 11/2001 |
| WO | WO 03/053938 A1 | 7/2003 |
| WO | WO 03/064396 A1 | 8/2003 |
| WO | WO 03/094854 A2 | 11/2003 |
| WO | WO 2004/058727 A1 | 7/2004 |
| WO | WO 2005/005412 A1 | 1/2005 |
| WO | WO 2005/058311 A1 | 6/2005 |
| WO | WO 2006/009653 A1 | 1/2006 |
| WO | WO 2006/065277 A2 | 6/2006 |
| WO | WO 2007/005404 A1 | 1/2007 |
| WO | WO 2007/016012 A2 | 2/2007 |

OTHER PUBLICATIONS

Abbott et al., Molecular Medicine Today, 1996, vol. 2, p. 106-113.
Allimony et al., "Synthesis and antimicrobial activity of some nitrogen heterobicyclic systems: Part I", Indian Journal of Chemistry, 1999, vol. 38B, pp. 445-451.
Fact Sheet Alzheimer's Association, 2006.
Lefrance-Jullien et al., "Design and charaterization of a new cell-permeant inhibitor of the beta-secretase BACE1", British Journal of Pharmacology, 2005, vol. 145, pp. 228-235.
Lyketsos et al., "Position statement of the American Association for Geriatric Psychiatry regarding principles of care for patients with dementia resulting from Alzheimer's Disease", 2006, vol. 14, pp. 561-573.

(Continued)

*Primary Examiner*—Deepak Rao
(74) *Attorney, Agent, or Firm*—Ram W. Sabnis; Scott K. Larsen

(57) ABSTRACT

The present invention provides a compound of formula I and the use thereof for the therapeutic treatment, prevention or amelioration of a disease or disorder characterized by elevated β-amyloid deposits or β-amyloid levels in a patient.

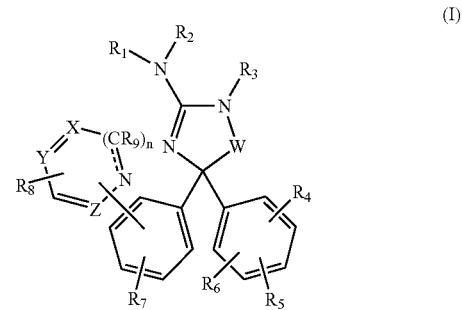

(I)

18 Claims, No Drawings

OTHER PUBLICATIONS

Alzheimer's Disease, retrieved from internet on Jun. 27, 2007, http://www.mayoclinic.com/health/alzheimers-disease/DA00161/DSECTION-3.

National Institute of Neurological Discorders and Stroke, "Alzheimer's Disease Information Page", retrieved from internet on Jun. 27, 2007, http://www.ninds.nih.gov/disorders/alzheimersdisease/alzheimersdisease.htm.

PCT Preliminary Report on Patentability, Written Opinion of the ISR, International Patent Application PCT/US2006/024793, International filing date Jun. 26, 2006.

PCT Preliminary Report on Patentability, Written Opinion of the ISR, International Patent Application PCT/US2006/024912, International filing date Jun. 26, 2006.

Selkoe, "Alzheimer's Disease: Genes, Proteins, and Therapy", Physiological Reviews, 2001, vol. 81(2), pp. 741-766.

Su et al. "Drug delivery across the blood-brain barrier: why is it difficult? How to measure and improve it?", Expert Opinion on Drug Delivery, Abstract, 2006, vol. 3, pp. 419-425.

Tao et al., "Synthesis of Conformationally constrained spirohydantoins with a Dibenzo[a,d]heptadiene ring", Synthesis 2000, No. 10, pp. 1449-1453.

Vandana et al., "Transferring coupled liposomes as drug delivery carriers for brain trageting of 5-florouracil", Journal of Drug Targeting, Abstract, 2005, vol. 13 pp. 245-250.

Varghese et al., "Human beta-secretase (BACE) and BACE Inhibitors", J. Med. Chem. 2003, vol. 46(22), pp. 4625-4630.

Xiao et al., "An improved procedure for the synthesis of 4,4-disubstituted-3-oxo-1,2,5-thiadiazolidine 1,1-dioxides", J. Heterocyclic Chem., 2000, vol. 37, pp. 773-777.

Yamada et al., "Hydantoin derivatives, I. Actions on central nervous system of 5,5-diarylhydantoins and 5,5-diarylhydantion-2-imines", Abstract, Oyo Yakuri, 1975, vol. 9(6), pp. 841-847.

AMINO-5,5-DIPHENYLIMIDAZOLONE DERIVATIVES FOR THE INHIBITION OF β-SECRETASE

This application claims the benefit under 35 U.S.C. §119 (e) to U.S. provisional application No. 60/580,286, filed Jun. 16, 2004, which is hereby incorporated by reference in its entirety.

BACKGROUND OF THE INVENTION

Alzheimer's disease (AD), a progressive degenerative disease of the brain primarily associated with aging, is a serious healthcare problem. Clinically, AD is characterized by the of loss of memory, cognition, reasoning, judgment, and orientation. Also affected, as the disease progresses, are motor, sensory, and linguistic abilities until global impairment of multiple cognitive functions occurs. These cognitive losses take place gradually, but typically lead to severe impairment and eventual death in 4-12 years. Patients with AD display characteristic β-amyloid deposits in the brain and in cerebral blood vessels (β-amyloid angiopathy) as well as neurofibrillary tangles. Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other dementia-inducing disorders.

The family of proteins known as β-amyloid are thought to be causal for the pathology and subsequent cognitive decline in Alzheimer's disease. Proteolytic processing of the amyloid precursor protein (APP) generates amyloid β (A-beta) peptide; specifically, A-beta is produced by the cleavage of APP at the N-terminus by β-secretase and at the C-terminus by one or more γ-secretases. Aspartyl protease enzyme, or β-secretase enzyme (BACE), activity is correlated directly to the generation of A-beta peptide from APP (Sinha, et al, *Nature*, 1999, 402, 537-540). Increasingly, studies indicate that the inhibition of the β-secretase enzyme, inhibits the production of A-beta peptide. The inhibition of β-secretase and consequent lowering of A-beta peptide may lead to the reduction of β-amyloid deposits in the brain and β-amyloid levels in the cerebral blood vessels and to an effective treatment of a disease or disorder caused thereby.

Therefore, it is an object of this invention to provide compounds which are inhibitors of β-secretase and are useful as therapeutic agents in the treatment, prevention or amelioration of a disease or disorder characterized by elevated β-amyloid deposits or β-amyloid levels in a patient.

It is another object of this invention to provide therapeutic methods and pharmaceutical compositions useful for the treatment, prevention or amelioration of a disease or disorder characterized by elevated β-amyloid deposits or β-amyloid levels in a patient.

It is a feature of this invention that the compounds provided may also be useful to further study and elucidate the β-secretase enzyme.

These and other objects and features of the invention will become more apparent by the detailed description set forth hereinbelow.

SUMMARY OF THE INVENTION

The present invention provides an amino-5,5-diphenylimidazolone compound of formula I

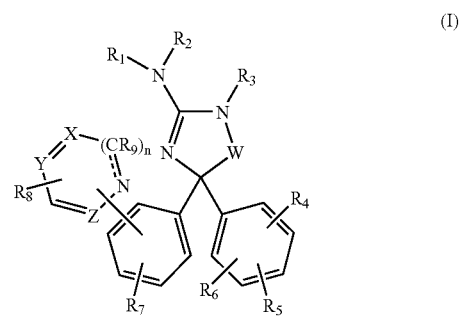

wherein W is CO, CS or $CH_2$;
X is N, NO or $CR_{10}$;
Y is N, NO or $CR_{11}$;
Z is N, NO or $CR_{19}$ with the proviso that no more than two of X, Y or Z may be N or NO;
$R_1$ and $R_2$ are each independently H, $COR_{20}$, $CO_2R_{21}$ or an optionally substituted $C_1$-$C_4$alkyl group;
$R_3$ is H, $OR_{12}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl ($C_1$-$C_6$)alkyl group each optionally substituted;
$R_4$ and $R_5$ are each independently H, halogen, $NO_2$, CN, $OR_{13}$, $NR_{14}R_{15}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted or when attached to adjacent carbon atoms $R_4$ and $R_5$ may be taken together with the atoms to which they are attached to form an optionally substituted 5- to 7-membered ring optionally containing one or two heteroatoms selected from O, N or S;
$R_6$, $R_7$, $R_8$, $R_9$, $R_{10}$, $R_{11}$ and $R_{19}$ are each independently H, halogen, $NO_2$, CN, $OR_{16}$, $NR_{17}R_{18}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
n is 0 or 1;
------ is a single bond when n is 0 or a double bond when n is 1;
$R_{12}$, $R_{13}$, $R_{16}$, $R_{20}$ and $R_{21}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each optionally substituted; and
$R_{14}$, $R_{15}$, $R_{17}$ and $R_{18}$ are each independently H or $C_1$-$C_4$alkyl; or a tautomer thereof, a stereoisomer thereof or a pharmaceutically acceptable salt thereof.

The present invention also provides therapeutic methods and pharmaceutical compositions useful for the treatment, prevention or amelioration of a disease or disorder characterized by increased β-amyloid deposits or increased β-amyloid levels in a patient.

DETAILED DESCRIPTION OF THE INVENTION

Alzheimer's disease (AD) is a major degenerative disease of the brain which presents clinically by progressive loss of memory, cognition, reasoning, judgement and emotional stability and gradually leads to profound mental deteoriation and death. The exact cause of AD is unknown, but increasing evidence indicates that amyloid beta peptide (A-beta) plays a central role in the pathogenesis of the disease. (D. B. Schenk; R. E. Rydel et al, Journal of Medicinal Chemistry, 1995, 21, 4141 and D. J. Selkoe, Physiology Review, 2001, 81, 741).

Patients with AD exhibit characteristic neuropathological markers such as neuritic plaques (and in β-amyloid angiopathy, deposits in cerebral blood vessels) as well as neurofibrillary tangles detected in the brain at autopsy. A-beta is a major component of neuritic plaques in AD brains. In addition, β-amyloid deposits and vascular β-amyloid angiopathy also characterize individuals with Downs Syndrome, Hereditary Cerebral Hemmorhage with Amyloidosis of the Dutch type and other neurodegenreative and dementia-inducing disorders. Over expression of the amyloid precursor protein (APP), altered cleavage of APP to A-beta or a decrease in the clearance of A-beta from a patient's brain may increase the levels of soluble or fibrullar forms of A-beta in the brain. The β-site APP cleaving enzyme, BACE1, also called memapsin-2 or Asp-2, was identified in 1999 (R. Vassar, B. D. Bennett, et al, Nature, 1999, 402, 537). BACE1 is a membrane-bound aspartic protease with all the known functional properties and characteristics of β-secretase. Parallel to BACE1, a second homologous aspartyl protease named BACE2 was found to have β-secretase activity in vitro. Low molecular weight, non-peptide, non-substrate-related inhibitors of BACE1 or β-secretase are earnestly sought both as an aid in the study of the β-secretase enzyme and as potential therapeutic agents.

Surprisingly, it has now been found that amino-5,5-diphenylimidazolone compounds of formula I demonstrate inhibition of β-secretase and the selective inhibition of BACE1. Advantageously, said imidazolone compounds may be used as effective therapeutic agents for the treatment, prevention or amelioration of a disease or disorder characterized by elevated β-amyloid deposits or β-amyloid levels in a patient. Accordingly, the present invention provides an amino-5,5-diphenylimidazolone compound of formula I

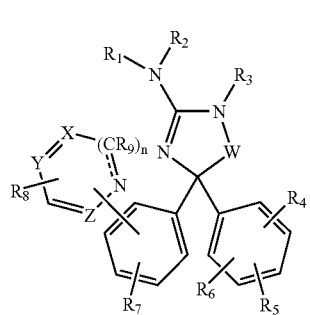

(I)

wherein W is CO, CS or $CH_2$;
X is N, NO or $CR_{10}$;
Y is N, NO or $CR_{11}$;
Z is N, NO or $CR_{19}$ with the proviso that no more than two of X, Y or Z may be N or NO;
$R_1$ and $R_2$ are each independently H, $COR_{20}$, $CO_2R_{21}$ or an optionally substituted $C_1$-$C_4$alkyl group;
$R_3$ is H, $OR_{12}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl ($C_1$-$C_6$)alkyl group each optionally substituted;
$R_4$ and $R_5$ are each independently H, halogen, $NO_2$, CN, $OR_{13}$, $NR_{14}R_{15}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted or when attached to adjacent carbon atoms $R_4$ and $R_5$ may be taken together with the atoms to which they are attached to form an optionally substituted 5- to 7-membered ring optionally containing one or two heteroatoms selected from O, N or S;

$R_6$, $R_7$, $R_8$, $R_9$, $R_{10}$, $R_{11}$ and $R_{19}$ are each independently H, halogen, $NO_2$, CN, $OR_{16}$, $NR_{17}R_{18}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
n is 0 or 1;
----- is a single bond when n is 0 or a double bond when n is 1;
$R_{12}$, $R_{13}$, $R_{16}$, $R_{20}$ and $R_{21}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each optionally substituted; and
$R_{14}$, $R_{15}$, $R_{17}$ and $R_{18}$ are each independently H or $C_1$-$C_4$alkyl; or a tautomer thereof, a stereoisomer thereof or a pharmaceutically acceptable salt thereof.

As used in the specification and claims, the term halogen designates F, Cl, Br or I and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein $X_1$ is NR, O or S; and R is H or an optional substituent as described hereinbelow:

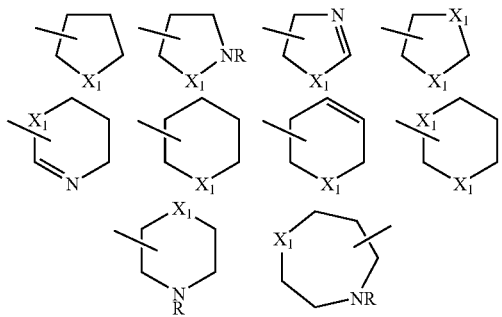

Similarly, as used in the specification and claims, the term heteroaryl designates a five- to ten-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolyl, benzothienyl, benzofuranyl, benzisoxazolyl or the like. The term aryl designates a carbocyclic aromatic ring system such as phenyl, naphthyl, anthracenyl or the like. The term aryl ($C_1$-$C_4$)alkyl designates an aryl group as defined hereinabove attached to a $C_1$-$C_4$alkyl group which may be straight or branched. Said aryl($C_1$-$C_4$)alkyl groups include benzyl, phenethyl, napthtylmethyl, or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different. Preferably the term haloalkyl designates $CF_3$ and the term haloalkoxy designates $OCF_3$.

In the specification and claims, when the terms $C_1$-$C_6$alkyl, $C_2$-$C_6$alkenyl, $C_2$-$C_6$alkynyl, $C_3$-$C_7$cycloalkyl, cycloheteroalkyl, aryl, aryl($C_1$-$C_4$)alkyl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include amides, esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more tautomers. One skilled in the art will recognize that compounds of formula I may also exist as the tautomer It as shown below.

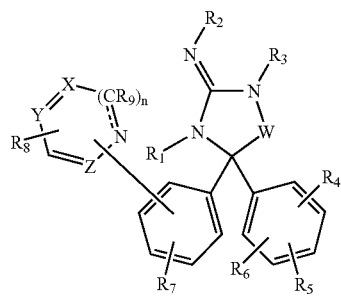

(It)

Tautomers often exist in equilibrium with each other. As these tautomers interconvert under environmental and physiological conditions, they provide the same useful biological effects. The present invention includes mixtures of such tautomers as well as the individual tautomers of Formula I and Formula It.

The compounds of the invention may contain one or more asymmetric carbon atoms or one or more asymmetric (chiral) centers and may thus give rise to optical isomers and diastereomers. Thus, the invention includes such optical isomers and disastereomers; as well as the racemic and resolved, enantiomerically pure stereoisomers; as well as other mixtures of the R and S stereoisomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof, the tautomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein W is CO. Another group of preferred compounds of the invention are those compounds of formula I wherein $R_1$ and $R_2$ are H and $R_3$ is $C_1$-$C_4$ alkyl. Also preferred are those formula I compounds wherein n is 1. A further group of preferred compounds of the invention are those compounds of formula I wherein the nitrogen-containing 5-membered or 6-membered heteroaryl ring is attached to the phenyl ring in the 3-position of the phenyl ring; this preferred group of formula I compounds is designated in the specification and claims as formula Ia. The formula Ia compound is shown below.

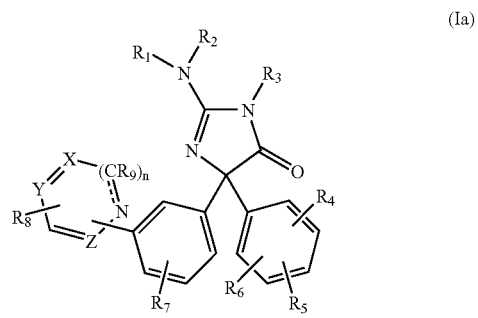

(Ia)

More preferred compounds of the invention are those compounds of formula Ia wherein the nitrogen-containing heteroaryl ring is a 6-membered ring and is attached to the phenyl ring in the 3-position of said heteroaryl ring; this more preferred group of formula I compounds is designated in the specification and claims as formula Ib. Formula Ib is shown below.

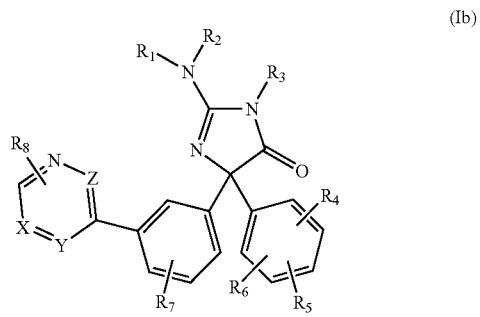

(Ib)

Another group of more preferred compounds of the invention are those compounds of formula Ib wherein $R_3$ is methyl. A further group of more preferred compounds of the invention are those compounds of formula Ib wherein Y is $CR_{11}$; $R_1$ and $R_2$ are H; and $R_3$ is methyl.

Examples of preferred compounds of formula I include:

2-amino-5-(4-fluoro-3-pyrimidin-5-ylphenyl)-5-(4-methoxy-3-methylphenyl)-3-methyl-3,5-dihydro-4H-imidazol-4-one;

(5S)-2-amino-5-[3-(2-fluoropyridin-3-yl)phenyl]-5-(4-methoxy-3-methylphenyl)-3-methyl-3,5-dihydro-4H-imidazol-4-one;
2-amino-5-(4-methoxy-3-methylphenyl)-3-methyl-5-(3-pyrimidin-5-ylphenyl)-3,5-dihydro-4H-imidazol-4-one;
(5S)-2-amino-5-(4-methoxy-3-methylphenyl)-3-methyl-5-(3-pyrimidin-5-ylphenyl)-3,5-dihydro-4H-imidazol-4-one;
(5R)-2-amino-5-(4-fluoro-3-pyrimidin-5-ylphenyl)-3-methyl-5-[4-(trifluoromethoxy)phenyl]-3,5-dihydro-4H-imidazol-4-one;
4-[2-amino-4-(4-methoxy-3-methylphenyl)-1-methyl-5-oxo-4,5-dihydro-1H-imidazol-4-yl]-2-pyridin-3-ylbenzonitrile;
2-amino-5-(4-methoxy-3-methylphenyl)-3-methyl-5-(4-methyl-3-pyridin-3-ylphenyl)-3,5-dihydro-4H-imidazol-4-one;
2-amino-5-[4-methoxy-3-(trifluoromethyl)phenyl]-3-methyl-5-(3-pyridin-3-ylphenyl)-3,5-dihydro-4H-imidazol-4-one;
2-amino-3-ethyl-5-(4-methoxy-3-methylphenyl)-5-(3-pyridin-3-ylphenyl)-3,5-dihydro-4H-imidazol-4-one;
2-amino-5-(4-methoxy-3-methylphenyl)-3-methyl-5-(3-pyrazin-2-ylphenyl)-3,5-dihydro-4H-imidazol-4-one;
2-amino-3-methyl-5-(3-pyrimidin-2-ylphenyl)-5-[4-(trifluoromethoxy)phenyl]-3,5-dihydro-4H-imidazol-4-one;
2-amino-5-(4-hydroxy-3-methylphenyl)-3-methyl-5-(3-pyridin-3-ylphenyl)-3,5-dihydro-4H-imidazol-4-one;
2-amino-5-[4-methoxy-3-(trifluoromethyl)phenyl]-3-methyl-5-(3-pyrazin-2-ylphenyl)-3,5-dihydro-4H-imidazol-4-one;
(5R)-2-amino-5-(4-methoxy-3-methylphenyl)-3-methyl-5-(3-pyrimidin-5-ylphenyl)-3,5-dihydro-4H-imidazol-4-one;
2-amino-5-(4-methoxy-3-methylphenyl)-3-methyl-5-(3-pyridin-3-ylphenyl)-3,5-dihydro-4H-imidazol-4-one;
2-amino-5-(3,4-diethoxyphenyl)-3-methyl-5-(3-pyridin-3-ylphenyl)-3,5-dihydro-4H-imidazol-4-one;
2-amino-5-(3,4-dimethoxyphenyl)-3-methyl-5-(3-pyridin-3-ylphenyl)-3,5-dihydro-4H-imidazol-4-one;
2-amino-5-(3-cyclopentyl-4-methoxyphenyl)-3-methyl-5-(3-pyridin-3-ylphenyl)-3,5-dihydro-4H-imidazol-4-one;
2-amino-5-(4-methoxy-3-propoxyphenyl)-3-methyl-5-(3-pyridin-3-ylphenyl)-3,5-dihydro-4H-imidazol-4-one;
2-amino-5-(3-butoxy-4-methoxyphenyl)-3-methyl-5-(3-pyridin-3-ylphenyl)-3,5-dihydro-4H-imidazol-4-one;
2-amino-5-(3-isopropoxy-4-methoxyphenyl)-3-methyl-5-(3-pyridin-3-ylphenyl)-3,5-dihydro-4H-imidazol-4-one;
2-amino-5-(1,3-benzodioxol-5-yl)-3-methyl-5-(3-pyridin-3-ylphenyl)-3,5-dihydro-4H-imidazol-4-one;
2-amino-5-(2,3-dihydro-1-benzofuran-5-yl)-3-methyl-5-(3-pyridin-3-ylphenyl)-3,5-dihydro-4H-imidazol-4-one;
2-amino-5-[3-(cyclopentyloxy)-4-methoxyphenyl]-3-methyl-5-(3-pyridin-3-ylphenyl)-3,5-dihydro-4H-imidazol-4-one;
5-[2-amino-1-methyl-5-oxo-4-(3-pyridin-3-ylphenyl)-4,5-dihydro-1H-imidazol-4-yl]-2-methoxybenzonitrile;
2-amino-5-(3-fluoro-4-methoxyphenyl)-3-methyl-5-(3-pyridin-3-ylphenyl)-3,5-dihydro-4H-imidazol-4-one;
2-amino-5-(2,3-dihydro-1,4-benzodioxin-6-yl)-3-methyl-5-(3-pyridin-3-ylphenyl)-3,5-dihydro-4H-imidazol-4-one;
2-amino-5-(3-chloro-4-methoxyphenyl)-3-methyl-5-(3-pyridin-3-ylphenyl)-3,5-dihydro-4H-imidazol-4-one;
2-amino-3-methyl-5-(3-pyridin-3-ylphenyl)-5-(3,4,5-trimethoxyphenyl)-3,5-dihydro-4H-imidazol-4-one;
2-amino-5-(4-methoxy-3-methylphenyl)-3-methyl-5-(3-pyridin-4-ylphenyl)-3,5-dihydro-4H-imidazol-4-one;
2-amino-5-(3-ethoxy-4-methoxyphenyl)-3-methyl-5-(3-pyridin-3-ylphenyl)-3,5-dihydro-4H-imidazol-4-one;
2-amino-3-methyl-5-(3-pyridin-3-ylphenyl)-5-[4-(trifluoromethoxy)phenyl]-3,5-dihydro-4H-imidazol-4-one;
2-amino-3-methyl-5-(3-pyridin-3-ylphenyl)-5-[(4-trifluoromethoxy-3-trifluoromethyl)phenyl]-3,5-dihydro-4H-imidazol-4-one;
2-amino-5-(3,4-diethoxyphenyl)-5-(4-fluoro-3-pyridin-3-ylphenyl)-3-methyl-3,5-dihydro-4H-imidazol-4-one;
2-amino-5-(3-chloro-4-trifluoromethoxyphenyl)-5-(4-fluoro-3-pyridin-3-ylphenyl)-3-methyl-3,5-dihydro-4H-imidazol-4-one;

a tautomer thereof; a stereoisomer thereof; or a pharmaceutically acceptable salt thereof.

Advantageously, the present invention provides a process for the preparation of a compound of formula I which comprises reacting a compound of formula II wherein Hal is Cl or Br with a compound of formula III wherein Q is $B(OH)_2$, $Sn(Bu)_3$ or $Sn(CH_3)_3$ in the presence of a palladium catalyst and an inorganic base optionally in the presence of a solvent. The process is shown in flow diagram I, wherein Hal and Q are as defined hereinabove.

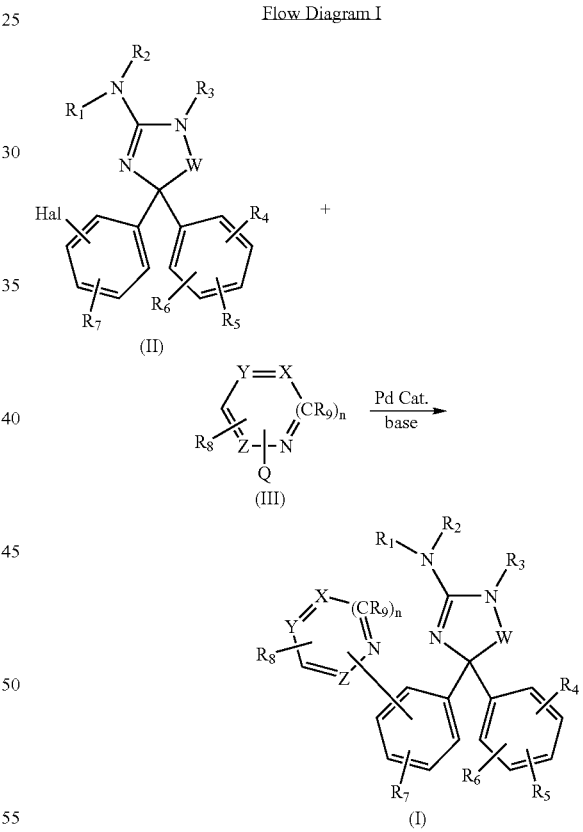

Flow Diagram I

Palladium catalysts suitable for use in the process of the invention include Pd(0) or Pd(II) catalysts such as dichlorobis(tri-o-tolylphosphine)palladium(II), $Pd(OCOCH_3)_2$/tri-o-tolylphosphine, tetrakis(triphenylphosphine)palladium(0), tris(dibenzylideneacetone)dipalladium(0)triphenylphosphine, or the like.

Inorganic bases suitable for use in the inventive process include Na or K hydroxides, carbonates or bicarbonates, preferably $Na_2CO_3$ or $K_2CO_3$.

Solvents suitable for use in the inventive process include polar or non-polar organic solvents such as toluene, diethoxy ethyl ether, dioxane, ethyleneglycol dimethyl ether or any non-reactive organic solvent which is capable of solubilizing the formula II or formula III compounds.

Compounds of formula II may be prepared using conventional synthetic methods and, if required, standard separation or isolation techniques. For example, compounds of formula II wherein W is CO and $R_1$ and $R_2$ are H (IIa), may be prepared by reacting a diketone of formula IV with a substituted guanidine of formula V in the presence of a base such as $Na_2CO_3$ to give the desired compound of formula IIa. The reaction is shown in flow diagram II wherein Hal is Cl or Br.

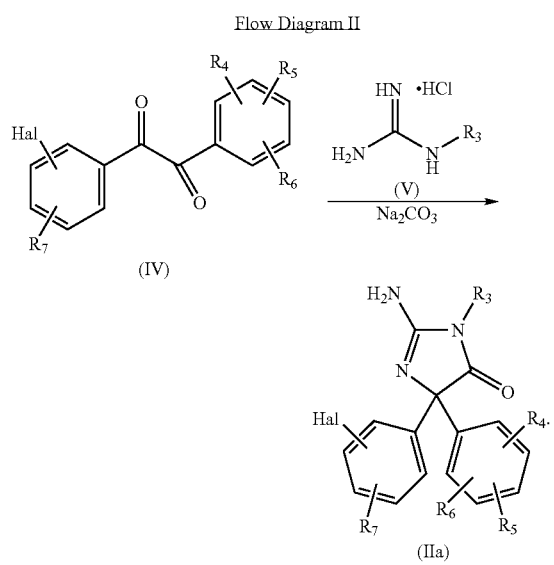

Compounds of formula IV may be prepared by reacting a triphenylphosphonium salt of formula VI with a benzoyl chloride of formula VII in the presence of a base such as $Na_2CO_3$ to form the corresponding triphenylphosphine ylide and oxidizing said ylide with $KMnO_4$ in the presence of $MgSO_4$ to give the desired diketone of formula IV. The reaction is shown in flow diagram III wherein Hal and Hal' are each independently Cl or Br and Ph represents a phenyl group.

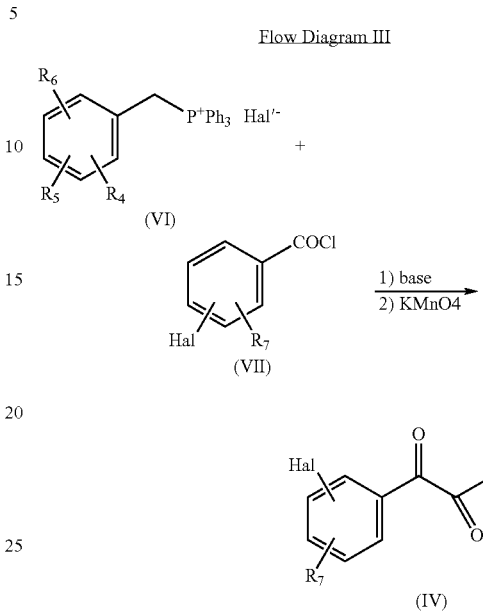

Alternatively, compounds of formula I wherein W is CO and $R_1$ and $R_2$ are H (Ic) may be prepared by reacting a diketone of formula IV with a compound of formula III in the presence of a palladium catalyst and an inorganic base to give the diketone of formula VIII and reacting said formula VIII diketone with a substituted guanidine of formula V (as shown in flow diagram II hereinabove) to give the desired compound of formula Ic. Compounds of formula I wherein $R_1$ is other than H (Id) may be prepared using standard alkylation techniques such as reacting the compound of formula Ic with an alkyl halide, $R_1$-Hal, to give the compound of formula I wherein $R_1$ is other than H and $R_2$ is H (Id). The reaction is shown in flow diagram IV wherein Q is $B(OH)_2$, $Sn(Bu)_3$ or $Sn(CH_3)_3$ and Hal is Cl or Br.

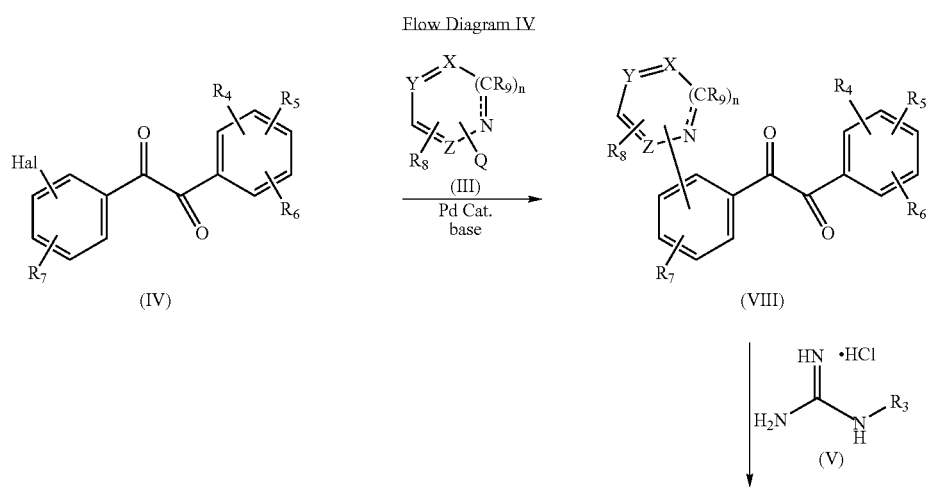

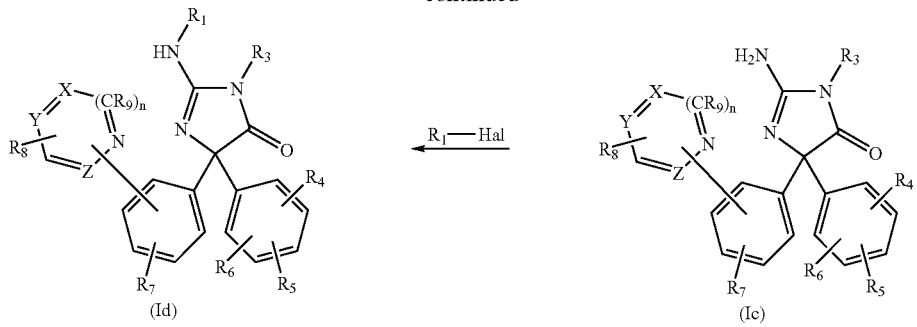

Compounds of formula I wherein W is CO and $R_1$ and $R_2$ are other than H may be prepared by reacting said formula Id compound with a second alkyl halide, $R_2$-Hal, to give the desired formula I compound wherein $R_1$ and $R_2$ are other than H.

Advantageously, the compounds of the invention are useful for the treatment, prevention or amelioration of a disease or disorder characterized by elevated β-amyloid deposits or β-amyloid levels in a patient, including Alzheimer's disease, Downs Syndrome, Hereditary Cerebral Hemorrhage with Amyloidosis of the Dutch type or other neurodegenerative or dementia-inducing disorders. Accordingly, the present invention provides a method for the treatment, prevention or amelioration of a disease or disorder characterized by elevated β-amyloid deposits or β-amyloid levels in a patient which comprises providing said patient with a therapeutically effective amount of a compound of formula I as described hereinabove. The compound may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

As described herein, a therapeutically or prophylactically useful amount of a compound of the invention is that amount of a compound which alleviates the symptoms of the disease, e.g., AD, or which prevents the onset of symptoms, or the onset of more severe symptoms. The useful amounts of a compound may vary depending upon the formulation and route of delivery. For example, higher amounts may be delivered orally than when the compound is formulated for injection or inhalation, in order to deliver a biologically equivalent amount of the drug. Suitably, an individual dose (i.e., per unit) of a compound of the invention is in the range from about 1 μg/kg to about 10 g/kg. Desirably, these amounts are provided on a daily basis. However, the dosage to be used in the treatment or prevention of a specific cognitive deficit or other condition may be subjectively determined by the attending physician. The variables involved include the specific cognitive deficit and the size, age and response pattern of the patient. For example, based upon the activity profile and potency of the compounds of this invention, a starting dose of about 375 to 500 mg per day with gradual increase in the daily dose to about 1000 mg per day may provide the desired dosage level in the human.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

Alternatively, the use of sustained delivery devices may be desirable, in order to avoid the necessity for the patient to take medications on a daily basis. "Sustained delivery" is defined as delaying the release of an active agent, i.e., a compound of the invention, until after placement in a delivery environment, followed by a sustained release of the agent at a later time. Those of skill in the art know suitable sustained delivery devices. Examples of suitable sustained delivery devices include, e.g., hydrogels (see, e.g., U.S. Pat. Nos. 5,266,325; 4,959,217; and 5,292,515), an osmotic pump, such as described by Alza (U.S. Pat. Nos. 4,295,987 and 5,273,752) or Merck (European Patent No. 314,206), among others; hydrophobic membrane materials, such as ethylenemethacrylate (EMA) and ethylenevinylacetate (EVA); bioresorbable polymer systems (see, e.g., International Patent Publication No. WO 98/44964, Bioxid and Cellomeda; U.S. Pat. Nos. 5,756,127 and 5,854,388); other bioresorbable implant devices have been described as being composed of, for example, polyesters, polyanhydrides, or lactic acid/glycolic acid copolymers (see, e.g., U.S. Pat. No. 5,817,343 (Alkermes Inc.)). For use in such sustained delivery devices, the compounds of the invention may be formulated as described herein.

In another aspect, the invention provides a pharmaceutical kit for delivery of a product. Suitably, the kit contains packaging or a container with the compound formulated for the desired delivery route. For example, if the kit is designed for administration by inhalation, it may contain a suspension containing a compound of the invention formulated for aerosol or spray delivery of a predetermined dose by inhalation. Suitably, the kit contains instructions on dosing and an insert regarding the active agent. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the spray pump or other delivery device.

Other suitable components to such kits will be readily apparent to one of skill in the art, taking into consideration the desired indication and the delivery route. The doses may be repeated daily, weekly, or monthly, for a predetermined length of time or as prescribed.

For a more clear understanding, and in order to illustrate the invention more clearly, specific examples thereof are set forth hereinbelow. The following examples are merely illustrative and are not to be understood as limiting the scope and underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

Unless otherwise noted, all parts are parts by weight. The terms HNMR and HPLC designate proton nuclear magnetic resonance and high performance liquid chromatography, respectively. The terms EtOAc and THF designate ethyl acetate and tetrahydrfuran, respectively. In the structures, the term Ph designates a phenyl group.

EXAMPLE 1

Preparation of Ethyl 4-amino-3-bromobenzoate

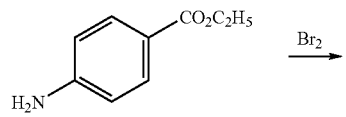

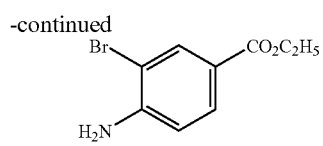

A solution of bromine (7.0 mL, 137.3 mmol) in dichloromethane is added dropwise to a cold (−10° C.) solution of ethyl 4-aminobenzoate (22.0 g, 133.3 mmol) in dichloromethane. The reaction mixture is allowed to come to room temperature, stirred for 18 h and diluted with water. The organic phase is separated, washed twice with brine, dried over $MgSO_4$ and concentrated in vacuo. The resultant residue is purified by flash chromatography ($SiO_2$, 8/1 hexanes/EtOAc as eluent) to afford the title compound as a white solid, 28.6 g (88% yield), identified by HNMR and mass spectral analyses. MS m/e 242 (M−H)$^+$; $^1$H NMR (400 MHz, DMSO-$d_6$) δ 1.28 (t, J=7.01 Hz, 3H), 4.22 (q, J=7.16 Hz, 2H), 6.18 (brs, 2H), 6.81 (d, J=7.91 Hz, 1H), 7.65 (dd, J=8.54, 1.98 Hz 1H), 7.89 (d, J=1.83 Hz, 1H).

EXAMPLE 2

Preparation of 3-Bromo-4-cyanobenzoic acid

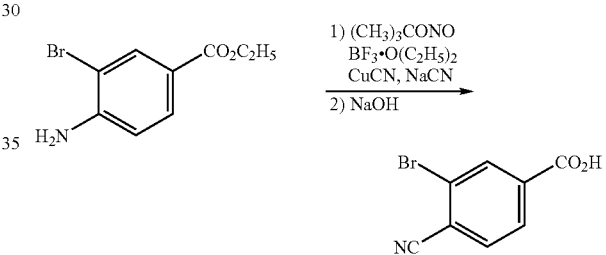

A solution of ethyl 4-amino-3-bromobenzoate (23.5 g, 96.3 mmol) in methylene chloride at −10° C. is treated dropwise with tert-butyl nitrite (14.0 mL, 118.4 mmol), followed by boron trifluoride diethyl etherate (18.4 mL, 146.5 mmol). The reaction mixture is allowed to come to room temperature, stirred for 4 h, diluted with ethyl ether and filtered. The filtercake is dried, dispersed in toluene, cooled to 0° C., treated with a solution of copper (I) cyanide (11.5 g, 129.2 mmol) and sodium cyanide (15.8 g, 323.1 mmol) in water, stirred at 0° C. for 30 min., warmed to 60° C., stirred for 1 h, cooled to room temperature and diluted with EtOAc and water. The organic phase is separated, dried over $MgSO_4$ and concentrated in vacuo. The resultant residue is crystallized from ethyl ether/hexanes to give the ethyl ester of the title compound as an off-white solid, 18.6 g (76% yield). A solution of this ester (8.5 g, 33.6 mmol) in THF is treated with a solution of NaOH (30 mL, 2.5 N) and ethanol, stirred for 20 h, acidified with 2N HCl and extracted with ethyl ether. The ether extracts are combined, dried over $MgSO_4$ and concentrated in vacuo. The resultant residue is crystallized from ethyl ether/hexanes to afford the title compound as a beige solid, 6.81 g (90% yield), identified by HNMR and mass spectral analyses. MS m/e 223 (M−H)$^+$; $^1$H NMR (400 MHz, DMSO-$d_6$) δ 8.05 (dd, J=9.76, 1.37 Hz 1H), 8.09 (d, J=8.08 Hz, 1H), 8.29 (d, J=1.37 Hz, 1H).

EXAMPLE 3

Preparation of 2-Bromo-4-[(4-methoxy-3-methylphenyl)(oxo)acetyl]benzonitrile

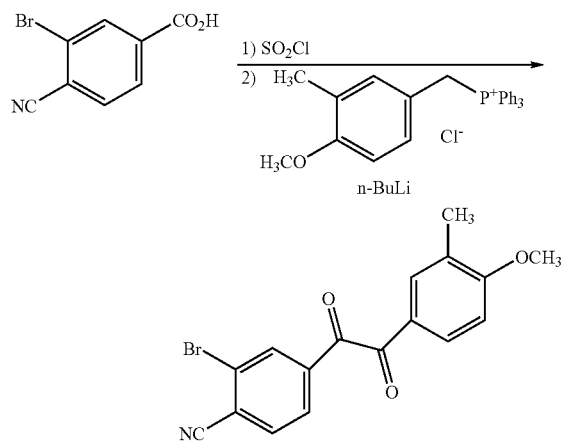

A suspension of 3-bromo-4-cyanobenzoic acid (1.65 g, 7.28 mmol) in thionyl chloride (10 mL) is treated with 3 drops of N,N-dimethylformamide, heated at reflux temperature for 1 h and concentrated in vacuo. This acid chloride residue is re-evaporated 3× with toluene to remove any remaining thionyl chloride. A mixture of 3-methyl-4-methoxybenzyl triphenylphosphonium chloride (6.3 g, 14.55 mmol) in toluene at 0° C. is treated dropwise with n-butyllithium (6.1 mL, 2.5 M in hexanes), allowed to come to room temperature, stirred for 2 h, cooled to 0° C., treated dropwise with a solution of the above-obtained acid chloride in toluene, allowed to come to room temperature, stirred for 2 h, quenched with water and concentrated in vacuo. The resultant residue is dispersed in acetone and water, treated with MgSO$_4$ (7.5 g, 62.5 mmol) and KMnO$_4$ (2.18 g, 13.8 mmol), vigorously stirred at 45° C. for 18 h and filtered. The filtrate is diluted with EtOAc, washed sequentially with water and brine, dried over MgSO$_4$ and evaporated to dryness. This residue is purified by flash chromatography (SiO$_2$, 2/1 hexanes/EtOAc as eluent) to afford the title compound as a yellow solid, 1.8 g (69% yield), identified by HNMR and mass spectral analyses. MS m/e 357 (M+H)$^+$; $^1$H NMR (400 MHz, DMSO-d$_6$) δ 2.21 (s, 3H), 3.93 (s, 3H), 7.15 (d, J=8.54 Hz, 1H), 7.81 (d, J=1.38 Hz, $_1$H), 7.85 (dd, J=8.54, 2.14 Hz, 1H), 8.03 (dd, J=8.08, 1.52 Hz 1H), 8.18 (d, J=8.08 Hz, 1H), 8.30 (d, J=1.38 Hz, 1H).

EXAMPLE 4

Preparation of 4-[(4-Methoxy-3-methylphenyl)(oxo)acetyl]-2-pyridin-3-ylbenzonitrile

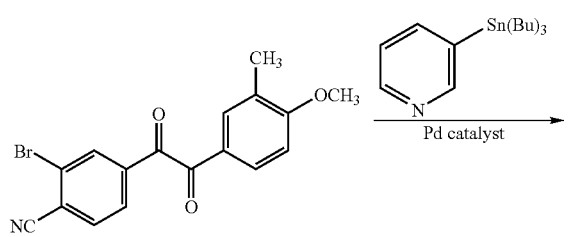

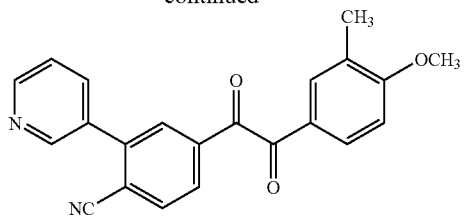

A mixture of 2-bromo-4-[(4-methoxy-3-methylphenyl)(oxo)acetyl]benzonitrile (200 mg, 0.56 mmol) and 3-(tributylstannyl)pyridine (268 mg, 0.73 mmol) in 1,2-diethoxyethane is treated with dichlorobis(tri-o-tolylphosphine)palladium(II) (39.6 mg, 0.05 mmol), heated at 145° C., stirred for 30 min. and filtered to remove the catalyst. The filtrate is evaporated to dryness. The resultant residue is purified by flash chromatography (SiO$_2$, 2/1 hexanes/EtOAc as eluent) and crystallization from ethyl ether/hexanes to afford the title compound as a yellow solid, 181 mg (91% yield), identified by HNMR and mass spectral analyses. MS m/e 357 (M+H)$^+$; $^1$H NMR (400 MHz, DMSO-d$_6$) δ 2.21 (s, 3H), 3.93 (s, 3H), 7.18 (d, J=8.69 Hz, 1H), 7.61 (m, 1H), 7.82 (d, J=8.54, 1H), 7.84 (dd, J=8.54, 1.99 Hz 1H), 8.07 (dd, J=7.76, 1.67 Hz, 1H), 8.12 (m, J=1.38 Hz, 2H), 8.25 (d, J=8.08 Hz, 1H), 8.74 (m, 1H), 8.85 (d, 1.68 Hz, 1H).

EXAMPLE 5

Preparation of 4-[2-amino-4-(4-methoxy-3-methylphenyl)-1-methyl-5-oxo-4,5-dihydro-1H-imidazol-4-yl]-2-pyridin-3-ylbenzonitrile

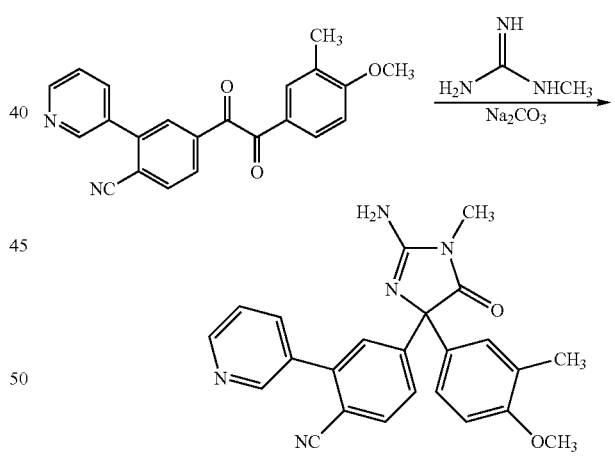

A mixture of 4-[(4-methoxy-3-methylphenyl)(oxo)acetyl]-2-pyridin-3-ylbenzonitrile (160 mg, 0.45 mmol) and 1-methylguanidine hydrochloride (222 mg, 2.02 mmol) in dioxane and ethyl alcohol is treated with Na$_2$CO$_3$ (214 mg, 2.02 mmol) in water, stirred at 85° C. for 3 h and concentrated in vacuo. The resultant residue is partitioned between chloroform and water. The phases are separated and the organic phase is dried over MgSO$_4$ and concentrated in vacuo. This residue is purified by flash chromatography (SiO$_2$, 15/1 EtOAc/methanol as eluent) and crystallization from CHCl$_3$/hexanes to give the title compound as a white solid, 138 mg (75% yield), identified by HNMR and mass spectral analyses. MS m/e 412 (M+H)$^+$; $^1$H NMR (400 MHz, DMSO-d$_6$) δ 2.09

(s, 3H), 2.98 (s, 3H), 3.74 (s, 3H), 6.74 (brs, 2H), 6.86 (d, J=8.69 Hz, 1H), 7.22 (s, 1H), 7.26 (d, J=8.54 Hz, 1H), 7.58 (m, 1H), 7.69 (s, 1H), 7.70 (s, 1H), 7.9-8.0 (m, 2H), 8.7 (m, 2H).

EXAMPLES 6-33

Preparation of Amino-5,5-diphenylimidazolone Derivatives

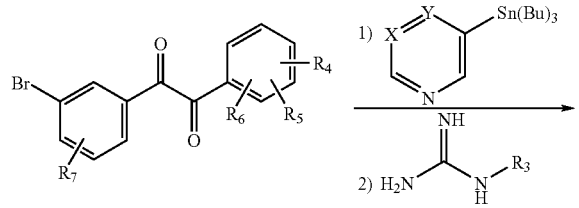
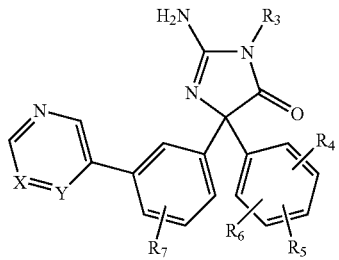

Using essentially the same procedures described in Examples 4 and 5 hereinabove and employing the appropriate dione substrate, tributylstannyl-pyridine or -pyrimidine intermediate and desired guanidine reagent, the compounds shown on Table I are obtained and identified by HNMR and mass spectral analyses.

TABLE I

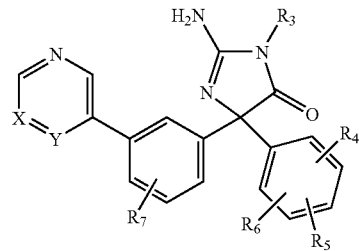

| Ex. No | $R_3$ | $R_4$ | $R_5$ | $R_6$ | $R_7$ | X | Y | mp ° C. |
|---|---|---|---|---|---|---|---|---|
| 6 | $CH_3$ | 3-$CH_3$ | 4-$OCH_3$ | H | 4-$CH_3$ | CH | CH | — |
| 7 | $CH_3$ | 3-$CF_3$ | 4-$OCH_3$ | H | H | CH | CH | — |
| 8 | $C_2H_5$ | 3-$CH_3$ | 4-$OCH_3$ | H | H | CH | CH | — |
| 9 | $CH_3$ | 3-$CH_3$ | 4-$OCH_3$ | H | H | CH | N | — |
| 10 | $CH_3$ | 3-$CH_3$ | 4-OH | H | H | CH | CH | — |
| 11 | $CH_3$ | 3-$CF_3$ | 4-$OCH_3$ | H | H | CH | N | — |
| 12 | $CH_3$ | 3-$CH_3$ | 4-$OCH_3$ | H | H | N | CH | 126 |
| 13 | $CH_3$ | 3-$CH_3$ | 4-$OCH_3$ | H | H | CH | CH | 117-120 |
| 14 | $CH_3$ | 3-$OCH_3$ | 4-$OCH_3$ | H | H | CH | CH | 108-111 |
| 15 | $CH_3$ | 3-cyclopentyl | 4-$OCH_3$ | H | H | CH | CH | 105-110 |
| 16 | $CH_3$ | 3-$OC_3H_7$ | 4-$OCH_3$ | H | H | CH | CH | 103-106 |
| 17 | $CH_3$ | 3-$OC_4H_9$ | 4-$OCH_3$ | H | H | CH | CH | 97-100 |
| 18 | $CH_3$ | 3-$OCH(CH_3)_2$ | 4-$OCH_3$ | H | H | CH | CH | 106-109 |
| 19 | $CH_3$ | 3-Ocyclopentyl | 4-$OCH_3$ | H | H | CH | CH | 117-120 |
| 20 | $CH_3$ | 3-CN | 4-$OCH_3$ | H | H | CH | CH | 140-143 |
| 21 | $CH_3$ | 3-F | 4-$OCH_3$ | H | H | CH | CH | 111-114 |
| 22 | $CH_3$ | 3-Cl | 4-$OCH_3$ | H | H | CH | CH | 112-116 |
| 23 | $CH_3$ | 3-$OCH_3$ | 4-$OCH_3$ | 5-$OCH_3$ | H | CH | CH | 104-107 |
| 24 | $CH_3$ | 3-$OC_2H_5$ | 4-$OCH_3$ | H | H | CH | CH | 125 |
| 25 | $CH_3$ | 3-$OCF_3$ | H | H | H | CH | CH | 198 |
| 26 | $CH_3$ | 3-$CF_3$ | 4-$OCF_3$ | H | H | CH | CH | 98 |
| 27 | $CH_3$ | 3-$OC_2H_5$ | 4-$OC_2H_5$ | H | 4-F | CH | CH | 99-100 |
| 28 | $CH_3$ | 3-Cl | 4-$OCF_3$ | H | 4-F | CH | CH | 99-102 |
| 29 | $CH_3$ | 3-$OC_2H_5$ | 3-$OC_2H_5$ | H | H | CH | CH | 95-99 |
| 30 | $CH_3$ | 3-O—$CH_2$—O-4 | | H | H | CH | CH | 104-106 |
| 31 | $CH_3$ | 3-$CH_2$—$CH_2$—O-4 | | H | H | CH | CH | 122-126 |
| 32 | $CH_3$ | 3-O—$CH_2CH_2$—O-4- | | H | H | CH | CH | 157-160 |
| 33 | H | H | 4-$OCF_3$ | H | 4-F | H | CH | — |

EXAMPLE 34

Preparation of 2-Amino-3-difluoromethyl-5-[4-fluoro-3-(pyrimidin-5-yl)phenyl]-5-[4-(trifluoromethoxy)phenyl]-3,5-dihydro-4H-imidazol-4one

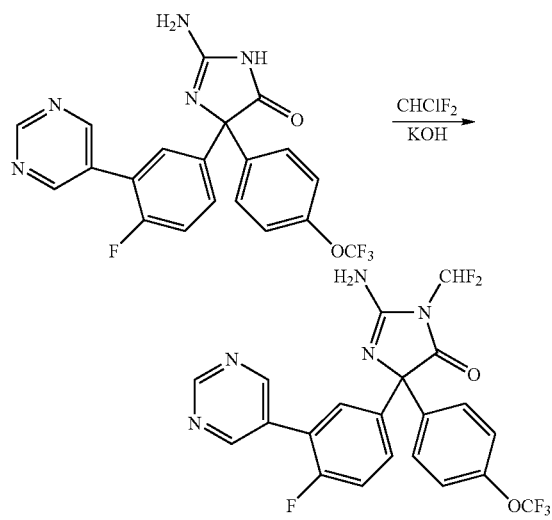

A solution of 2-amino-5-[4-fluoro-3-(pyrimidin-5-yl)phenyl]-5-[4-(trifluoromethoxy)phenyl]-3,5-dihydro-4H-imidazol-4-one (0.398 g, 0.92 mmol) in dimethylformamide is treated with KOH (0.057 g, 1.01 mmol), cooled to −45° C., and bubbled with chlorodifluoromethane (1.40 g, 17.6 mmol). The reaction vessel is sealed and heated at 70° C. for 18 h. The reaction is cooled to room temperature, quenched by careful addition to water, extracted with ethyl acetate, diluted with brine and extracted again with ethyl acetate. The combined extracts are washed with brine, dried over sodium sulfate and concentrated. The resultant residue is purified twice by flash chromatography (silica, 95:5:0.5 to 90:10:0.5 methylene chloride/methanol/concentrated ammonium hydroxide and 100:0 to 98:2 methylene chloride/methanol as eluents) to afford the title compound as a white solid, 0.064 g (14% yield), mp 82-94° C., identified by HNMR, infrared and mass spectral analyses. $^1$H NMR (500 MHz, CDCl$_3$) δ 9.21 (s, 1H), 8.89 (s, 2H), 7.64-7.60 (m, 2H), 7.54 (d, J=8.8 Hz, 2H), 7.23-7.18 (m, 3H), 6.95 (t, J=58 Hz, 1H), 4.92 (br s, 2H); IR (ATR) 3497, 3309, 3149, 1761, 1678, 1497, 1449, 1416, 1252, 1212, 1162 cm$^{-1}$; ESI MS m/z 482 [C$_{21}$H$_{13}$F$_6$N$_5$O$_2$+H]$^+$;

EXAMPLE 35

Preparation of 1-(4-Methoxy-3-methylphenyl)-2-(3-pyridin-4-ylphenyl)ethane-1,2-dione

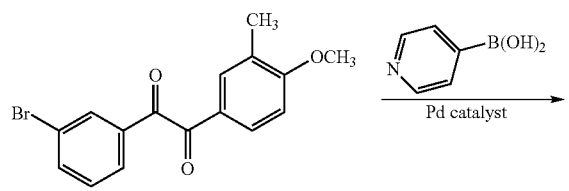

-continued

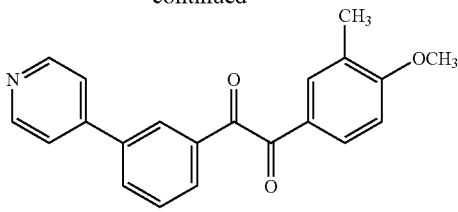

A solution of 1-(3-bromo-phenyl)-2-(4-methoxy-3-methylphenyl)ethane-1,2-dione (0.25 g, 0.75 mmol) in dioxane is treated sequentially with tri-o-tolylphosphine (57 mg, 0.187 mmol), palladium (II) acetate (21 mg, 0.093 mmol), pyridine-4-boronic acid (139 mg, 1.125 mmol) and H$_2$O, stirred at 100° C. for 4 h, cooled to room temperature and filtered. The filtrate is evaporated in vacuo. The resultant residue is purified by flash chromatography on silica gel (hexanes/EtOAc 3/7 as eluent), to afford the title compound as a yellow solid, 0.145 g (58% yield), identified by HNMR and mass spectral analyses. MS m/e (M+H)$^+$ 332; $^1$H NMR (400 MHZ, CDCl$_3$) δ 2.28 (s, 3H) 3.95 (s, 3H) 6.94 (d, 1H) 7.68 (m, 3H) 7.84 (m, 2H) 7.88 (m, 1H) 8.08 (m, 1H) 8.30 (m, 1H) 8.75 (m, 2H).

EXAMPLE 36

Preparation of 2-Amino-5-(4-methoxy-3-methylphenyl)-3-methyl-5-(3-pyridin-4-ylphenyl)-3,5-dihydro-4H-imidazol-4-one

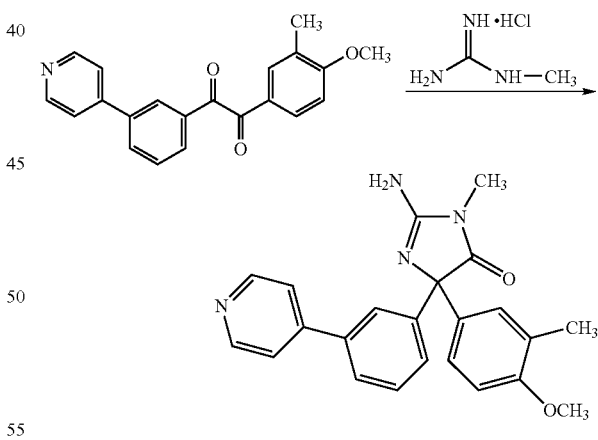

Using essentially the same procedure described in Example 5 hereinabove, and employing 1-(4-methoxy-3-methylphenyl)-2-(3-pyridin-4-ylphenyl)ethane-1,2-dione and 1-methylguanidine hydrochloride as reactants, the title compound is obtained as a white solid, 0.15 g (90% yield), mp 175° C., identified by HNMR and mass spectral analyses. MS m/e (M)$^+$387; $^1$H NMR (400 MHZ, DMSO-d$_6$) δ 2.05 (s, 3H) 3.00 (s, 3H) 3.75 (s, 3H) 6.60 (bs, 2H) 6.82 (d, 1H) 7.20 (m, 1H) 7.25 (m, 1H) 7.40 (m, 1H) 7.50 (m, 3H) 7.62 (m, 1H) 7.8 (m, 1H) 8.6 (m, 2H).

EXAMPLE 37

Preparation of 2-Amino-3-methyl-5-(3-pyrimidin-2-ylphenyl)-5-[4-(trifluoromethoxy)phenyl]-3,5-dihydro-4H-imidazol-4-one

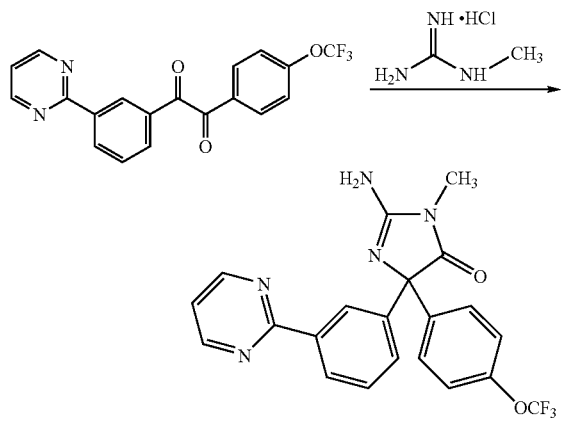

Using essentially the same procedure described in Example 36 hereinabove and employing 1-(3-pyrimidin-2-ylphenyl)-2-[4-(trifluoromethoxy)phenyl]ethane-1,2-dione and methylguanidine hydrochloride as reactants, the title compound is obtained as a white solid, identified by HNMR and mass spectral analyses. MS m/e 428 (M+H)+; $^1$H NMR (400 MHz, DMSO-$d_6$) δ 3.01 (s, 1H), 6.79 (brs, 2H), 7.33-7.49 (m, 2H), 7.58-7.66 (m, 3H), 8.27 (m, 2H), 7.59 (d, J=7.77 Hz, 1H), 7.98 (d, J=7.47 Hz, 1H), 8.26 (s, 1H), 8.61 (t, J=1.67 Hz, 1H), 8.90 (d, J=4.88 Hz, 2H).

EXAMPLE 38

Preparation of (5R)-2-Amino-5-(4-methoxy-3-methylphenyl)-3-methyl-5-(3-pyrimidin-5-ylphenyl)-3,5-dihydro-4H-imidazol-4-one (A) and (5S)-2-Amino-5-(4-methoxy-3-methylphenyl)-3-methyl-5-(3-pyrimidin-5-ylphenyl)-3,5-dihydro-4H-imidazol-4-one (B)

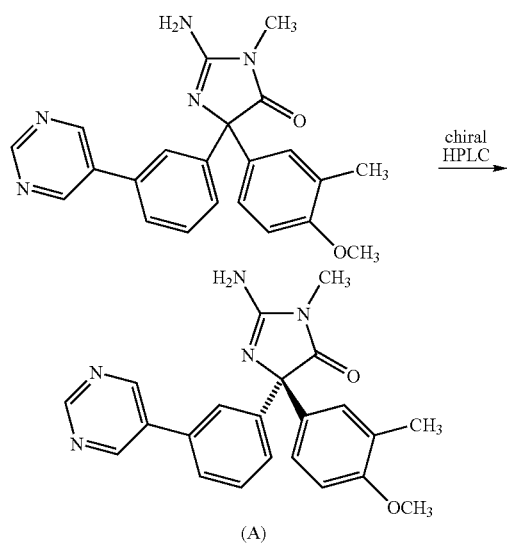

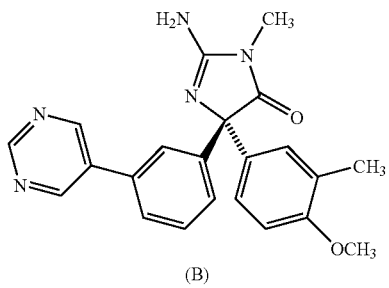

Racemic 2-amino-5-(4-methoxy-3-methylphenyl)-3-methyl-5-(3-pyrimidin-5-ylphenyl)-3,5-dihydro-4H-imidazol-4-one is resolved using chiral HPLC technique on a Chiralcel AD, 2×25 cm and using as mobile phase 50% IPA/DEA in 7200/DEA with a flow rate of 10 mL/min. The R-isomer, title compound A, is obtained, after crystallization from chloroform/hexane as a white solid, 98% ee; identified by HNMR and mass spectral analyses. MS m/e 388 (M+H)+; $^1$H NMR (400 MHz, DMSO-$d_6$) δ 2.07 (s, 3H), 2.97 (s, 3H), 3.72 (s, 3H), 6.63 (brs, 2H), 6.85 (d, J=8.39 Hz, 1H), 7.21 (s, 1H), 7.25 (dd, J=7.88, 1.01, 1H), 7.46 (t, J=7.55 Hz, 1H), 7.52 (d, J=7.89 Hz, 1H), 7.63 (dd, J=7.54, 0.84 Hz, 1H), 7.75 (s, 1H), 8.99 (s, 2H), 9.18 (s, 1H). $[α]_D^{25}$=+40.2 (c=1% in CH$_3$OH)

The S-isomer, title compound B, is obtained, after crystallization from chloroform/hexane as a white solid, 95% ee; identified by HNMR and mass spectral analyses. MS m/e 388 (M+H)+; $^1$H NMR (400 MHz, DMSO-$d_6$) δ 2.07 (s, 3H), 2.97 (s, 3H), 3.72 (s, 3H), 6.63 (brs, 2H), 6.85 (d, J=8.39 Hz, 1H), 7.21 (s, 1H), 7.25 (dd, J=7.88, 1.01, 1H), 7.46 (t, J=7.55 Hz, 1H), 7.52 (d, J=7.89 Hz, 1H), 7.63 (dd, J=7.54, 0.84 Hz, 1H), 7.75 (s, 1H), 8.99 (s, 2H), 9.18 (s, 1H). $[α]_D^{25}$=−79.6 (c=0.67% in CH$_3$OH)

Absolute configuration for each of title compound A and B is determined by x-ray crystallography.

EXAMPLE 39

Preparation of 2-Amino-5-(3-bromo-4-fluorophenyl)-5-[3-fluoro-4-(trifluoromethoxy)phenyl]-3-methyl-3,5-dihydroimidazol-4-one

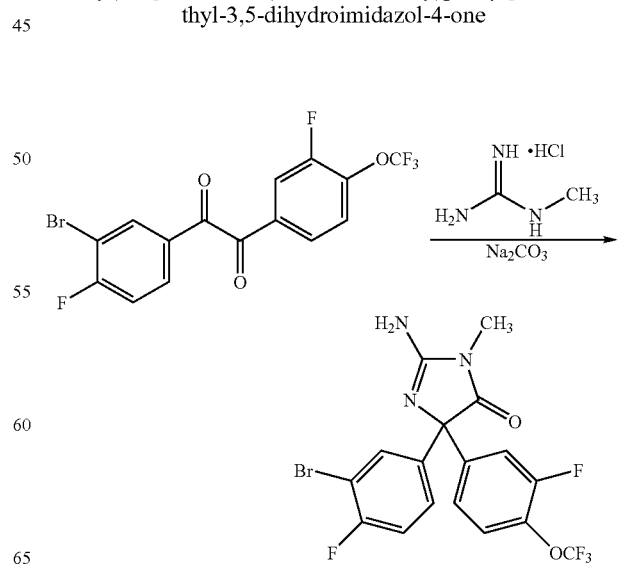

A mixture of 1-(3-bromo-4-fluorophenyl)-2-[3-fluoro-4-(trifluoromethoxy)-phenyl]ethane-1,2-dione (0.594 g, 1.45 mmol) and 1-methylguanidine hydrochloride (0.716 g, 6.53 mmol) in dioxane and ethanol is stirred at room temperature for 5 min., treated with a solution of sodium carbonate (0.692 g, 6.53 mmol) in water (5 mL), heated at 85° C. with stirring for 45 min., cooled to room temperature, and concentrated in vacuo. The resultant residue is partitioned between methylene chloride and water. The organic phase is separated, washed with sequentially with water and brine, dried over sodium sulfate and concentrated in vacuo. This residue is purified by flash chromatography (silica, 95:5:0.5 methylene chloride/methanol/concentrated ammonium hydroxideas eluent) to afford a viscous oil. This oil is dissolved in a minimal amount of methylene chloride, treated with hexanes and then concentrated to afford the title product as an off-white solid, 0.30 g (45% yield), identified by HNMR and mass spectral analyses. $^1$H NMR (500 MHz, CD$_3$OD) δ 7.64 (dd, J=6.6, 2.2 Hz, 1H), 7.43-7.37 (m, 2H), 7.33 (dd, J=11.5, 2.1 Hz, 1H), 7.30 (m, 1H), 7.18 (t, J=8.6 Hz, 1H), 3.11 (s, 3H); ESI MS m/z 464 [C$_{17}$H$_{11}$BrF$_5$N$_3$O$_2$+H]$^+$.

EXAMPLE 40

Preparation of 2-Amino-5-(4-fluoro-3-pyrimidin-5-ylphenyl)-5-[3-fluoro-4-(trifluoromethoxy)phenyl]-3-methyl-3,5-dihydro-imidazol-4-one

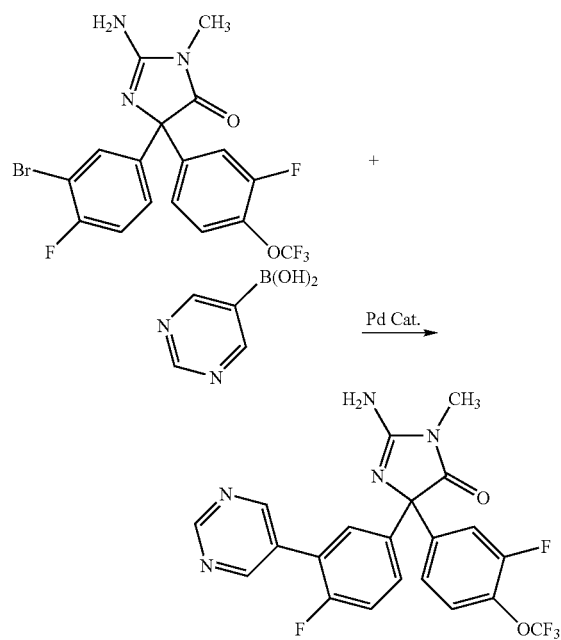

A mixture of ethylene glycol dimethyl ether, tris(dibenzylideneacetone)-dipalladium(0) (0.015 g, 16.5 μmol) and triphenylphosphine (0.008 g, 32.0 μmol) under nitrogen is stirred for 5 min, treated with 2-amino-5-(3-bromo-4-fluorophenyl)-5-[3-fluoro-4-(trifluoromethoxy)phenyl]-3-methyl-3,5-dihydroimidazol-4-one (0.154 g, 0.33 mmol), 5-pyrimidine boronic acid (0.046 g, 0.37 mmol), sodium carbonate (0.105 g, 0.99 mmol) and water, heated at reflux temperature for 1.25 h, cooled to room temperature and concentrated in vacuo. The resultant residue is purified by flash chromatography (silica, 95:5:0.5 methylene chloride/methanol/concentrated ammonium hydroxide as eluent) to afford a viscous oil. This oil is suspended in a mixture of methylene chloride/hexanes and concentrated to afford the title compound as an off-white solid, 0.045 g (29% yield), mp 102-110° C., identified by HNMR and mass spectral analyses. $^1$H NMR (500 MHz, CD$_3$OD) δ 9.15 (s, 1H), 8.95 (s, 2H), 7.62-7.56 (m, 2H), 7.39-7.27 (m, 4H), 3.12 (s, 3H); IR 3353, 3061, 2956, 1732, 1668, 1498, 1470, 1416, 1251, 1216, 1170 cm$^{-1}$; ESI MS m/z 464 [C$_{21}$H$_{14}$F$_5$N$_5$O$_2$+H]$^+$; HPLC (Method 2) 95.0% (AUC) t$_R$=13.78 min.

EXAMPLE 41

Preparation of 2-Amino-5-[4-fluoro-3-(5-fluoropyridin-3-yl)phenyl]-5-[3-fluoro-4-(trifluoromethoxy)phenyl]-3-methyl-3,5-dihydro-imidazol-4-one

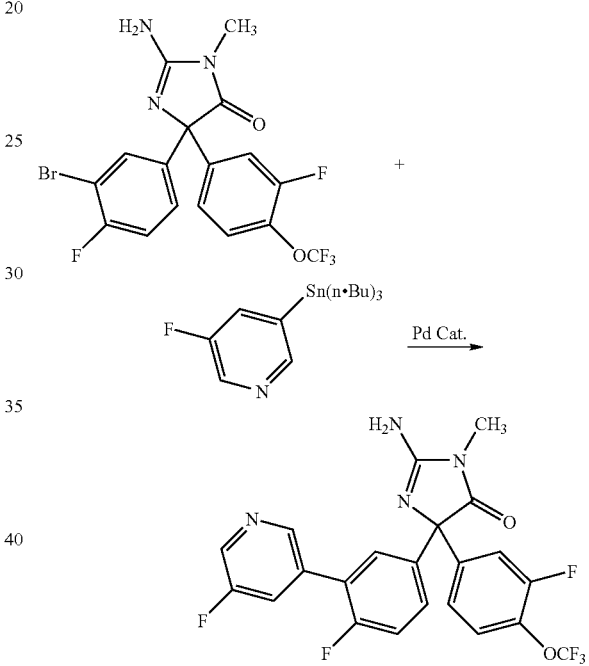

A mixture of 2-amino-5-(3-bromo-4-fluorophenyl)-5-[3-fluoro-4-(trifluoromethoxy)phenyl]-3-methyl-3,5-dihydroimidazol-4-one (0.17 g, 0.366 mmol), 5-fluorpyridin-3-yl-tri(n-butyl)stannate (0.212 g, 0.55 mmol) and bis(triphenylphosphino)palladium(II) chloride (0.013 g, 0.018 mmol) in dimethyl formamide is degassed, heated at 150° C. for 1 h, cooled to room temperature and diluted with ethyl acetate and 2% aqueous lithium chloride. The organic phase is separated, washed with 2% aqueous lithium chloride, dried over sodium sulfate and concentrated in vacuo. Purification of the resultant residue by flash chromatography (silica, 97:3:0.25 methylene chloride/methanol/concentrated ammonium hydroxide as eluent) affords the title compound as a white solid, 0.130 g (74% yield), mp 91-97° C.; identified by HNMR and mass spectral analyses. $^1$H NMR (300 MHz, CD$_3$OD) 8.55 (m, 1H), 8.49 (d, J=3.0 Hz, 1H), 7.83 (d, J=9.6 Hz, 1H), 7.60-7.21 (m, 6H), 3.13 (s, 3H); IR (ATR) 3352, 3070, 1732, 1669, 1598, 2502, 1479, 1421, 1252, 1217, 1171, 883, 817, 794, 703 cm$^{-1}$; ESI MS m/z 481

EXAMPLES 42-99

Preparation of 2-Amino-5,5-diphenylimidazolone Derivatives

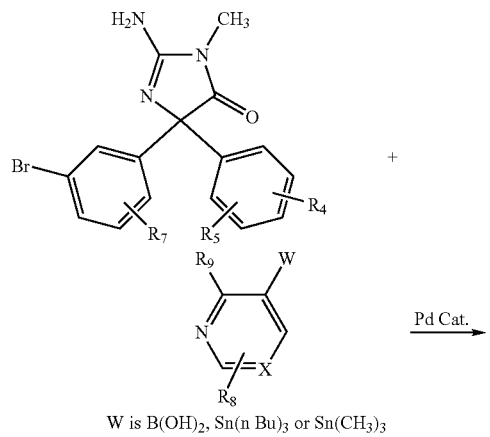

W is B(OH)$_2$, Sn(n Bu)$_3$ or Sn(CH$_3$)$_3$

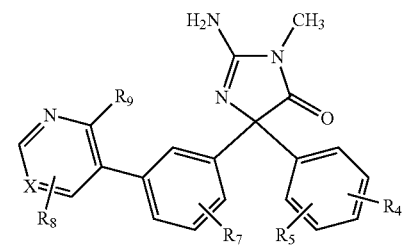

Using essentially the same procedures described hereinabove for examples 40 and 41 and employing the appropriate 2-amino-5-(3-bromophenyl)-5-(substituted-phenyl)imidazolone substrate and pyridinyl or pyrimidinyl reagent, the compounds shown on Table II were obtained and identified by HNMR and mass spectral analyses.

TABLE II

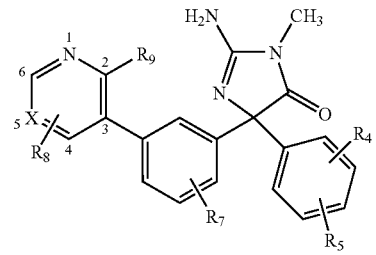

| Ex. No | R$_4$ | R$_5$ | R$_7$ | R$_9$ | R$_8$ | X | mp ° C. |
|---|---|---|---|---|---|---|---|
| 42 | 3-F | 4-OCF$_3$ | 4-F | H | H | C—Cl | 201-203 |
| 43 | 3-F | 4-OCF$_3$ | 4-F | F | H | CH | 75-80 |
| 44 | 3-OC$_2$H$_5$ | 4-OC$_2$H$_5$ | H | H | H | N | 100-105 |
| 46 | H | 4-OCF$_3$ | 4-F | H | H | C—Cl | 241-243 |
| 47 | H | 4-OCF$_3$ | 4-F | H | H | C—F | 216-218 |
| 48 | H | 4-OCF$_3$ | 2-F | H | H | N | 130-135 |
| 49 | H | 4-OCF$_3$ | 4-Cl | H | H | N | 124-129 |
| 50 | H | 4-OCF$_3$ | 4-F | H | H | CH | 134 |
| 51 | H | 4-OCF$_3$ | H | H | H | C—OCH$_3$ | 212 |
| 52 | H | 4-OCF$_3$ | H | OCH$_3$ | H | CH | 96 |
| 53 | H | 4-OCF$_3$ | 3-F | H | H | N | 226 |
| 54 | 3-CH$_3$ | 4-OCH$_3$ | 4-F | H | H | N | 116 |
| 55 | 3-CH$_3$ | 4-OCH$_3$ | 4-F | F | H | CH | 113 |
| 56 | 3-CF$_3$ | 4-OCH$_3$ | 4-F | H | H | N | 115 |
| 57 | 3-CF$_3$ | 4-OCH$_3$ | 4-F | H | 6-F | CH | 135 |
| 58 | 3-CF$_3$ | 4-OCH$_3$ | 4-F | F | H | CH | 118 |
| 59 | 3-CH$_3$ | 4-OCH$_3$ | H | F | H | CH | 125 |
| 60 | H | 4-OCH$_3$ | 4-F | H | H | C—F | — |
| 61 | 3-CH$_3$ | 4-OCH$_3$ | 4-F | H | H | C—F | — |
| 62 | H | 4-OCH$_3$ | 4-F | F | H | CH | — |
| 63 | H | 4-OCH$_3$ | 4-F | H | H | N | — |
| 64 | H | 4-OCF$_3$ | H | H | 6-OCH$_3$ | CH | — |
| 65 | H | 4-OCF$_3$ | H | H | 6-F | CH | — |
| 66 | H | 4-OCF$_3$ | H | F | H | CH | — |
| 67 | 3-OC$_2$H$_5$ | 4-OC$_2$H$_5$ | H | H | H | C—OCH$_3$ | — |
| 68 | 3-OC$_2$H$_5$ | 4-OC$_2$H$_5$ | H | OCH$_3$ | H | CH | — |
| 69 | 3-OC$_2$H$_5$ | 4-OC$_2$H$_5$ | H | H | 6-F | CH | — |
| 70 | 3-OC$_2$H$_5$ | 4-OC$_2$H$_5$ | H | F | H | CH | — |
| 71 | H | 4-OCF$_3$ | 4-F | H | H | C—OCH$_3$ | — |
| 72 | H | 4-OCF$_3$ | 4-F | OCH$_3$ | H | CH | — |
| 73 | H | 4-OCF$_3$ | 4-F | H | 6-F | CH | — |
| 74 | H | 4-OCF$_3$ | 4-F | F | H | CH | — |
| 75 | 3-CH$_3$ | 4-OCH$_3$ | H | OCH$_3$ | H | CH | — |
| 77 | H | 4-OCF$_3$ | 4-F | H | H | N | — |
| 78 | 3-F | 4-OCF3 | 4-F | H | 4-F | CH | 93-96 |

TABLE II-continued

| Ex. No | R₄ | R₅ | R₇ | R₉ | R₈ | X | mp °C. |
|---|---|---|---|---|---|---|---|
| 79 | 3-C₂H₅ | 3-C₂H₅ | 4-F | F | H | CH | 95-100 |
| 80 | H | 4-OCH₃ | 4-F | H | H | C—Cl | — |
| 81 | 3-OC₂H₅ | 4-OC₂H₅ | H | H | 4-F | CH | — |
| 82 | H | 4-OCF₃ | H | H | 4-F | CH | — |
| 83 | H | 4-OCH₃ | 4-F | H | 4-F | CH | — |
| 84 | H | 4-OCF₃ | 6-F | H | H | CH | — |
| 85 | H | 4-OCF₃ | 2-F | H | H | CH | 239 |
| 86 | 3-OC₂H₅ | 4-OC₂H₅ | 4-F | H | H | N | 95-98 |
| 87 | H | 4-OCHF₂ | 4-F | H | H | C—F | — |
| 88 | H | 4-OCHF₂ | 4-F | H | 6-F | CH | — |
| 89 | H | 4-OCHF₂ | H | F | H | CH | — |
| 90 | H | 4-OCHF₂ | H | H | 6-F | CH | — |
| 91 | H | 4-OCHF₂ | H | F | H | C—F | — |
| 92 | H | 4-OCHF₂ | 4-F | F | H | C—F | — |
| 93 | H | 4-SCF₃ | 4-F | F | H | CH | 95 |
| 94 | H | 4-SCF₃ | 4-F | H | H | N | 183 |
| 95 | H | 4-OCHF₂ | 4-F | H | H | CH | 104-106 |
| 96 | H | 4-OCHF₂ | 4-F | F | H | CH | 108-110 |
| 97 | H | 4-OCHF₂ | 4-F | H | H | N | 103-105 |
| 99 | 3-OC₂H₅ | 4-OC₂H₅ | 4-F | H | H | CH | 93-95 |

EXAMPLE 100

Preparation of 2-Amino-5-[4-fluoro-3-(1-methyl-1H-pyrazol-4-yl)phenyl]3-methyl-5-[4-(trifluoromethoxy)phenyl]-3,5-dihydro-4H-imidazol-4-one

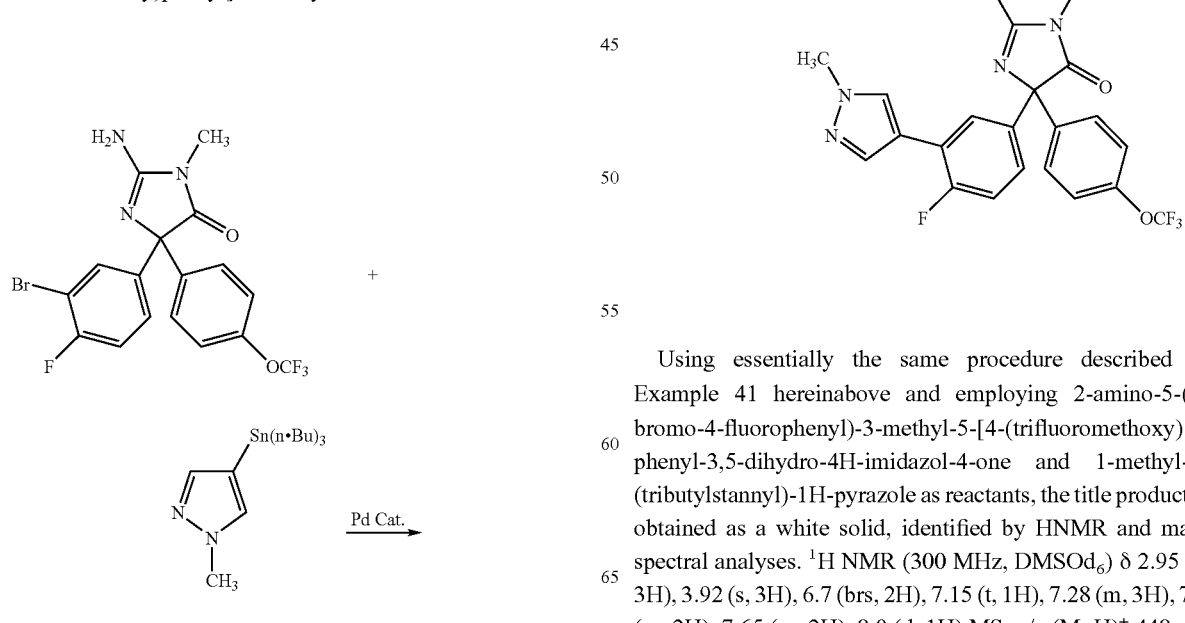

Using essentially the same procedure described in Example 41 hereinabove and employing 2-amino-5-(3-bromo-4-fluorophenyl)-3-methyl-5-[4-(trifluoromethoxy)phenyl-3,5-dihydro-4H-imidazol-4-one and 1-methyl-4-(tributylstannyl)-1H-pyrazole as reactants, the title product is obtained as a white solid, identified by HNMR and mass spectral analyses. ¹H NMR (300 MHz, DMSOd₆) δ 2.95 (s, 3H), 3.92 (s, 3H), 6.7 (brs, 2H), 7.15 (t, 1H), 7.28 (m, 3H), 7.5 (m, 2H), 7.65 (m, 2H), 8.0 (d, 1H) MS m/e (M+H)⁺ 448

EXAMPLE 101

Preparation of (5S)-2-Amino-5-(4-fluoro-3-pyrimidin-5-ylphenyl)-3-methyl-5-[4-(trifluoromethoxy)phenyl]-3,5-dihydro-4H-imidazol-4one (A) and (5R)-2-Amino-5-(4-fluoro-3-pyrimidin-5-ylphenyl)-3-methyl-5-[4-(trifluoromethoxy)phenyl]-3,5-dihydro-4H-imidazol-4-one (B)

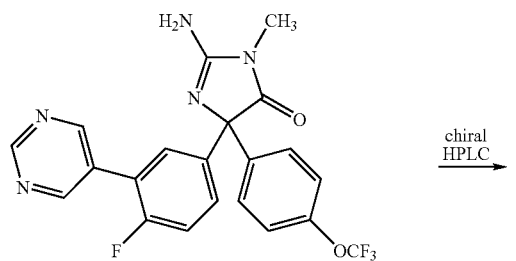

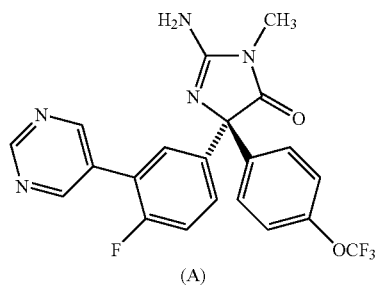
(A)

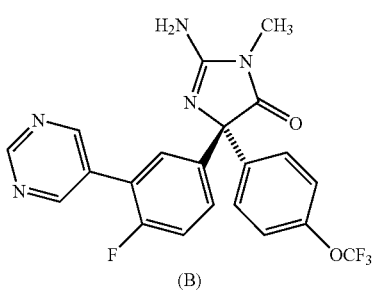
(B)

Racemic 2-amino-5-(4-fluoro-3-pyrimidin-5-ylphenyl)-3-methyl-5-[4-(trifluoromethoxy)phenyl]-3,5-dihydro-4H-imidazol-4-one is resolved using chiral HPLC technique on a Chiralcel AD, 2×25 cm and using as mobile phase EtOH with a flow rate of 11 mL/min. The S-isomer, title compound A, is obtained, after crystallization from chloroform/hexanes, as a white solid, 98.8% ee; identified by HNMR and mass spectral analyses. $^1$H NMR (300 MHz, DMSOd$_6$) δ 2.95 (s, 3H), 3.95 (m, 4H), 6.72 (brs, 2H), 7.25 (d, 2H), 7.32 (t, 1H), 7.55-7.6 (m, 3H), 7.65 (dd, 1H), 8.9 (s, 2H), 9.2 (s, 1H) MS m/e (M+H)$^+$ 446

The R-isomer, title compound B, is obtained, after crystallization from chloroform/hexanes, as a white solid, 98.4% ee; identified by HNMR and mass spectral analyses. $^1$H NMR (300 MHz, DMSOd$_6$) δ 2.95 (s, 3H), 3.95 (m, 4H), 6.72 (brs, 2H), 7.25 (d, 2H), 7.32 (t, 1H), 7.55-7.6 (m, 3H), 7.65 (dd, 1H), 8.9 (s, 2H), 9.2 (s, 1H) MS m/e (M+H)$^+$ 446

EXAMPLE 102

Preparation of (5R)-2-Amino-5-[3-(2-fluoropyridin-3-yl)phenyl]-5-(4-methoxy-3-methylphenyl]-3-methyl-3,5-dihydro-4H-imidazol-4-one (A) and (5S)-2-Amino-5-[3-(2-fluoropyridin-3-yl)phenyl]-5-(4-methoxy-3-methylphenyl]-3-methyl-3,5-dihydro-4H-imidazol-4-one (B)

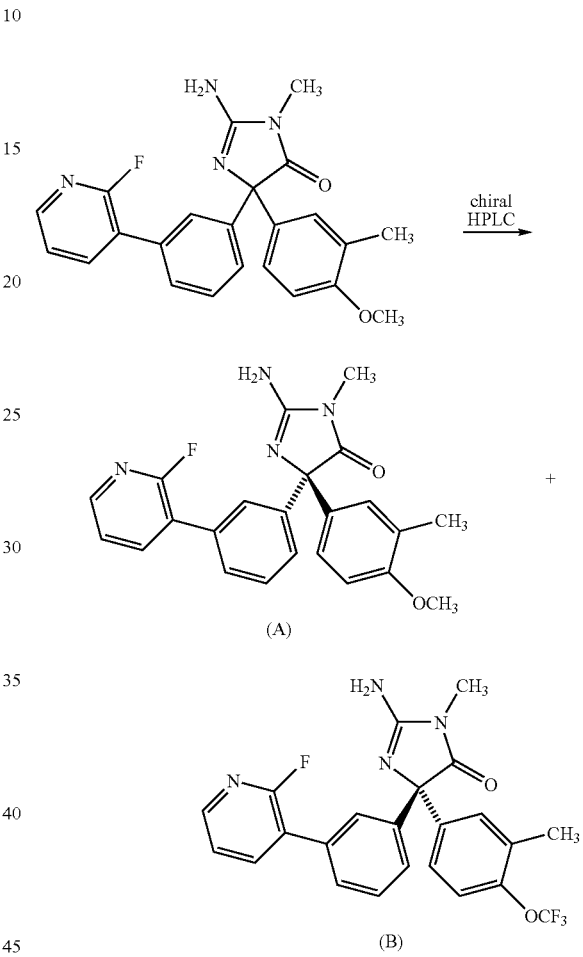

Racemic 2-amino-5-[3-(2-fluoropyridin-3-yl)phenyl]-5-(4-methoxy-3-methylphenyl]-3-methyl-3,5-dihydro-4H-imidazol-4-one is resolved using chiral HPLC technique on a Chiralcel AD, 2×25 cm and using as mobile phase 9% EtOH/DEA in hexane/DEA with a flow rate of 25 mL/min. The R-isomer, title compound A, is obtained, after crystallization from chloroform/hexanes, as a white solid, 100% ee; identified by HNMR and mass spectral analyses. $^1$H NMR (300 MHz, DMSOd$_6$) δ 2.05 (s, 3H), 2.96 (s, 3H), 3.67 (s, 3H), 6.62 (brs, 2H), 6.6 (d, 1H), 7.25-7.35 (m, 2H), 7.35-7.5 (m, 2H), 7.65 (m, 1H), 7.95 (m, 2H), 8.4 (dd, 1H) MS m/e (M+H)$^+$ 405 [α]$_D^{25}$=+22 (c=1% in CH$_3$OH)

The S-isomer, title compound B, is obtained, after crystallization from chloroform/hexanes, as a white solid, 98% ee; identified by HNMR and mass spectral analyses. $^1$H NMR (300 MHz, DMSOd$_6$) δ 2.05 (s, 3H), 2.96 (s, 3H), 3.67 (s, 3H), 6.62 (brs, 2H), 6.6 (d, 1H), 7.25-7.35 (m, 2H), 7.35-7.5 (m, 2H), 7.65 (m, 1H), 7.95 (m, 2H), 8.4 (dd, 1H) MS m/e (M+H)$^+$ 405 [α]$_D^{25}$=−9.5 (c=0.4% in CH$_3$OH)

EXAMPLE 103

Preparation of (5R)-2-Amino-5-(3,4-diethoxyphenyl)-5-[3-(2-fluoropyridin-3-yl)phenyl]-3-methyl-3,5-dihydro-4H-imidazol-4-one (A) and (5S)-2-Amino-5-(3,4-diethoxyphenyl)-5-[3-(2-fluoropyridin-3-yl)phenyl]-3-methyl-3,5-dihydro-4H-imidazol-4-one (B)

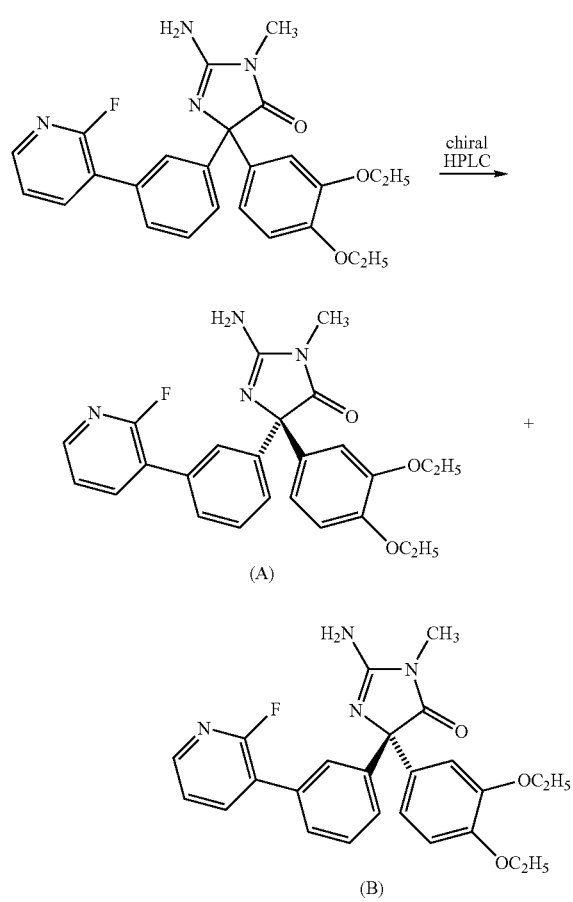

Racemic 2-amino-5-(3,4-diethoxyphenyl)-5-[3-(2-fluoropyridin-3-yl)phenyl]-3-methyl-3,5-dihydro-4H-imidazol-4-one is resolved using chiral HPLC technique on a Chiralcel AD, 0.46×25 cm column and using as mobile phase 25% EtOH in hexanes/DEA. The R-isomer, title compound A, is obtained and identified by HNMR and mass spectral analyses. $^1$H NMR (DMSOd$_6$ 300 MHz) δ 1.22 (m, 6H), 2.95 (s, 3H), 3.95 (m, 4H), 6.6 (brs, 2H), 6.85 (d, 1H), 7.0 (m, 2H), 7.37-7.45 (m, 3H), 7.48 (d, 1H), 7.63 (s, 1H), 7.96 (m, 1H), 8.2 (d, 1H) MS m/e (M+H)$^+$ 449 $[α]_D^{25}$=+7.4 (c=1% in CH$_3$OH)

The S-isomer, title compound B, is obtained and identified by HNMR and mass spectral analyses. $^1$H NMR (DMSOd$_6$ 300 MHz) δ 1.22 (m, 6H), 2.95 (s, 3H), 3.95 (m, 4H), 6.6 (brs, 2H), 6.85 (d, 1H), 7.0 (m, 2H), 7.37-7.45 (m, 3H), 7.48 (d, 1H), 7.63 (s, 1H), 7.96 (m, 1H), 8.2 (d, 1H) MS m/e (M+H)$^+$ 449 $[α]_D^{25}$=−9.8 (c=1% in CH$_3$OH)

EXAMPLE 104

Preparation of 2-Amino-5-[3,4-bis-(2-fluoroethoxy)-phenyl]-5-[4-fluoro-3-(2-fluoro-pyridin-3-yl)-phenyl]-3-methyl-3,5-dihydro-imidazol-4-one

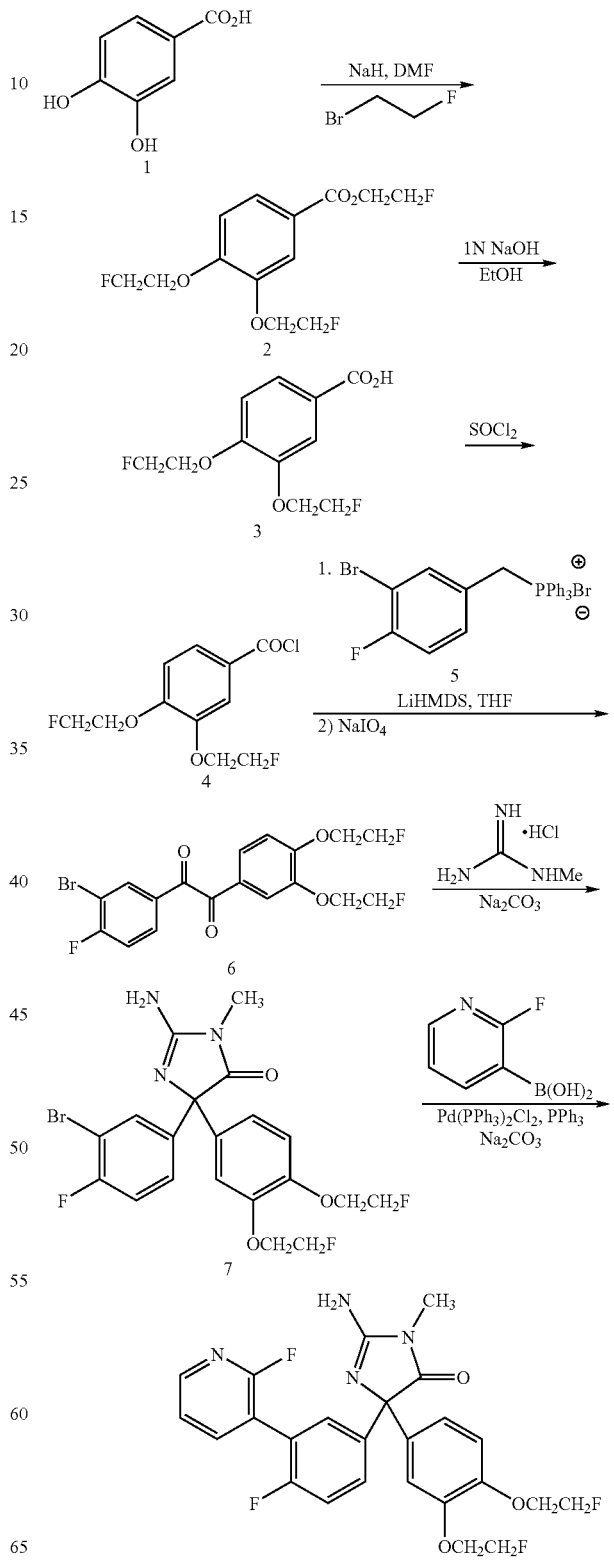

Step a) Preparation of Compound 2

Sodium hydride (1.82 g of a 60% dispersion in oil, 45.5 mmol) was washed with hexanes, suspended in DMF (5 mL) and treated dropwise with a solution of 1 (2.0 g, 13.0 mmol) in DMF (15 mL) over a period of 10 min at room temperature. After stirring for an additional 1.5 h at room temperature, the mixture was treated with a solution of 1-bromo-2-fluoro ethane in DMF (15 mL) and the mixture stirred at room temperature for 18 h, then heated at 60° C. for an additional 4 h. The mixture was cooled to room temperature and diluted with ethyl acetate (100 mL) and water (100 mL). The organic layer was separated and washed with 1 N NaOH (100 mL), 5% aqueous lithium chloride (2×100 mL), brine (100 mL), dried over magnesium sulfate, filtered and concentrated. Purification by flash chromatography (silica, 1:3 ethyl acetate/hexanes) afforded 2 (1.00 g, 26%) as a white solid: $^1$H NMR (300 MHz, CDCl$_3$) δ 7.74 (dd, J=8.4, 2.0 Hz, 1H), 7.63 (d, J=2.0 Hz, 1H), 6.94 (d, J=8.5 Hz, 1H), 4.84 (m, 2H), 4.75 (m, 3H), 4.67 (m, 1H), 4.58 (m, 1H), 4.52 (m, 1H), 4.36 (m, 2H), 4.30 (m, 2H); ESI MS m/z 293 [C$_{13}$H$_{15}$F$_3$O$_4$+H]$^+$.

Step b) Preparation of Compound 3

A mixture of 2 (1.00 g, 3.42 mmol) in ethanol (10 mL) and 1 N NaOH (10 mL) was heated at 75° C. for 1 h. The mixture was cooled to room temperature, concentrated, diluted with water (10 mL) and acidified with 6 N HCl. The solids that formed were collected by filtration and dried to afford 3 (0.76 g, 90%) as a white solid: $^1$H NMR (300 MHz, DMSO-d$_6$) δ 12.8 (br s, 1H), 7.58 (dd, J=8.4, 1.5 Hz, 1H), 7.50 (d, J=1.5 Hz, 1H), 7.11 (d, J=8.5 Hz, 1H), 4.84 (m, 2H). 4.67 (m, 2H), 4.39-4.22 (m, 4H).

Step c) Preparation of Compound 4

A mixture of 3 (0.76 g, 3.09 mmol), thionyl chloride (8 mL) and DMF (1 drop) was heated at reflux for 4 h. The mixture was then cooled to room temperature and concentrated. The residue was dissolved in toluene and again concentrated to afford 4 (0.82 g, 100%) as a white solid: $^1$H NMR (300 MHz, CDCl$_3$) δ 7.85 (dd, J=8.4, 1.8 Hz, 1H), 7.62 (d, J=2.1 Hz, 1H), 6.98 (d, J=8.7 Hz, 1H), 4.89 (m, 2H). 4.75 (m, 2H), 4.43-4.26 (m, 4H); IR (ATR) 1734, 1582, 1513, 1417 cm$^{-1}$.

Step d) Preparation of Compound 6

A 1.0 M solution of lithium bis(trimethylsilyl)amide in tetrahydrofuran (3.25 mL, 3.25 mmol) was added to a stirred suspension of (3-bromo-4-fluorobenzyl)triphenylphosphonium bromide (1.72 g, 3.25 mmol) in tetrahydrofuran (6 mL). The mixture was stirred for 25 min at room temperature, then cooled to −40° C., treated with a solution of 4 (0.82 g, 3.10 mmol) in tetrahydrofuran (3 mL) and stirred for an additional 2 h while slowly warming to room temperature. The reaction was then treated with water (5 mL) and sodium periodate (0.69 g, 3.25 mmol), then heated at 50° C. for 19 h. After this time the mixture was cooled to room temperature and diluted with ethyl acetate (25 mL). The organic layer was separated and washed with water (10 mL) and brine (10 mL), dried over magnesium sulfate, filtered and concentrated. Purification by flash chromatography (silica, 1:3 ethyl acetate/hexanes) afforded 6 (0.27 g, 20%) as a pale yellow solid: $^1$H NMR (300 MHz, CDCl$_3$) δ 8.22 (dd, J=6.5, 2.1 Hz, 1H), 7.92 (m, 1H), 7.63 (d, J=2.0 Hz), 7.51 (dd, J=8.4, 2.9 Hz, 1H), 7.23 (m, 1H), 7.96 (d, J=8.5 Hz, 1H) 4.85 (m, 2H), 4.76 (m, 2H), 4.39-4.31 (m, 4H).

Step e) Preparation of Compound 7

A mixture of 6 (0.26 g, 0.603 mmol) and 1-methylguanidine hydrochloride (0.30 g, 2.71 mmol) in dioxane (8 mL) and ethanol (5.3 mL) was stirred at room temperature for 5 min. A solution of sodium carbonate (0.29 g, 2.71 mmol) in water (2.3 mL) was then added and the mixture immersed into an 85° C. oil bath and stirred for 30 min. The reaction mixture was cooled to room temperature, concentrated and the residue partitioned between methylene chloride (50 mL) and water (20 mL). The organic layer was separated, washed with water (20 mL), brine (20 mL), dried over magnesium sulfate, filtered and concentrated. Purification by flash chromatography (silica, 95:5:0.5 methylene chloride/methanol/concentrated ammonium hydroxide) afforded 7 (0.154 g, 53%) as a white solid: $^1$H NMR (300 MHz, CDCl$_3$) δ 7.68 (m, 1H), 7.33 (m, 1H), 7.07 (m, 3H), 6.89 (m, 1H), 4.80 (m, 2H), 4.66 (m, 2H), 4.28 (m, 2H), 4.18 (m, 2H); ESI MS m/z 486 [C$_{20}$H$_{19}$BrF$_3$N$_3$O$_3$+H]$^+$.

Step f) Preparation of 2-amino-5-[3,4-bis-(2-fluoro-ethoxy)-phenyl]-5-[4-fluoro-3-(2-fluoro-pyridin-3-yl)-phenyl]-3-methyl-3,5-dihydro-imidazol-4-one A mixture of 7 (0.140 g, 0.288 mmol), 2-fluoropyridine-3-boronic acid (0.061 g, 0.430 mmol), sodium carbonate (0.092 g, 0.860 mmol), bis(triphenylphosphino)palladium (II)chloride (0.010 g, 0.014 mmol) and triphenylphosphine (0.008 g, 0.028 mmol) in 1:1 toluene/ethanol (8 mL) was degassed and heated at 110° C. for 1.5 h. The mixture was cooled to room temperature, concentrated and purified by flash chromatography (silica, 97:3:0.25 methylene chloride/methanol/concentrated ammonium hydroxide) to afford 8 (0.055 g, 39%) as a white solid, mp 85-95° C.; $^1$H NMR (300 MHz, CD$_3$OD) δ 8.23 (m, 1H), 7.93 (m, 1H), 7.51-7.38 (m, 3H), 7.21 (t, J=9.0 Hz, 1H), 6.98 (m, 3H), 4.78 (m, 2H), 4.68 (m, 2H), 4.62-4.58 (m, 4H), 3.11 (s, 3H); IR (ATR) 1733, 1666, 1502, 1260 cm$^{-1}$; ESI MS m/z 503 [C$_{25}$H$_{24}$F$_4$N$_4$O$_3$+H]$^+$. Anal. Calcd for C$_{25}$H$_{24}$F$_4$N$_4$O$_3$.0.25H$_2$O: C, 59.28; H, 4.45; N, 10.73. Found: C, 59.23; H, 4.47; N, 11.05.

EXAMPLE 105

Preparation of (5S)-2-Amino-5-[4-fluoro-3-(2-fluoropyridin-3-yl)phenyl]-5-(4-methoxy-3-methylphenyl)-3-methyl-3,5-dihydro-4H-imidazol-4-one [A] and (5R)-2-Amino-5-[4-fluoro-3-(2-fluoropyridin-3-yl)phenyl]-5-(4-methoxy-3-methylphenyl)-3-methyl-3,5-dihydro-4H-imidazol-4-one [B]

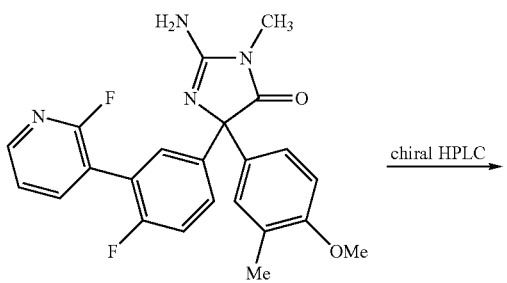

-continued

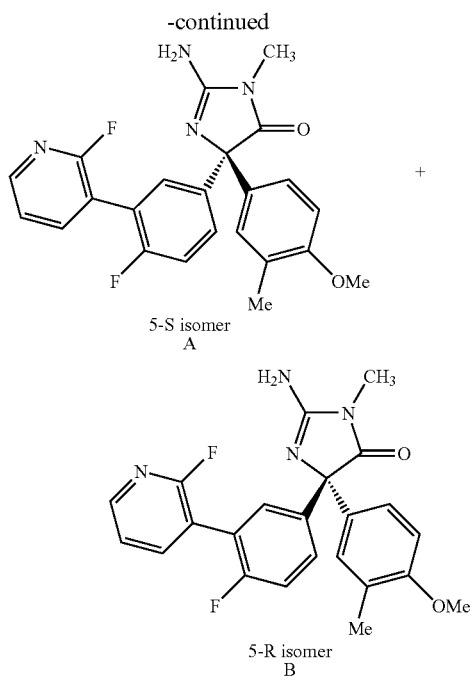

5-S isomer
A

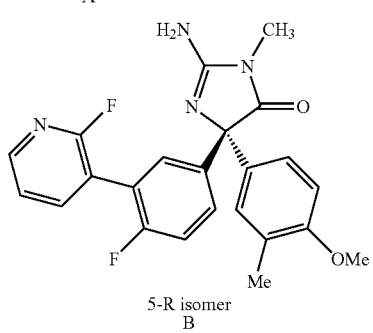

5-R isomer
B

The racemate 2-amino-5-[4-fluoro-3-(2-fluoropyridin-3-yl)phenyl]-5-(4-methoxy-3-methylphenyl)-3-methyl-3,5-dihydro-4H-imidazol-4-one was separated by HPLC using Chiralcel OJ, 2×25 cm, mobile phase 15% EtOH/DEA in hexane and a flow rate of 21 mL/min to give the title S isomer (A), $^1$H NMR (DMSOd$_6$ 300 MHz) δ 2.0 (s, 3H), 2.95 (s, 3H), 3.7 (s, 3H), 6.6 (b, 2H), 6.8 (d, 1H), 7.3 (m, 3H), 7.5 (m, 3H), 8.0 (m, 1H), 8.3 (m, 1H); MS m/e (M)$^+$ 423; [α]$_{25}$=+76.4 (C=1% in MeOH); mp 103-105° C. and the title R isomer (B), $^1$H NMR (DMSOd$_6$ 300 MHz) δ 2.0 (s, 3H), 2.95 (s, 3H), 3.7 (s, 3H), 6.6 (b, 2H), 6.8 (d, 1H), 7.3 (m, 3H), 7.5 (m, 3H), 8.0 (m, 1H), 8.3 (m, 1H); MS m/e (M)$^+$ 423; [α]$_{25}$=−40.8 (C=1% in MeOH); mp 103-105° C.

EXAMPLE 106

Preparation of (5S) 2-Amino-5-(4-fluoro-3-pyrimidin-5-ylphenyl)-5-(4-methoxy-3-methylphenyl)-3-methyl-3,5-dihydro-4H-imidazol-4-one [A] and (5R)-2-Amino-5-(4-fluoro-3-pyrimidin-5-ylphenyl)-5-(4-methoxy-3-methylphenyl)-3-methyl-3,5-dihydro-4H-imidazol-4-one [B]

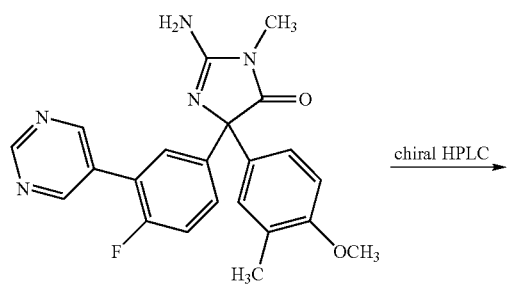

chiral HPLC →

-continued

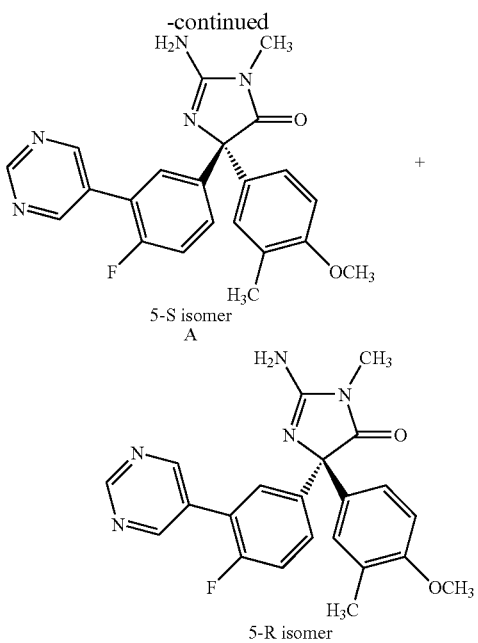

5-S isomer
A

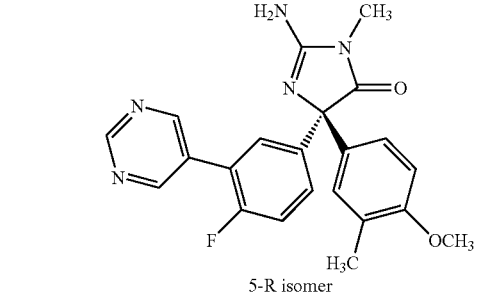

5-R isomer
B

The racemate 2-amino-5-(4-fluoro-3-pyrimidin-5-ylphenyl)-5-(4-methoxy-3-methylphenyl)-3-methyl-3,5-dihydro-4H-imidazol-4-one was separated by HPLC using Chiralcel OD, 2×25 cm, mobile phase cm using mobile phase MeOH (30% with 0.1% DEA) in CO$_2$ (100 bar) and a flow rate of 50 mL/min to give the title S isomer (A), $^1$H NMR (400 MHZ, DMSO-d$_6$) δ 2.04 (s, 3H), 2.93 (s, 3H), 3.69 (s, 3H), 6.61 (bs, 2H), 6.81 (m, 1H), 7.22 (m, 1H), 7.27 (m, 1H), 7.29 (m, 1H), 7.60 (m, 1H), 7.61 (m, 1H), 8.89 (d, 2H), 9.18 (d, 1H); MS m/e (M+H)$^+$ 406; mp 115° C.; [α]$_{25}$=48 (C=1% in MeOH); and the title R isomer (B), $^1$H NMR (400 MHZ, DMSO-d$_6$) δ 2.04 (s, 3H), 2.93 (s, 3H), 3.69 (s, 3H), 6.60 (bs, 2H), 6.81 (m, 1H), 7.22 (m, 1H), 7.27 (m, 1H), 7.29 (m, 1H), 7.60 (m, 1H), 7.61 (m, 1H), 8.89 (d, 2H), 9.18 (d, 1H); MS m/e (M+H)$^+$ 406; mp 115° C.; [α]$_{25}$=−39.2 (C=1% in MeOH).

EXAMPLE 107

Preparation of (5S)-2-Amino-5-(4-fluoro-3-pyrimidin-5-ylphenyl)-5-[4-methoxy-3-(trifluoromethyl)phenyl]-3-methyl-3,5-dihydro-4H-imidazol-4-one [A] and (5R)-2-Amino-5-(4-fluoro-3-pyrimidin-5-ylphenyl)-5-[4-methoxy-3-(trifluoromethyl)phenyl]-3-methyl-3,5-dihydro-4H-imidazol-4-one [B]

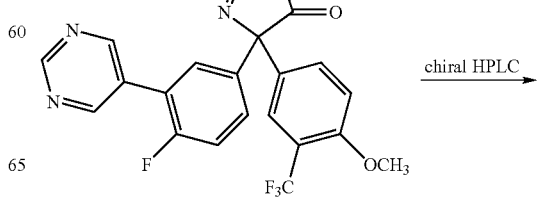

chiral HPLC →

-continued

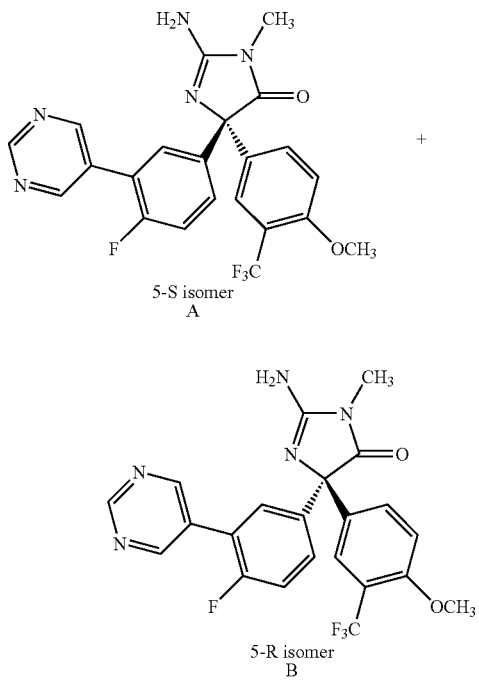

5-S isomer
A

+

5-R isomer
B

A racemic mixture of 2-amino-5-(4-fluoro-3-pyrimidin-5-ylphenyl)-5-[4-methoxy-3-(trifluoromethyl)phenyl]-3-methyl-3,5-dihydro-4H-imidazol-4-one was separated by HPLC using Chiralcel OD, 2×25 cm, mobile phase cm, mobile phase EtOH/Hexane (15/85) and a flow rate of 20 mL/min to give the title S isomer (A), $^1$H NMR (400 MHZ, DMSO-$d_6$) δ 2.94 (s, 3H), 3.81 (s, 3H), 6.76 (bs, 2H), 7.19 (m, 1H), 7.32 (m, 1H), 7.32 (m, 1H), 7.50 (m, 1H), 7.70 (m, 2H), 8.89 (d, 2H), 9.18 (d, 1H); MS m/e (M+H)$^+$ 460.1; mp 100° C.; $[\alpha]_{25}$=1.6 (C=1% in MeOH); and the title R isomer (B), $^1$H NMR (400 MHZ, DMSO-$d_6$) δ 2.94 (s, 3H), 3.81 (s, 3H), 6.76 (bs, 2H), 6.82 (m, 1H), 7.22 (m, 1H), 7.32 (m, 1H), 7.50 (m, 1H), 7.59 (m, 1H), 7.70 (m, 1H), 8.89 (d, 2H), 9.18 (d, 1H); MS m/e (M–H)$^-$ 458; mp 100° C.; $[\alpha]_{25}$=–1.8 (C=1% in MeOH).

EXAMPLE 108

Preparation of 2-Amino-5-[4-(2-fluoroethoxy)phenyl]-5-[4-fluoro-3-(2-fluoropyridin-3-yl)phenyl]-3-methyl-3,5-dihydro-4H-imidazol-4-one

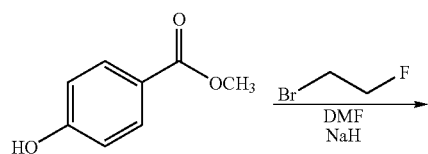

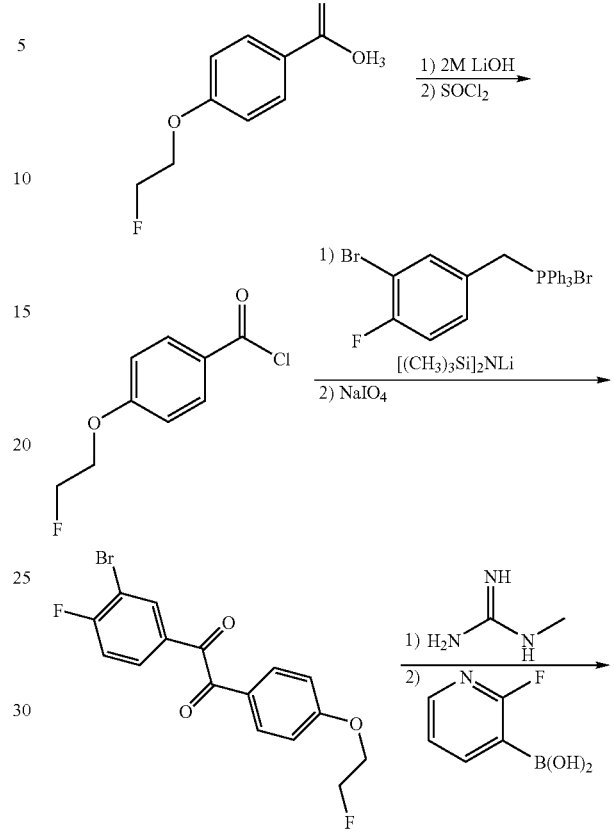

Step a) Preparation of Methyl 4-(2-fluoroethoxy)benzoate

Under nitrogen atmosphere to a cold (5° C.) solution of 4-hydroxy-benzoic acid methyl ester (7 g, 46 mmol) in DMF (30 ml) was added NaH (60%; 2.2 g) portion wise over 20 minutes. After the addition was completed, the ice bath was removed and the resulting white suspension was heated up to room temperature and stirred for 3 hours. A prepared solution of 1-Bromo-2-fluoro-ethane (6.42 g, 50 56 mmol) in DMF (20 mL) was added and the new mixture was stirred at 50° C. for 18 hours. After cooling to room temperature the mixture was poured into a mixture of ice and 1 N HCl (1:1) and extracted with ethyl acetate. The organic extracts were washed with brine, dried over MgSO$_4$. Evaporation and purification by flash chromatography (hexane/ethyl acetate 9/1) gave a white solid (7.75. 85% yield); $^1$H NMR (400 MHZ, CDCl$_3$) δ 3.86 (s, 3H), 4.20 (m, 1H), 4.21 (m, 1H), 4.27 (m, 1H), 4.28 (m, 1H), 6.93 (d, 2H), 7.98 (d, 2H); MS m/e (M+H)$^+$ 198; mp 77° C.

Step b) Preparation of 4-(2-Fluoroethoxy)benzoic acid

To a solution of methyl 4-(2-fluoroethoxy)benzoate (7.7 g, 38.85 mmol) in dioxane (100 mL) was added LiOH (2M, 39 mL). The reaction mixture was stirred at room temperature for 18 hours, and then concentrated in vacuo. The residue was dissolved in H$_2$O (30 ml) and extracted with ether. Under cooling the aqueous was acidified with HCl (6N) and extracted with CHCl$_3$. The organic extracts were dried over MgSO$_4$. Evaporation and recrystallzation from ethyl acetate and methylene chloride gave the title compound as a white solid (5 g, 71% yield); $^1$H NMR (400 MHZ, DMSO-d$_6$) δ 4.28 (m, 1H), 4.35 (m, 1H,) 4.68 (m, 1H), 4.80 (m, 1H), 7.04 (d, 2H), 7.89 (d, 2H); MS m/e (M–H)$^-$ 183.1; mp 203° C.

Step c) Preparation of 1-(3-bromo-4-fluorophenyl)-2-[4-(2-fluoroethoxy)-phenyl]ethane-1,2-dione A 1.0 M solution of lithium bis(trimethylsilyl)amide in tetrahydrofuran (20 mL, 20 mmol was added at room temperature to a stirred suspension of (3-bromo-4-fluoro-benzyl)triphenylphosphonium bromide (10.6 g, 20 mmol) in tetrahydrofuran (40 mL). The mixture was stirred for 40 minutes, then cooled to –20° C. and treated with 4-(2-fluoroethoxy)benzoyl chloride (4.1 g, 20 mmol) in tetrahydrofuran (40 mL) and stirred for an additional 2 hours while slowly warming to room temperature. The mixture was treated with water (20 mL) and sodium periodate (4.3 g, 20 mmol) then stirred at 50° C. for 18 hours. After cooling to room temperature the mixture was extracted with ethyl acetate. The organic extracts were washed with brine, dried over MgSO$_4$. Evaporation and purification by flash chromatography (hexane/ethyl acetate 9/1) gave a yellow solid (3 g, 41% yield); $^1$H NMR (400 MHZ, CDCl$_3$) δ 4.25 (m, 1H), 4.32 (m, 1H,) 4.70 (m, 1H), 4.82 (m, 1H), 7.01 (d, 2H), 7.23 (m, 1H), 7.94 (m, 3H), 8.22 (m, 1H); MS m/e (M+CH$_3$COO)$^-$ 427; mp 107° C.

Step d) Preparation of 2-Amino-5-[4-(2-fluoroethoxy)phenyl]-5-[4-fluoro-3-(2-fluoropyri-din-3-yl)phenyl]-3-methyl-3,5-dihydro-4H-imidazol-4-one Using essentially the same procedure described in Examples 39 and 40 and employing methylaminoguanidine and 2-fluoropyridine-3-boronic acid, respectively, the title product was obtained as a white solid, mp 135° C., $^1$H NMR (400 MHZ, DMSO-d$_6$) δ2.93(s, 3H), 4.09 (m, 1H), 4.11 (m, 1H,) 4.59 (m, 1H), 4.61 (m, 1H), 6.84, (bs, 2H), 6.86 (m, 2H), 7.30 (m, 3H), 7.44 (m, 1H), 7.52 (m, 2H), 7.95 (m, 1H), 8.26 (m, 1H); MS m/e (M–H)$^-$ 439.2;

EXAMPLES 109-124

Preparation of 2-Amino-5-alkoxyphenyl-5-(3-heteroaryl)phenyl-3-methyl-3,5-dihydro-4H-imidazol-4-one Compounds

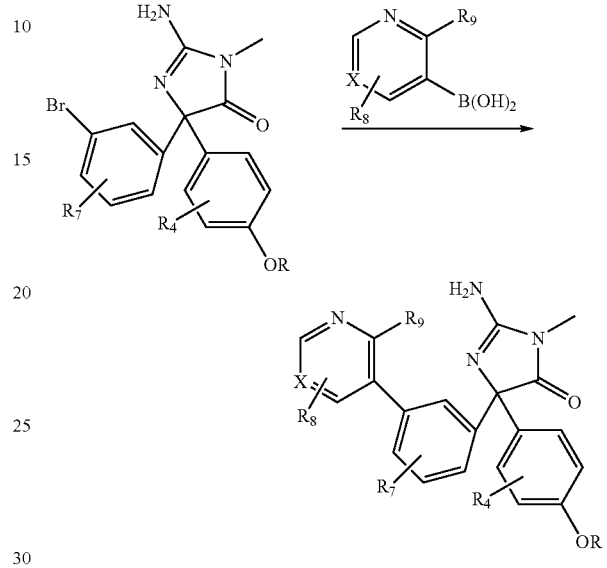

Using essentially the same procedure described in Example 108 and employing the appropriate boronic acid and 5-(3-bromopheny)hydantoin substrate, the compounds shown on Table III were obtained and identified by NMR and mass spectral analyses.

TABLE III

| Ex. No | R$_4$ | R | R$_7$ | R$_8$ | R$_9$ | X | mp ° C. |
|---|---|---|---|---|---|---|---|
| 109 | H | CH$_2$CH$_2$F | 4-F | H | H | N | 123 |
| 110 | H | CH$_2$CH$_2$F | H | H | H | CF | — |
| 111 | H | CH$_2$CH$_2$F | H | 6-F | H | CH | 100 |
| 112 | 3-CH$_3$ | CH$_2$CH$_2$F | 4-F | H | F | CH | 105-106 |
| 113 | 3-CH$_3$ | CH$_2$CH$_2$F | 4-F | H | H | N | 108-110 |
| 114 | 3-CH$_3$ | CH$_2$C$_6$H$_5$ | H | H | H | N | 107-109 |
| 115 | 3-CH$_3$ | H | H | H | H | N | 168-170 |
| 116 | 3-CH$_3$ | CH$_2$CH$_2$F | H | H | H | N | 108-110 |
| 117 | 3-CH$_3$ | CH$_2$CN | H | H | H | N | 220-222 |
| 118 | 3-CH$_3$ | i-propyl | H | H | H | N | 101-103 |
| 119 | 3-CH$_3$ | CH$_2$CO$_2$C$_2$H$_5$ | H | H | H | N | 105-107 |
| 120 | 3-CH$_3$ | C$_2$H$_5$ | H | H | H | N | 106-108 |
| 121 | 3-CH$_3$ | n-propyl | H | H | H | N | 102-104 |
| 122 | 3-CH$_3$ | i-butyl | H | H | H | N | 103-105 |
| 123 | 3-CH$_3$ | CH$_2$CH$_2$cyclohexyl | H | H | H | N | 107-109 |
| 124 | 3-CH$_3$ | n-C$_3$H$_6$—OC$_6$H$_5$ | H | H | H | N | 72-74 |

EXAMPLE 125

Preparation of 2-Amino-5-(3-bromo-4-fluorophenyl)-3-(2-fluoroethyl)-5-(4-trifluoromethoxy-phenyl)-3,5-dihydro-imidazol-4-one

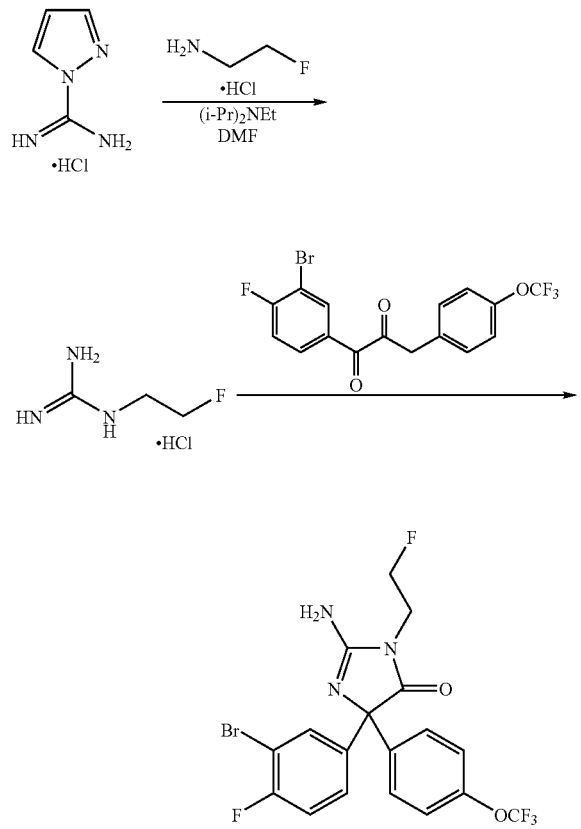

To a stirred mixture of 2-fluoroethylamine hydrochloride (1.50 g; 15.1 mmol) and 1H-pyrazole-1-carboxamidine hydrochloride (1.77 g; 12.1 mmol) in DMF was added diisopropylethylamine (3.58 g; 27.7 mmol). The mixture was stirred under nitrogen atmosphere for 3 hours. Diethyl ether was added (35 mL) and the mixture was shaken and the oily product was allowed to settle to the bottom of the flask, whereupon the ether was decanted. This was repeated and the clear oil was dried under high vacuum at ambient temperature for 24 hours. The N-(2-fluoroethyl)-guanidine product was used without further purification (1.6 g).

A solution of 1-(3-bromo-4-fluoro-phenyl)-2-(4-trifluoromethoxy-phenyl)-ethane-1,2-dione (0.181 g; 0.46 mmol) and N-(2-fluoroethyl)-guanidine (0.105 g; 0.74 mmol) in a mixture of dioxane, water and ethanol, was treated with solid sodium carbonate heated at 90° C. for five hours, and evaporated to dryness. The resultant residue is dissolved in chloroform, washed with water, dried over sodium sulfate, and evaporated to give the title compound as a light-green solid, 116 mg (52% yield), MS (API-ES) 480.3 [M+H]+.

EXAMPLES 126-128

Preparation of 2-Amino-3-substituted-5-(3-heteroaryl)phenyl-5-(4-trifluoromethoxy-phenyl)-3,5-dihydro-imidazol-4-one Compounds

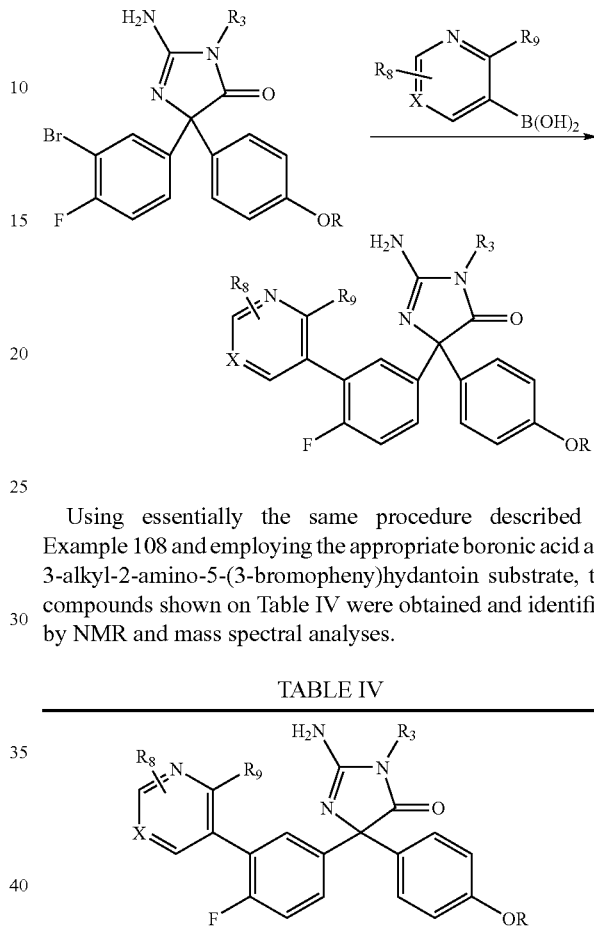

Using essentially the same procedure described in Example 108 and employing the appropriate boronic acid and 3-alkyl-2-amino-5-(3-bromopheny)hydantoin substrate, the compounds shown on Table IV were obtained and identified by NMR and mass spectral analyses.

TABLE IV

| Ex. No | R | R3 | R8 | R9 | X | mp °C. |
|---|---|---|---|---|---|---|
| 126 | $CF_3$ | $CH_2CH_2F$ | H | H | N | 166-170 |
| 127 | $CF_3$ | $CH_2CH_2F$ | H | F | CH | 138-150 |
| 128 | $CHF_2$ | $C_2H_5$ | H | H | C—F | |

EXAMPLE 129

Preparation of 3-Methyl-5-(3-methyl-4-ropoxyphenyl)-2-(propylamino)-5-(3-pyrimidin-5-ylphenyl)-3,5-dihydro-4H-imidazol-4-one

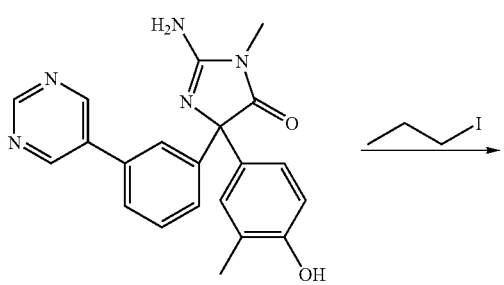

-continued

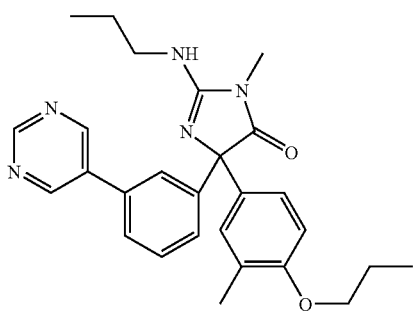

A solution of 2-amino-5-(4-hydroxy-3-methylphenyl)-3-methyl-5-(3-pyrimidin-5-ylphenyl)-3,5-dihydro-4H-imidazol-4-one (74.6 mg, 0.2 mmol) in N,N-dimethylformamide was treated with 2-iodopropane (31.2 mg, 0.4 mmol) and Cs$_2$CO$_3$ (130 mg, 0.4 mmol) at room temperature, stirred overnight at room temperature and quenched with H$_2$O. The phases were separated, the aqueous phase was extracted with ethyl acetate. The organic phase was combined with the extracts, washed sequentially with H$_2$O and brine, dried over MgSO$_4$ and evaporated to dryness. The resultant residue was purified by flash chromatography with ethyl acetate/ethanol (2M ammonia) (90/10) as eluent to afford the title compound as a white solid, 60 mg (65% yield), mp 64-66° C.; MS (+) ES: 458 (M+H)$^+$.

EXAMPLE 130

Preparation of 4-iodo-2-methyl-1-[(1R)-1-phenylethoxy]benzene

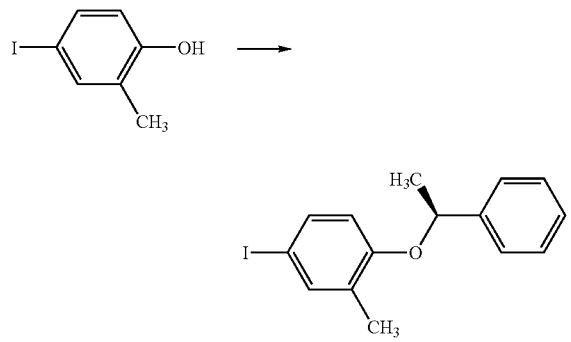

A cooled solution of PPh$_3$ (262 mg 10 mmol) in THF was treated with diethyl azodicarboxylate (1.74 g, 10 mmol) at 0° C., stirred for 5 min, allowed to warm-up to room temperature, treated with 4-iodo-2-methylphenol (1.17 g, 5 mmol) and R(+)-1-phenylethanol (1.22 g, 10 mmol), stirred for 24 h at room temperature and concentrated in vacuo. The resultant residue was purified by flash chromatography (silica gel, 100% hexane) to afford the title compound as a clear oil 2.5 g (50%). MS (+): EI 338 M$^+$.

EXAMPLE 131

Preparation of 2-amino-3-methyl-5-{3-methyl-4-[(1R)-1-phenylethoxy]phenyl}-5-(3-pyrimidin-5-ylphenyl)-3,5-dihydro-4H-imidazol-4-one

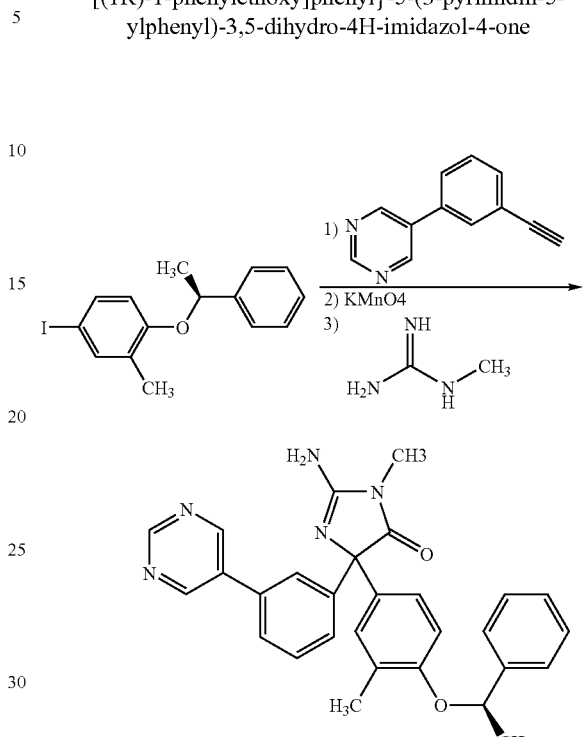

A solution of 4-iodo-2-methyl-1-[(1R)-1-phenylethoxy]benzene (10 mmol) in triethylamine is treated with tetrakis (triphenylphosphine)Pd (0.69 mmol), copper iodide (0.97 mmol) and a solution of 3-(primidin-5-yl)ethynlybenzene (10 mmol) in acetonitrile at room temperature. The reaction mixture is heated for 1 h at 80° C., cooled and concentrated in vacuo. The resultant residue is purified by chromotography to give 5-[3-({3-methyl-4-[(1R)-1-phenyl}ethynyl)phenyl]pyrimidine as an oil, MS (+) ES: 391 (M+H)$^+$. A solution of 5-[3-({3-methyl-4-[(1R)-1-phenyl}ethynyl)phenyl]pyrimidine (8.3 mmol) in acetone is treated with a warm (~40° C.) solution of NaHCO$_3$ (4.98 mmol) and MgSO$_4$ (12.45 mmol) in water (80 mmol) followed by a single portion of solid KMnO$_4$ (8.3 mmol), stirred for 40 min. at room temperature and extracted with 1:1 ether:hexane. The extracts are combined, dried over MgSO$_4$ and concentrated to dryness to give 1-{3-methyl-4-[(1R)-1-phenylethoxy]phenyl}-2-(3-pyrimidin-5-ylphenyl)ethane-1,2-dione as a foam, MS (+) ES: 423 (M+H)$^+$. A solution of 1-{3-methyl-4-[(1R)-1-phenylethoxy] phenyl}-2-(3-pyrimidin-5-ylphenyl)ethane-1,2-dione (5.0 mmol) in ethanol is treated with N-methylguanidine hydrochloride (5.5 mmol) and an aqueous solution of Na$_2$CO$_3$ (10.0 mmol), heated at reflux temperature for 1 h and concentrated in vacuo. The resultant residue is purified by chromatography to afford the title product as a white solid, mp 112-114° C. MS (+) ES: 478 (M+H)$^+$.

EXAMPLE 132

Preparation of (5R)-2-Amino-5-[3-(2-fluoropyridin-3-yl)phenyl]-3-methyl-5-[4-(trifluoromethoxy)phenyl]-3,5-dihydro-4H-imidazol-4-one

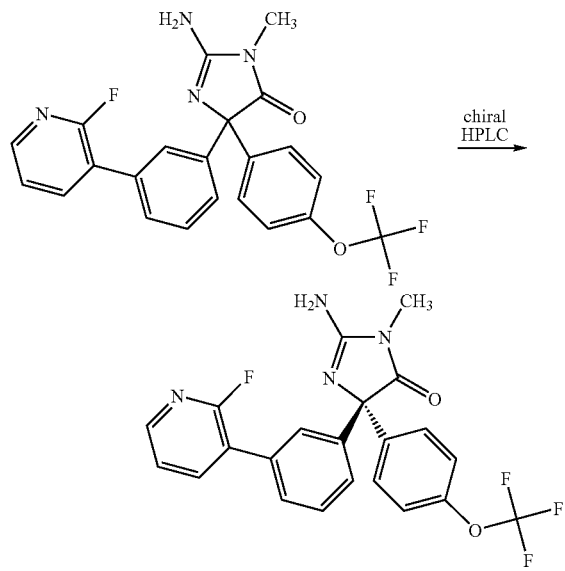

A racemic mixture of 2-amino-5-[3-(2-fluoropyridin-3-yl)phenyl]-3-methyl-5-[4-(trifluoromethoxy)phenyl]-3,5-dihydro-4H-imidazol-4-one was separated by chiral HPLC using Chiralcel AD, 2×25 cm (column) with mobile phase 9% EtOH in hexanes (0.1% diethylamine) to give the title R-isomer: $[\alpha]_{25}$=−13.4 (1% in MeOH); $^1$H NMR (DMSOd$_6$ 300 MHz) δ 2.95 (s, 3H), 6.65 (brs, 2H), 7.28 (d, 2H), 7.4-7.45 (m, 3H), 7.5 (m, 1H), 7.55 (d, 2H), 7.65 (d, 1H), 7.95-8.0 (m, 1H), 8.2 (m, 1H); MS m/e (M+H)$^+$ 445.

EXAMPLE 133

Preparation of (5S)-2-Amino-5-[4-(difluoromethoxy)phenyl]-5-[4-fluoro-3-(2-fluoropyridin-3-yl)phenyl]-3-methyl-3,5-dihydro-4H-imidazol-4-one [A] and (5R)-2-Amino-5-[4-(difluoromethoxy)phenyl]-5-[4-fluoro-3-(2-fluoropyridin-3-yl)phenyl]-3-methyl-3,5-dihydro-4H-imidazol-4-one [B]

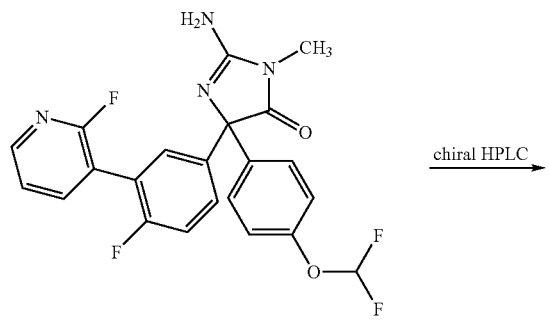

-continued

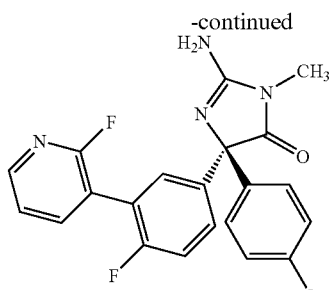

5-S isomer
A

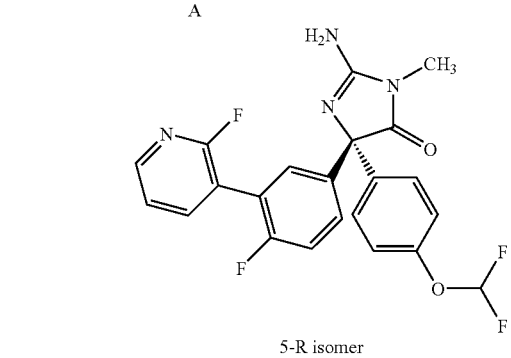

5-R isomer
B

A racemic mixture of 2-amino-5-[4-(difluoromethoxy)phenyl]-5-[4-fluoro-3-(2-fluoropyridin-3-yl)phenyl]-3-methyl-3,5-dihydro-4H-imidazol-4-one was separated by chiral HPLC: Chiralcel AD, 2×25 cm (column) with mobile phase 9% EtOH in hexanes/TFA to give the the title product A, $[\alpha]_{25}$=+11.4 (1% in MeOH); $^1$H NMR (DMSOd$_6$ 300 MHz) δ 3.12 (s, 3H), 7.25 (m, 3H), 7.4-7.5 (m, 4H), 7.5 (m, 2H), 8.0 (m, 1H), 8.6 (m, 1H), 9.5-9.7 (br, 2H); MS m/e (M+H)$^+$ 445 and the title product B, $[\alpha]_{25}$=−10.4 (1% in MeOH); $^1$H NMR (DMSOd$_6$ 300 MHz) δ 3.12 (s, 3H), 7.25 (m, 3H), 7.4-7.5 (m, 4H), 7.5 (m, 2H), 8.0 (m, 1H), 8.6 (m, 1H), 9.5-9.7 (br, 2H); MS m/e (M+H)$^+$ 445.

EXAMPLE 134

Preparation of (5S)-2-Amino-5-[4-(difluoromethoxy)phenyl]-5-[4-fluoro-3-(6-fluoropyridin-3-yl)phenyl]-3-methyl-3,5-dihydro-4H-imidazol-4-one [A] and (5R)-2-Amino-5-[4-(difluoromethoxy)phenyl]-5-[4-fluoro-3-(6-fluoropyridin-3-yl)phenyl]-3-methyl-3,5dihydro-4H-imidazol-4-one [B]

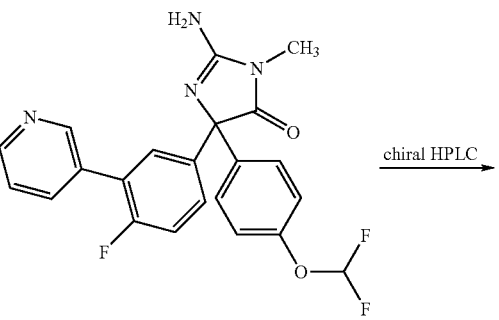

-continued

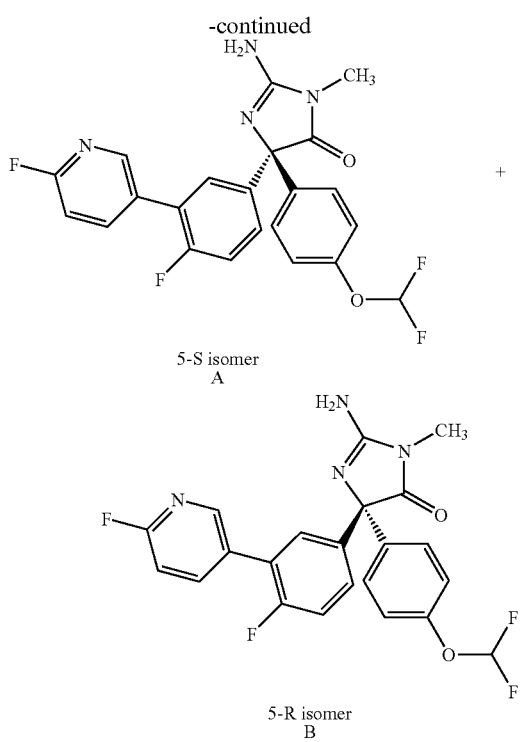

5-S isomer
A

5-R isomer
B

A racemic mixture of 2-amino-5-[4-(difluoromethoxy) phenyl]-5-[4-fluoro-3-(6-fluoropyridin-3-yl)phenyl]-3-methyl-3,5-dihydro-4H-imidazol-4-one was separated by chiral HPLC: Chiralcel OJ, 0.46×10 cm (column) with mobile phase 15% EtOH in hexanes to give the title S-isomer (A): $[\alpha]_{25}$=+6 (1% in MeOH); $^1$H NMR (DMSOd$_6$ 300 MHz) δ 2.94 (s, 3H), 6.8 (brs, 2H), 7.08 (d, 2H), 7.12 (t, 1H), 7.28 (m, 2H), 7.4-7.5 (m, 3H), 7.6 (dd, 1H), 8.05 (m, 1H), 8.3 (s, 1H); MS m/e (M+H)$^+$ 445 and the title R-isomer (B): $[\alpha]_{25}$=−7.4 (1% in MeOH); $^1$H NMR (DMSOd$_6$ 300 MHz) δ 2.94 (s, 3H), 6.8 (brs, 2H), 7.08 (d, 2H), 7.12 (t, 1H), 7.28 (m, 2H), 7.45 (d, 2H), 7.4-7.5 (m, 1H), 7.6 (dd, 1H), 8.05 (m, 1H), 8.3 (s, 1H); MS m/e (M+H)$^+$ 445.

EXAMPLE 135

Preparation of (5S)-2-Amino-5-[4-(difluoromethoxy) phenyl]-5-[3-(6-fluoropyridin-3-yl)phenyl]-3-methyl-3,5-dihydro-4H-imidazol-4-one [A] and (5R)-2-Amino-5-[4-(difluoromethoxy)phenyl]-5-[3-(6-fluoropyridin-3-yl)phenyl]-3-methyl-3,5-dihydro-4H-imidazol-4-one [B]

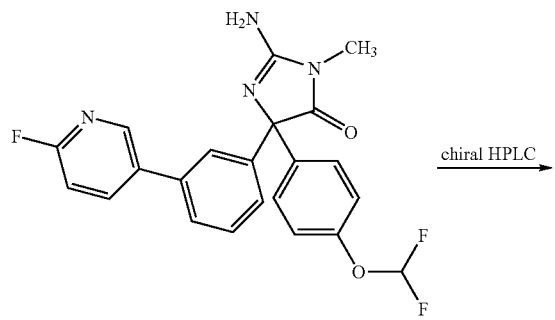
chiral HPLC

-continued

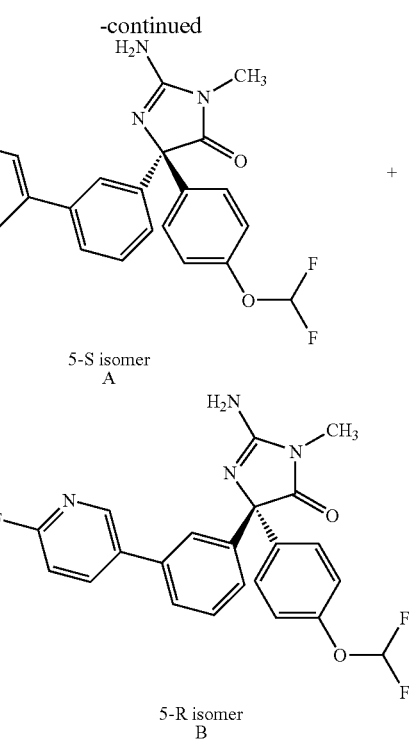

5-S isomer
A

5-R isomer
B

A racemic mixture of 2-Amino-5-[4-(difluoromethoxy) phenyl]-5-[3-(6-fluoropyridin-3-yl)phenyl]-3-methyl-3,5-dihydro-4H-imidazol-4-one was separated by chiral HPLC: Chiralcel OJ, 0.46×10 cm (column) with mobile phase 15% EtOH in hexanes to give the title S-isomer (A): $[\alpha]_{25}$=−7.4 (1% in MeOH); $^1$H NMR (DMSOd$_6$ 300 MHz) δ 2.95 (s, 3H), 6.7 (brs, 2H), 7.08 (d, 2H), 7.12 (t, 1H), 7.25 (dd, 1H), 7.4 (t, 1H), 7.5-7.55 (m, 4H), 7.7 (s, 1H), 8.2 (m, 1H), 8.37 (s, 1H); MS m/e (M+H)$^+$ 427; and the title R-isomer (B): $[\alpha]_{25}$=+8.4 (1% in MeOH); $^1$H NMR (DMSOd$_6$ 300 MHz) δ 2.95 (s, 3H), 6.7 (brs, 2H), 7.08 (d, 2H), 7.12 (t, 1H), 7.25 (dd, 1H), 7.4 (t, 1H), 7.5-7.55 (m, 4H), 7.7 (s, 1H), 8.2 (m, 1H), 8.37 (s, 1H); MS m/e (M+H)$^+$ 427.

EXAMPLE 136

Preparation of (5S)-2-Amino-5-(3,4-diethoxyphenyl)-5-[4-fluoro-3-(2-fluoropyridin-3-yl)phenyl]-3-methyl-3,5-dihydro-4H-imidazol-4-one [A] and (5R)-2-Amino-5-(3,4-diethoxyphenyl)-5-[4-fluoro-3-(2-fluoropyridin-3-yl)phenyl]-3-methyl-3,5-dihydro-4H-imidazol-4-one [B]

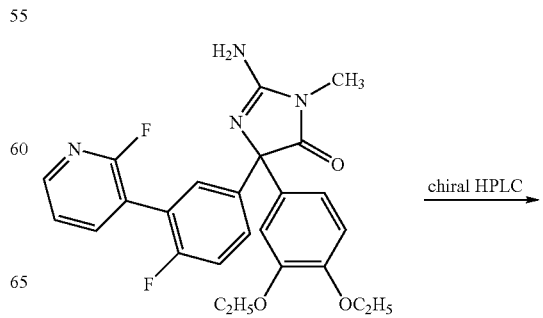
chiral HPLC

-continued

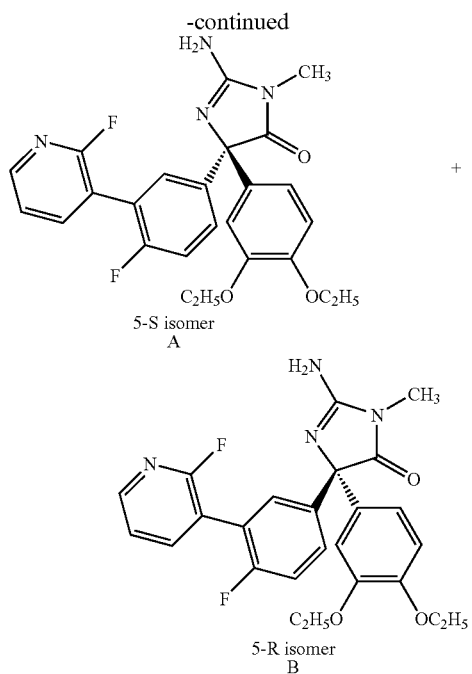

5-S isomer
A

5-R isomer
B

A racemic mixture of 2-amino-5-(3,4-diethoxyphenyl)-5-[4-fluoro-3-(2-fluoropyridin-3-yl)phenyl]-3-methyl-3,5-dihydro-4H-imidazol-4-one was separated using a WhelkO, 2×25 cm chiral HPLC column and 20% EtOH in heptane with 1% triethylamine, as the eluent to give the title S-isomer (A) as a white solid, $[\alpha]_{25}$=−22.2, 1% in methanol; $^1$H NMR (DMSOd$_6$ 300 MHz) δ 1.3 (t, 6H), 2.9 (s, 3H), 3.9 (dxq, 4H), 6.6 (b, 2H), 6.8 (d, 1H) 7.0 (m, 2H), 7.3 (t, 1H), 7.5 (m, 3H), 7.9 (s, 1H), 8.3 (m, 1H); MS m/e (M)$^+$ 467; and the title R-isomer (B) as a white solid, $[\alpha]_{25}$=+26.0, 1% in methanol; $^1$H NMR (DMSOd$_6$ 300 MHz) δ 1.3 (t, 6H), 2.9 (s, 3H), 3.9 (dxq, 4H), 6.6 (b, 2H), 6.8 (d, 1H) 7.0 (m, 2H), 7.3 (t, 1H), 7.5 (m, 3H), 7.9 (s, 1H), 8.3 (m, 1H); MS m/e (M)$^+$ 467.

EXAMPLE 137

Preparation of (5S)-2-Amino-5-[4-(difluoromethoxy)phenyl]-5-[3-(2.5-difluoropyridin-3-yl)phenyl]-3-methyl-3,5-dihydro-4H-imidazol-4-one [A] and (5R)-2-Amino-5-[4-(difluoromethoxy)phenyl-]5-[3-(2,5-difluoropyridin-3-yl)phenyl]-3-methyl-3,5-dihydro-4H-imidazol-4-one [B]

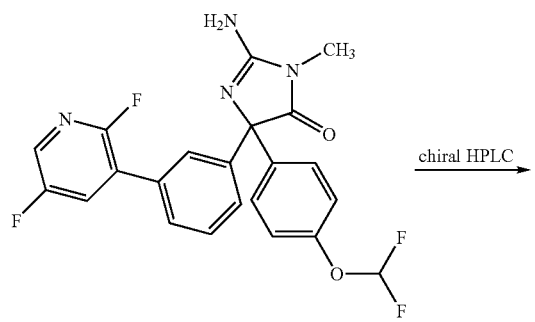

→ chiral HPLC

-continued

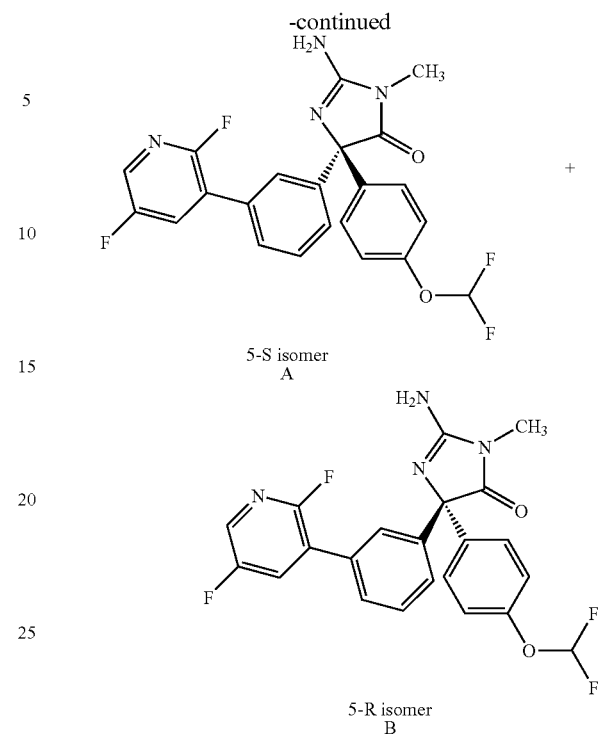

5-S isomer
A

5-R isomer
B

A racemic mixture of 2-amino-5-[4-(difluoromethoxy)phenyl]-5-[3-(2,5-difluoropyridin-3-yl)phenyl]-3-methyl-3,5-dihydro-4H-imidazol-4-one was separated by chiral HPLC: Chiralcel OJ, 2×25 cm (column) with mobile phase 35% EtOH in hexanes/DEA to give the title S-isomer (A): $[\alpha]_{25}$=+2.8 (1% in MeOH); $^1$H NMR (DMSOd$_6$ 300 MHz) δ 2.94 (s, 3H), 6.7 (brs, 2H), 7.08 (d, 2H), 7.12 (t, 1H), 7.4-7.5 (m, 5H), 7.7 (s, 1H), 8.0 (m, 1H), 8.2 (m, 1H); MS m/e (M+H)$^+$ 445; and the title R-isomer (B): $[\alpha]_{25}$=+2.8 (1% in MeOH); $^1$H NMR (DMSOd$_6$ 300 MHz) δ 2.94 (s, 3H), 6.7 (brs, 2H), 7.08 (d, 2H), 7.12 (t, 1H), 7.4-7.5 (m, 5H), 7.7 (s, 1H), 8.0 (m, 1H), 8.2 (m, 1H); MS m/e (M+H)$^+$ 445.

EXAMPLE 138

Preparation of (5S)-2-Amino-5-[4-(2-fluoroethoxy)-3-methylphenyl]-3-methyl-5-(3-pyrimidin-5-ylphenyl)-3,5-dihydro-4H-imidazol-4-one [A] and (5R)-2-Amino-5-[4-(2-fluoroethoxy)-3-methylphenyl]-3-methyl-5-(3-pyrimidin-5-ylphenyl)-3,5-dihydro-4H-imidazol-4-one [B]

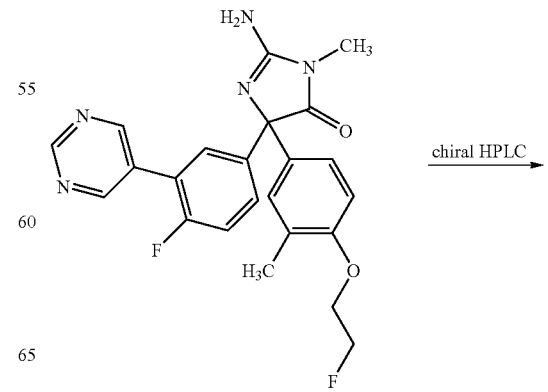

→ chiral HPLC

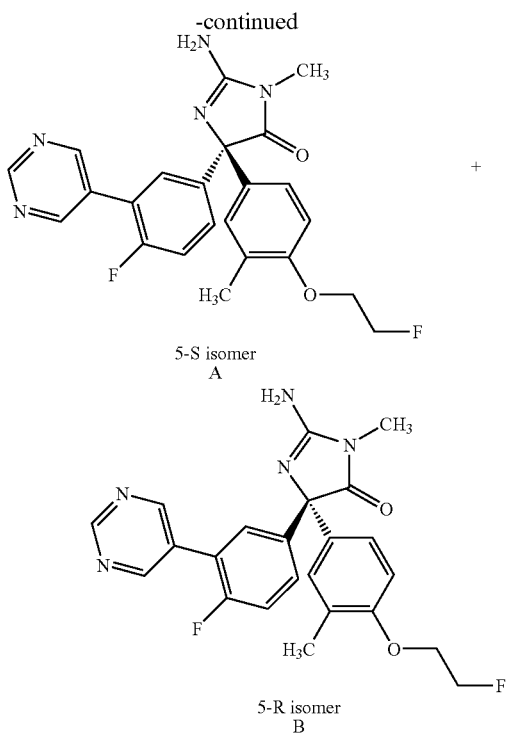

5-S isomer
A

5-R isomer
B

Using essentially the same procedure described in Examples 133-137 and employing a racemic mixture of 2-amino-5-[4-(2-fluoroethoxy)-3-methylphenyl]-3-methyl-5-(3-pyrimidin-5-ylphenyl)-3,5-dihydro-4H-imidazol-4-one, the title S-isomer (A) was obtained as a white solid, mp 116-118° C.; $[\alpha]_{25}=-31.46$ (1% in DMSO); MS(+)ES: 438 (M+H)$^+$; and the title R-isomer was obtained as a white solid, mp 112-114° C.; $[\alpha]_{25}=+35$ (1% in DMSO); MS(+)ES: 438 (M+H)$^+$.

EXAMPLE 139

Preparation of (5S)-2-Amino-5-[4-(2-fluoroethoxy) phenyl]-5-(4-fluoro-3-pyrimidin-5-ylphenyl)-3-methyl-3,5-dihydro-4H-imidazol-4-one [A] and (5R)-2-Amino-5-[4-(2-fluoroethoxy)phenyl]-5-(4-fluoro-3-pyrimidin-5-ylphenyl)-3-methyl-3,5-dihydro-4H-imidazol-4-one [B]

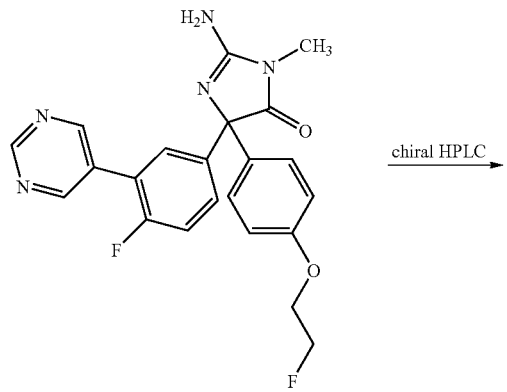

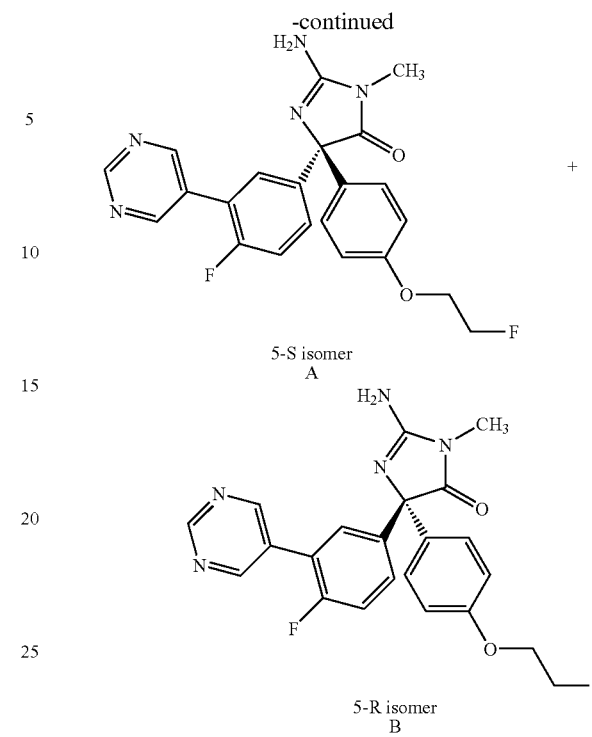

5-S isomer
A

5-R isomer
B

A racemic mixture of 2-amino-5-[4-(2-fluoroethoxy)phenyl]-5-(4-fluoro-3-pyrimidin-5-ylphenyl)-3-methyl-3,5-dihydro-4H-imidazol-4-one was separated by chiral HPLC: Chiralcel AD, 2×25 cm using mobile phase EtOH:Hexane (15:85) and a flow rate of 20 mL/min to give the title S-isomer (A) as a white solid, mp 120° C.; $[\alpha]_{25}=-35.09$ (0.53% in MeOH); $^1$H NMR (400 MHZ, DMSO-d$_6$) δ 2.97 (s, 3H), 4.14-4.15 (m, 1H), 4.20-4.21 (m, 1H,) 4.65-4.66 (m, 1H), 4.74-4.75 (m, 1H), 6.67 (bs, 2H), 6.88-6.89 (d, 2H), 7.34 (m, 1H), 7.35-7.37 (d, 2H), 7.57, (m, 1H), 7.65 (m, 1H), 8.92 (s, 2H), 9.22 (s, 1H); MS m/e (M–H)$^-$ 422.1; and the title R-isomer as a white solid, mp 120° C.; $[\alpha]_{25}=+31.2$ (1% in MeOH); $_1$H NMR (400 MHZ, DMSO-d$_6$) δ 2.97 (s, 3H), 4.15-4.16 (m, 1H), 4.20-4.21 (m, 1H), 4.65-4.66 (m, 1H), 4.74-4.75 (m, 1H), 6.67 (bs, 2H), 6.88-6.89 (d, 2H), 7.34 (m, 1H), 7.35-7.37 (d, 2H), 7.55, (m, 1H), 7.65 (m, 1H), 8.92 (s, 2H), 9.22 (s, 1H); MS m/e (M–H)$^-$ 422.1.

EXAMPLES 140 AND 141

Preparation of (5S)-2-Amino-5-[4-(2-fluoroethoxy) phenyl]-3-methyl-5-(3-heteroarylphenyl)-3,5-dihydro-4H-imidazol-4-one Compounds

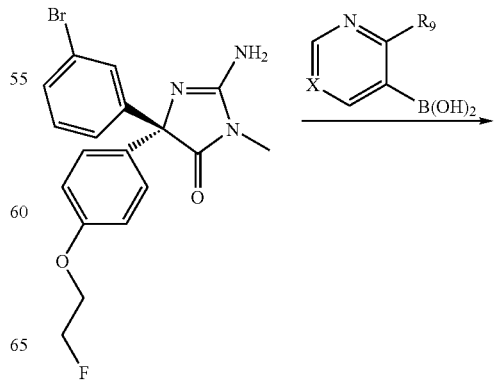

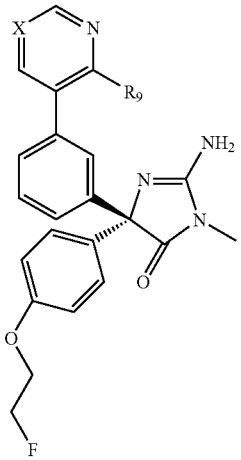

Using essentially the same procedure described in Example 40 and employing (5S)-2-amino-5-(3-bromophenyl)-5-[4-(2-fluoroethoxy)phenyl]-3-methyl-3,5-dihydro-4H-imidazol-4-one and a suitable heteroarylboronic acid, the compounds shown on Table V were obtained and identified by HNMR and mass spectral analyses.

TABLE V

| Ex. No | R9 | X | $[\alpha]_{25}$ | mp ° C. |
|---|---|---|---|---|
| 140 | H | N | −18.4 (1% MeOH) | 145 |
| 141 | F | CH | — | 106 |

EXAMPLE 142

Preparation of (5S)-2-Amino-5-[4-fluoro-3-(5-fluoropyridin-3-yl)phenyl]-5-(4-methoxyphenyl)-3-methyl-3,5-dihydro-4H-imidazol-4-one [A] and (5R)-2-Amino-5-[4-fluoro-3-(5-fluoropyridin-3-yl)phenyl]-5-(4-methoxyphenyl)-3-methyl-3,5-dihydro-4H-imidazol-4-one [B]

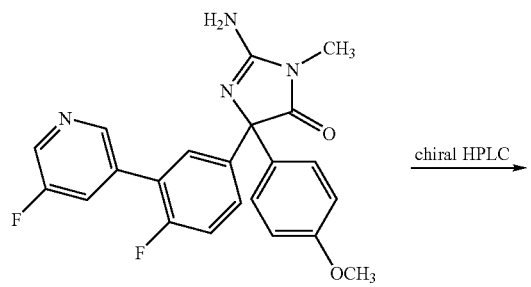

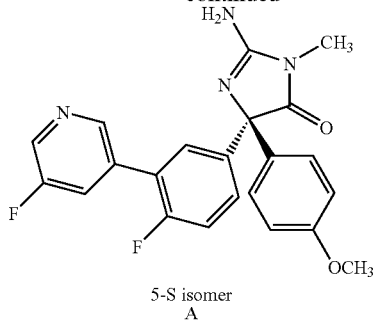

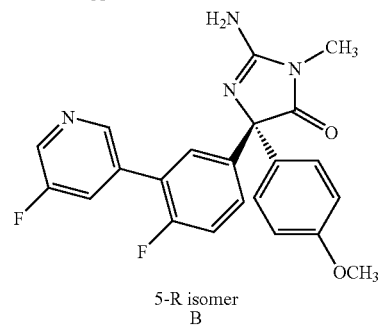

A racemic mixture of 2-amino-5-[4-fluoro-3-(5-fluoropyridin-3-yl)phenyl]-5-(4-methoxyphenyl)-3-methyl-3,5-dihydro-4H-imidazol-4-one was separated by chiral HPLC: Chiralcel OJ, 2×25 cm (column) with mobile phase 30% EtOH in hexanes (0.1% diethtylamine) to give the title S-isomer (A): $[\alpha]_{25}$=−37.6 (1% in MeOH); $^1$H NMR (DMSOd$_6$ 300 MHz) δ 2.93 (s 3H), 3.63 (s 3H), 6.6 (brs, 2H), 6.8 (d, 2H), 7.22-7.35 (m, 3H), 7.5 (m, 1H), 7.6 (dd, 1H), 7.8 (m, 1H), 8.5 (d, 1H), 8.6 (d, 1H); MS m/e (M+H)$^+$ 409 and the title R-isomer (B): $[\alpha]_{25}$=+35.4 (1% in MeOH); $^1$H NMR (DMSOd$_6$ 300 MHz) δ 2.93 (s 3H), 3.63 (s 3H), 6.6 (brs, 2H), 6.8 (d, 2H), 7.22-7.35 (m, 3H), 7.5 (m, 1H), 7.6 (dd, 1H), 7.8 (m, 1H), 8.5 (d, 1H), 8.6 (d, 1H); MS m/e (M+H)$^+$ 409.

EXAMPLE 143

Preparation of (5S)-2-Amino-5-[4-fluoro-3-(4-fluoropyridin-3-yl)phenyl]-5-(4-methoxyphenyl)-3-methyl-3,5-dihydro-4H-imidazol-4-one [A] and (5R)-2-Amino-5-[4-fluoro-3-(4-fluoropyridin-3-yl)phenyl]-5-(4-methoxyphenyl)-3-methyl-3,5-dihydro-4H-imidazol-4-one [B]

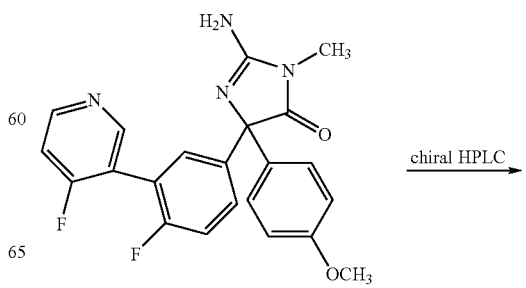

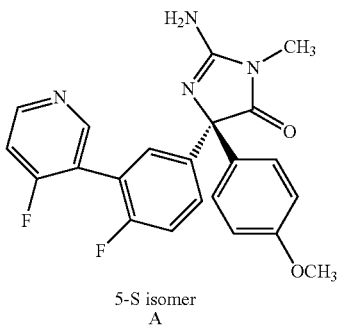

5-S isomer
A

+

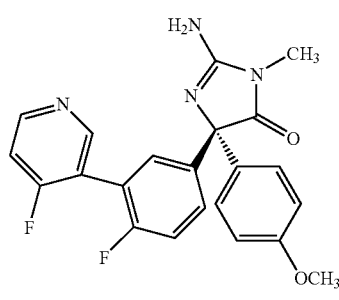

5-R isomer
B

A racemic mixture of 2-amino-5-[4-fluoro-3-(4-fluoropyridin-3-yl)phenyl]-5-(4-methoxyphenyl)-3-methyl-3,5-dihydro-4H-imidazol-4-one was separated by chiral HPLC: Chiralcel OJ, 0.46×25 cm (column) with mobile phase 80% EtOH in hexanes (0.1% diethylamine) to give the title S-isomer (A): $[\alpha]_{25}=-40$ (1% in MeOH); $^1$H NMR (DMSOd$_6$ 300 MHz) δ 2.93 (s, 3H), 3.66 (s, 3H), 6.65 (brs, 2H), 6.8 (d, 2H), 7.3 (m, 3H), 7.43 (m, 1H), 7.52 (m, 2H), 8.55 (d, 1H), 8.63 (t, 1H); MS m/e (M+H)$^+$ 409; and title R-isomer (B): $[\alpha]_{25}=+38.8$ (1% in MeOH); $^1$H NMR (DMSOd$_6$ 300 MHz) □ 2.93 (s, 3H), 3.66 (s, 3H), 6.65 (brs, 2H), 6.8 (d, 2H), 7.3 (m, 3H), 7.43 (m, 1H), 7.52 (m, 2H), 8.55 (d, 1H), 8.63 (t, 1H), MS m/e (M+H)$^+$ 409.

EXAMPLE 144

Preparation of 4-[4-Fluoro-3-(2-fluoropyridin-3-yl)phenyl]-1-methyl-4-(4-trifluoromethoxyphenyl)-4,5-dihydro-1H-imidazol-2-ylamine

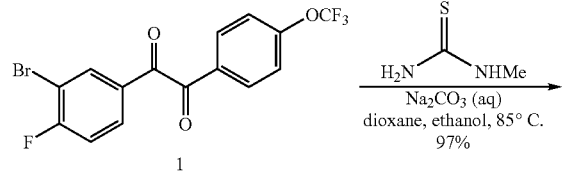

1

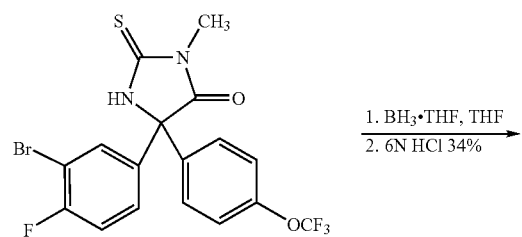

2

1. BH$_3$·THF, THF
2. 6N HCl 34%

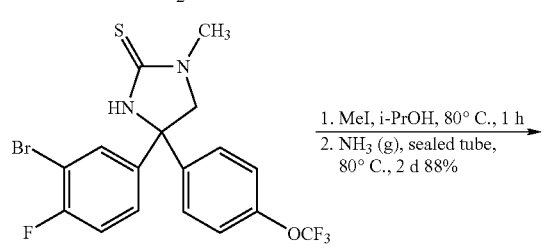

3

1. MeI, i-PrOH, 80° C., 1 h
2. NH$_3$ (g), sealed tube, 80° C., 2 d 88%

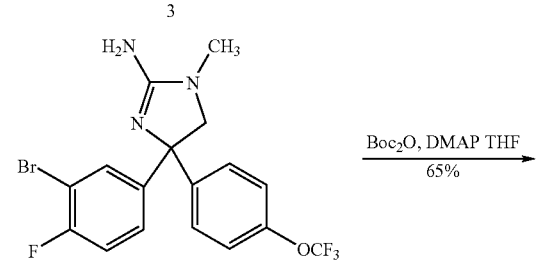

4

Boc$_2$O, DMAP THF
65%

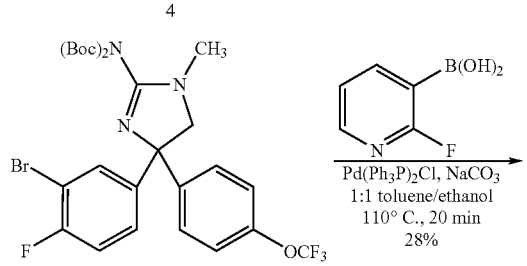

5

Pd(Ph$_3$P)$_2$Cl, NaCO$_3$
1:1 toluene/ethanol
110° C., 20 min
28%

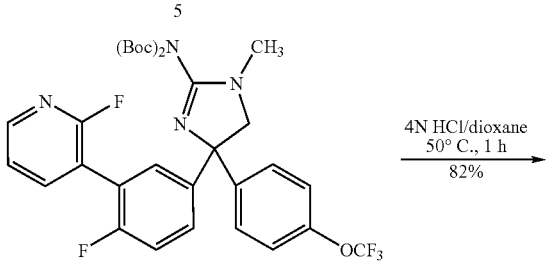

6

4N HCl/dioxane
50° C., 1 h
82%

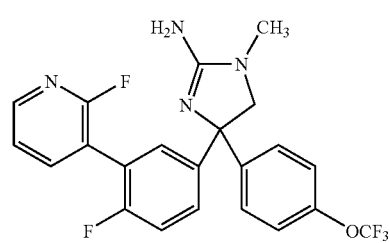

Step a) Preparation of Compound 2

A mixture of 1 (2.00 g, 5.1 mmol) and 1-methyl-2-thiourea (2.07 g, 23.0 mmol) in ethanol (50 mL) and dioxane (50 mL) was stirred at room temperature for 5 min. A solution of sodium carbonate (2.44 g, 23.0 mmol) in water (20 mL) was added and the reaction was stirred at 85° C. for 15 min. The reaction was then cooled to room temperature, concentrated and diluted with ethyl acetate (100 mL) and brine (20 mL). The organic layer was separated and washed with brine (10 mL), dried over sodium sulfate, filtered and concentrated. Purification by flash chromatography (silica, 1:9 ethyl acetate/hexanes) afforded 2 (2.30 g, 97%) as a yellow solid: $^1$H NMR (300 MHz, CD$_3$OD) δ 7.61 (dd, J=6.3, 2.4 Hz, 1H), 7.46-7.27 (m, 6H), 3.27 (s, 3H).

Step b) Preparation of Compound 3

A mixture of 2 (2.20 g, 4.75 mmol) and 1.0 M borane tetrahydrofuran complex in tetrahydrofuran (47.5 mL, 47.5 mmol) in tetrahydrofuran (66 mL) was heated at reflux overnight, then treated with 6 N HCl (24 mL, 143 mmol) and heated at 80° C. for 1 h. The reaction was cooled to room temperature, neutralized with sodium bicarbonate solid (12.0 g, 143 mmol) and diluted with ethyl acetate (200 mL). The organic layer was separated and washed with brine (20 mL), dried over sodium sulfate, filtered and concentrated. Purification by flash chromatography (silica, 1:9 to 2:8 ethyl acetate/hexanes) afforded 3 (0.73 g, 34%) as a colorless oil: $^1$H NMR (300 MHz, CDCl$_3$) δ 8.14 (s, 1H), 7.42 (m, 1H), 7.31-7.05 (m, 6H), 4.18 (s, 2H), 3.19 (s, 3H); ESI MS m/z 450 [C$_{17}$H$_{13}$BrF$_4$N$_2$OS+H]$^+$.

Step c) Preparation of Compound 4

A mixture of 3 (0.73 g, 1.63 mmol), methyl iodide (0.25 g, 1.79 mmol) in isopropanol (10 mL) was heated at 80° C. for 1 h, concentrated, redissolved in isopropanol (20 mL), cooled to 0° C. and charged with ammonia gas (2.0 g). The reaction vessel was sealed and heated at 80° C. for 48 h. The reaction was cooled to room temperature, concentrated and purified by flask chromatography (100:0:0 to 80:20:0.5 methylene chloride/methanol/concentrated ammonium hydroxide) afforded 4 (0.62 g, 88%) as a colorless syrup: $^1$H NMR (300 MHz, CD$_3$OD) δ 7.62 (dd, J=6.3, 2.4 Hz, 1H), 7.61-7.20 (m, 6H), 4.35 (s, 2H), 3.08 (s, 3H); ESI MS m/z 432 [C$_{17}$H$_{14}$BrF$_4$N$_3$O+H]$^+$.

Step d) Preparation of Compound 5

A mixture of 4 (0.52 g, 1.20 mmol), 4-dimethylaminopyridine (0.77 g, 6.32 mmol) and di-tert-butyldicarbonate (1.38 g, 6.32 mmol) in tetrahydrofuran (5 mL) was stirred at room temperature for 1 h and concentrated. Purification by flash chromatography (silica, 1:9 to 2:8 ethyl acetate/hexanes) afforded 5 (0.49 g, 65%) as a white solid: $^1$H NMR (300 MHz, CD$_3$OD) δ 7.67 (dd, J=6.6, 2.1 Hz, 1H), 7.44-7.03 (m, 6H), 4.05 (d, J=9.9 Hz, 1H), 3.86 (d, J=9.9 Hz, 1H), 2.79 (s, 3H), 1.39 (s, 18H); ESI MS m/z 632 [C$_{27}$H$_{30}$BrF$_4$N$_3$O$_5$+H]$^+$.

Step e) Preparation of Compound 6

A mixture of 5 (0.19 g, 0.300 mmol), 2-fluoropyridine-3-boronic acid (0.064 g, 0.451 mmol), sodium carbonate (0.096 g, 0.900 mmol), bis(triphenylphosphino)palladium (II) dichloride (0.021 g, 0.030 mmol) and triphenylphosphine (0.016 g, 0.060 mmol) in 1:1 toluene/EtOH (10 mL) was degassed and heated at 110° C. for 20 min. The mixture was cooled to room temperature and concentrated. Purification by flash chromatography (silica, 1:9 to 4:6 ethyl acetate/hexanes) afforded 6 (0.055 g, 28%) as a white solid: $^1$H NMR (500 MHz, CDCl$_3$) δ 8.24 (m, 1H), 7.82 (m, 1H), 7.48-7.11 (m, 8H), 4.03 (d, J=9.5 Hz, 1H), 3.95 (d, J=9.5 Hz, 1H), 2.78 (s, 3H), 1.31 (s, 18H); ESI MS m/z 649 [C$_{32}$H$_{33}$F$_5$N$_4$O$_5$+H]$^+$.

Step f) Preparation of 4-[4-fluoro-3-(2-fluoro-pyridin-3-yl)-phenyl]-1-methyl-4-(4-trifluoromethoxy-phenyl)-4,5-dihydro-1H-imidazol-2-ylamine A mixture of 6 (0.055 g, 0.085 mmol) and 4 M hydrogen chloride in dioxane (5 mL) was heated at 50° C. for 1 h, cooled to room temperature and concentrated. The reaction mixture was then diluted with chloroform (50 mL) and sodium bicarbonate (10 mL). The organic layer was separated and washed with brine (20 mL), dried over sodium sulfate, filtered and concentrated. Purification by preparative HPLC afforded the title product as a white solid, 0.031 g (82% yield), mp 65-70° C.; $^1$H NMR (500 MHz, CD$_3$OD) δ 8.22 (m, 1H), 7.95 (m, 1H), 7.35-7.23 (m, 8H), 4.10 (t, J=7.5 Hz, 2H), 2.93 (t, J=7.5 Hz, 3H); IR (ATR) 3059, 2926, 1670, 1641, 1570, 1503, 1427, 1253, 1201, 1161, 829, 804, 765, 718 cm$^{-1}$; ESI MS m/z 449 [C$_{22}$H$_{17}$F$_5$N$_4$O+H]$^+$.

EXAMPLE 145

Preparation of 2-Amino-5-[3-(2-fluoro-pyridin-3-yl)-phenyl]-3-methyl-5-(4-trifluoromethoxy-phenyl)-3,5-dihydro-imidazole-4-thione

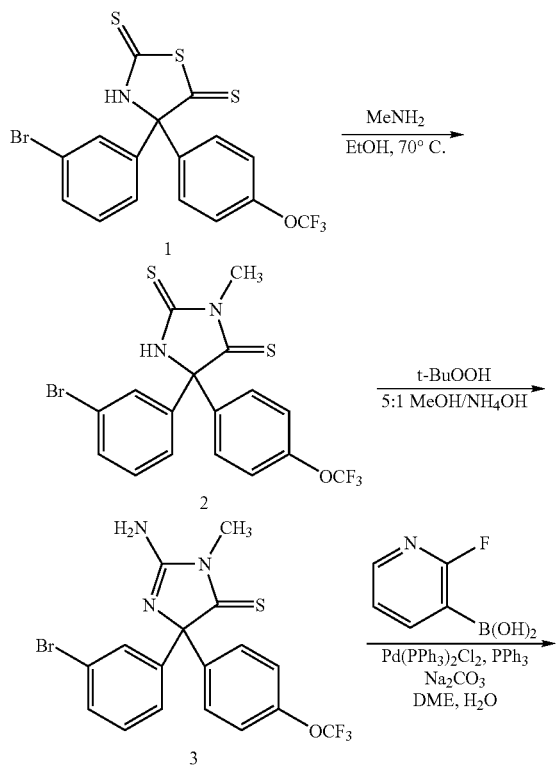

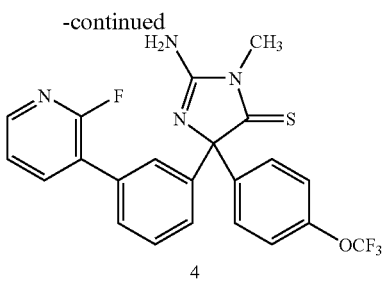

Step a) Preparation of Compound 2

A mixture of methylamine hydrochloride (0.210 g, 3.18 mmol), triethylamine (0.320 g, 3.18 mmol) and 1 (0.470 g, 1.06 mmol) in ethanol was stirred at 70° C. for 1 h. The solvents were evaporated and the residue partitioned between ethyl acetate and water. The organic layer was separated and washed with brine (30 mL), dried over sodium sulfate, filtered and concentrated to afford 2 (0.460 g, 99%) as a yellow solid: $^1$H NMR (300 MHz, CDCl$_3$) δ 7.71 (br s, 1H), 7.58-7.49 (m, 2H), 7.37 (d, J=8.9 Hz, 2H), 7.30-7.19 (m, 3H), 3.68 (s, 3H).

Step b) Preparation of Compound 3

A mixture of 2 (0.458 g, 1.05 mmol) and t-butyl hydroperoxide (1.88 g of a 70% solution in water, 21.0 mmol) in methanol (50 mL) and concentrated aqueous ammonium hydroxide (10 mL) was stirred overnight at room temperature. After this time, 10% aqueous sodium thiosulfate (30 mL) was added; the mixture was concentrated to remove most of the methanol and then the aqueous mixture was diluted with methylene chloride. The organic layer was separated, washed with brine (30 mL), dried over sodium sulfate, filtered and concentrated. Purification of the resultant residue by flash chromatography (silica, 95:5 methylene chloride/methanol) afforded 3 (0.250 g, 57%) as a white solid: $^1$H NMR (300 MHz, CDCl$_3$) δ 7.88 (t, J=1.7 Hz, 1H), 7.81 (d, J=8.9 Hz, 2H), 7.72-7.65 (m, 2H), 7.36 (t, J=7.8 Hz, 1H), 6.98 (d, J=8.9 Hz, 2H), 3.90 (s, 3H); ESI MS m/z 444 [C$_{17}$H$_{13}$BrF$_3$N$_3$OS+H]$^+$.

Step c) Preparation of 2-amino-5-[3-(2-fluoro-pyridin-3-yl)-phenyl]-3-methyl-5-(4-trifluoromethoxy-phenyl)-3,5dihydro-imidazole-4-thione A mixture of 3 (0.16 g, 0.38 mmol), 2-fluoropyridine-3-boronic acid (0.075 g, 0.530 mmol), bis(triphenylphosphino) palladium(II) chloride (0.013 g, 0.019 mmol), triphenylphosphine (0.010 g, 0.038 mmol) and sodium carbonate (0.121 g 1.14 mmol) in 3:1 DME/water (6.0 mL) was heated at 80° C. for 1 h. The mixture was cooled to room temperature and concentrated in vacuo. The resultant residue was diluted with ethyl acetate and water. The organic layer was separated and washed with brine (20 mL), dried over sodium sulfate, filtered and concentrated. Purification of this residue by flash chromatography (silica, 97:2.5:0.5 methylene chloride/methanol/concentrated ammonium hydroxide) afforded 0.087 g of a pale yellow solid. This material was freeze dried from 1:1 acetonitrile/water (6 mL) to afford the title product as a pale yellow solid, 0.069 g (39% yield), mp 89-99° C.; $^1$H NMR (300 MHz, CDCl$_3$) δ 8.17 (dt, J=4.8, 1.5 Hz, 1H), 7.86-7.79 (m, 1H), 7.65 (br s, 1H), 7.55-7.48 (m, 4H), 7.44-7.38 (m, 1H), 7.27-7.25 (m, 1H), 7.14 (d, J=8.9 Hz, 2H), 3.48 (s, 3H); ESI MS m/z 461 [C$_{22}$H$_{16}$F$_4$N$_4$OS+H]$^+$;

EXAMPLE 146

Evaluation of the Inhibition of hBACE1, MuBACE1 and hBACE2 by Test Compounds

Assay Conditions: 10 nM human BACE1 (or 10 nM Murine BACE1, 1.5 nM human BACE2) 25 μM substrate (WABC-6, MW 1549.6, from AnaSpec); final buffer conditions: 50 mM Na-Acetate, pH 4.5, 0.05% CHAPS, 25% PBS; temperature: room temperature; reagent information: Na-Acetate: Aldrich, Cat.# 24,124-5 CHAPS: Research Organics, Cat. # 1304C 1×PBS: Mediatech (Cellgro), Cat# 21-031-CV; peptide substrate AbzSEVNLDAEFRDpa: AnaSpec, Peptide Name: WABC-6; determination of stock substrate (AbzSEVNLDAEFRDpa) concentration: a 25 mM stock solution in dimethyl sulfoxide (DMSO) is prepared using the peptide weight and MW and diluted to 25 μM. The concentration is determined by absorbance at 354 nm using an extinction coefficient ε of 18172 M$^{-1}$cm$^{-1}$, The substrate stock is stored in small aliquots at −80° C. [Substrate Stock] =ABS$^{354\,nm}$* 10$^6$/18172 (in mM)

Determination of Stock Enzyme Concentration: The stock concentration of each enzyme by ABS at 280 nm using □ of 64150 M$^{-1}$cm$^{-1}$ for hBACE1 and MuBACE1, 62870 M$^{-1}$cm$^{-1}$ for hBACE2 in 6 M Guanidinium Hydrochloride (from Research Organics, Cat. # 5134G-2), pH 6.

(The extinction coefficient ε$^{280\,nm}$ for each enzyme was calculated based on known amino acid composition and published extinction coefficients for Trp (5.69 M$^{-1}$ cm$^{-1}$) and Tyr (1.28 M$^{-1}$ cm$^{-1}$) residues (*Anal. Biochem.* 182, 319-326).

Dilution and mixing steps: total reaction volume: 100 μL
1. 2× inhibitor dilutions in buffer A(66.7 mM Na-Acetate, pH 4.5, 0.0667% CHAPS) are prepared,
2. 4× enzyme dilution in buffer A(66.7 mM Na-Acetate, pH 4.5, 0.0667% CHAPS) are prepared,
3. 100 μM substrate dilution in 1×PBS is prepared,
4. 50 μL 2× Inhibitor and 25 μL 100 μM substrate are added to each well of 96-well plate (from DYNEX Technologies, VWR #: 11311-046), the immediately 25 μL 4× enzyme are added to the inhibitor and substrate mixer, the fluorescence readings are initiated.

Fluorescence Readings: Readings at λ$_{ex}$ 320 nm and λ$_{em}$ 420 nm are taken every 40-sec for 30 min at room temperature to determine the linear slope for substrate cleavage rate (v$_i$).

Calculation of % Inhibition: % Inhibition=100*(1−v$_i$/v$_0$) (v$_i$=substrate cleavage rate in the presence of inhibitor, v$_0$=substrate cleavage rate in the absence of inhibitor)

IC$_{50}$ Determination: % Inhibition=[(B*IC$_{50}^n$)+(100*I$_0^n$)]/ (IC$_{50}^n$+I$_0^n$), Fluorescent Kinetic Assay for Human Recombinant BACE 2

This assay is used to provide kinetic and selectivity parameters for the analyses of the tested compounds.

Materials and methods: final assay conditions: 10 nM human BACE1 (or 10 nM Murine BACE1, 1.5 nM human BACE2) 25 μM Substrate (WABC-6, MW 1549.6, from AnaSpec). Final buffer conditions: 50 mM Na-Acetate, pH 4.5, 0.05% CHAPS, 25% PBS. Temperature: room temperature. Reagent Information: Na-Acetate: Aldrich, Cat.# 24,124-5 CHAPS: Research Organics, Cat. # 1304C 1×PBS: Mediatech (Cellgro), Cat# 21-031-CV Peptide Substrate AbzSEVNLDAEFRDpa: AnaSpec, Peptide Name: WABC-6

Determination of stock substrate (AbzSEVNLDAE-FRDpa) concentration: A 25 mM stock solution in DMSO is prepared using the peptide weight and MW, and diluted to 25 μM. The concentration is determined by absorbance at 354 nm using an extinction coefficient ε of 18172 M$^{-1}$cm$^{-1}$. The substrate stock is stored in small aliquots at −80° C. [Substrate Stock]=ABS$^{354\,nm}$*10$^6$/18172 (in mM)

Determination of stock enzyme concentration: The stock concentration of each enzyme is determined by ABS at 280 nm using $\epsilon$ of 64150 M$^{-1}$cm$^{-1}$ for hBACE1 and MuBACE1, 62870 M$^{-1}$cm$^{-1}$ for hBACE2 in 6 M guanidinium hydrochloride (from Research Organics, Cat. # 5134G-2), pH 6. (The extinction coefficient $\epsilon^{280\,nm}$ for each enzyme is calculated based on known amino acid composition and published extinction coefficients for Trp (5.69 M$^{-1}$ cm$^{-1}$) and Tyr (1.28 M$^{-1}$ cm$^{-1}$) residues (*Anal. Biochem.* 182, 319-326).)

Dilution and Mixing Steps: Total Reaction Volume.: 100 μL
1. 2× inhibitor dilutions in buffer A (66.7 mM Na-Acetate, pH 4.5, 0.0667% CHAPS) are prepared,
2. 4× enzyme dilution in buffer A (66.7 mM Na-Acetate, pH 4.5, 0.0667% CHAPS) are prepared,
3. 100 μM substrate dilution in 1×PBS, 50 μL 2× Inhibitor and 25 μL 100 μM substrate are added to each well of 96-well plate (from DYNEX Technologies, VWR #: 11311-046), then immediately 25 μL 4× enzyme is added to the inhibitor and substrate mixer and the fluorescence readings are initiated.

Fluorescence Readings: Readings at $\lambda_{ex}$ 320 nm, $\lambda_{em}$ 420 nm are taken every 40-sec for 30 min at room temperature and to determine the linear slope for substrate cleavage rate ($v_i$).

Analysis of calculation of % inhibition: % Inhibition=100*$(1-v_i/v_0)$
$v_i$=substrate cleavage rate in the presence of inhibitor,
$v_0$=substrate cleavage rate in the absence of inhibitor)
IC$_{50}$ Determination:
% Inhibition=$((B*IC_{50}{''})+(100*I_0{''}))/(IC_{50}{''}+I_0{''})$, The data obtained are shown on Table VI.

TABLE VI

| Ex. No. | IC$_{50}$ (μM) BACE1 | BACE1/BACE2 |
|---|---|---|
| 5 | B | III |
| 6 | B | III |
| 7 | A | II |
| 8 | A | II |
| 9 | A | II |
| 10 | A | II |
| 11 | A | II |
| 12 | A | II |
| 13 | A | II |
| 14 | A | II |
| 15 | B | II |
| 16 | A | III |
| 17 | A | III |
| 18 | A | II |
| 19 | A | III |
| 20 | B | III |
| 21 | A | II |
| 22 | A | III |
| 23 | A | II |
| 24 | A | II |
| 25 | A | II |
| 26 | A | II |
| 27 | A | II |
| 28 | A | II |
| 29 | A | II |
| 30 | B | III |
| 31 | B | III |
| 32 | A | III |
| 36 | A | III |
| 37 | A | III |
| 38A | C | III |
| 38B | A | II |
| 41 | B | II |

TABLE VI-continued

| Ex. No. | IC$_{50}$ (μM) BACE1 | BACE1/BACE2 |
|---|---|---|
| 42 | B | II |
| 43 | A | II |
| 44 | A | II |
| 46 | B | II |
| 47 | B | II |
| 48 | C | II |
| 49 | B | I |
| 50 | A | II |
| 51 | A | III |
| 52 | B | II |
| 53 | B | III |
| 54 | A | I |
| 55 | A | II |
| 56 | A | I |
| 57 | A | II |
| 58 | A | II |
| 59 | A | II |
| 60 | A | II |
| 61 | A | II |
| 62 | A | II |
| 63 | A | I |
| 64 | C | III |
| 65 | B | II |
| 66 | A | II |
| 67 | A | III |
| 68 | B | III |
| 69 | A | III |
| 70 | A | II |
| 71 | A | III |
| 72 | B | II |
| 73 | B | II |
| 74 | A | II |
| 75 | B | II |
| 77 | A | I |
| 78 | A | II |
| 79 | A | II |
| 80 | A | III |
| 81 | A | II |
| 82 | A | II |
| 83 | A | II |
| 84 | B | I |
| 86 | A | I |
| 88 | A | II |
| 89 | A | II |
| 90 | A | II |
| 91 | A | II |
| 92 | A | II |
| 93 | A | II |
| 94 | B | II |
| 95 | A | II |
| 96 | A | II |
| 97 | A | II |
| 99 | A | III |
| 100 | B | III |
| 101A | C | III |
| 101B | A | I |
| 102A | B | III |
| 102B | A | II |
| 103A | C | III |
| 103B | A | II |
| 104 | A | II |
| 105A | B | III |
| 105B | A | II |
| 106A | C | III |
| 106B | A | I |
| 107A | A | I |
| 107B | C | III |
| 108 | A | II |
| 109 | A | II |
| 110 | A | II |
| 111 | B | III |
| 112 | A | II |
| 113 | A | I |
| 114 | A | II |
| 115 | A | II |

TABLE VI-continued

| Ex. No. | IC$_{50}$ (μM) BACE1 | BACE1/BACE2 |
|---|---|---|
| 116 | A | II |
| 117 | A | II |
| 118 | A | I |
| 119 | B | II |
| 120 | A | I |
| 121 | A | II |
| 122 | A | II |
| 123 | B | II |
| 124 | A | II |
| 126 | B | I |
| 127 | B | I |
| 128 | B | II |
| 131 | A | II |
| 132 | C | III |
| 133A | B | III |
| 133B | A | II |
| 134A | B | III |
| 134B | A | II |
| 135A | C | III |
| 135B | A | II |
| 136A | A | II |
| 137A | C | III |
| 137B | A | II |
| 138A | A | I |
| 138B | C | III |
| 139A | A | I |
| 139B | B | III |
| 140 | A | I |
| 141 | A | II |
| 142A | C | III |
| 142B | A | II |
| 143A | C | III |
| 143B | A | II |
| 144 | B | I |
| 145 | A | II |

For Table VI
A = 0.01 μM-0.10 μM
B = 0.11 μM-1.00 μM
C = >1.00 μM
I = >100-fold selectivity
II = 10-100-fold selectivity
III = <10-fold selectivity Results and Discussion:

As can be seen from the data shown on Table VI hereinabove, the compounds of the invention are potent and selective inhibitors of BACE1.

What is claimed is:

1. A compound of formula I

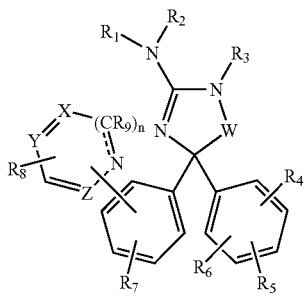

wherein W is CO;
X is N, NO or $CR_{10}$;
Y is N, NO or $CR_{11}$;
Z is N, NO or $CR_{19}$ with the proviso that no more than two of X, Y or Z may be N or NO;

$R_1$ and $R_2$ are each independently H, $COR_{20}$, $CO_2R_{21}$ or an optionally substituted $C_1$-$C_4$alkyl group;

$R_3$ is H, $OR_{12}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl ($C_1$-$C_6$)alkyl group each optionally substituted;

$R_4$ and $R_5$ are each independently H, halogen, $NO_2$, CN, $OR_{13}$, $NR_{14}R_{15}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted or when attached to adjacent carbon atoms $R_4$ and $R_5$ may be taken together with the atoms to which they are attached to form an optionally substituted 5- to 7-membered ring optionally containing one or two heteroatoms selected from O, N or S;

$R_6$, $R_7$, $R_8$, $R_9$, $R_{10}$, $R_{11}$ and $R_{19}$ are each independently H, halogen, $NO_2$, CN, $OR_{16}$, $NR_{17}R_{18}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;

n is 0 or 1;

═ is a single bond when n is 0 or a double bond when n is 1;

$R_{12}$, $R_{13}$, $R_{16}$, $R_{20}$ and $R_{21}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each optionally substituted; and $R_{14}$, $R_{15}$, $R_{17}$ and $R_{18}$ are each independently H or $C_1$-$C_4$alkyl; or a tautomer thereof, a stereoisomer thereof or a pharmaceutically acceptable salt thereof.

2. The compound according to claim 1 wherein $R_3$ is methyl.

3. The compound according to claim 1 wherein $R_1$ and $R_2$ are H and $R_3$ is $C_1$-$C_4$alkyl.

4. The compound according to claim 1 wherein n is 1.

5. The compound according to claim 1 having the structure Ia

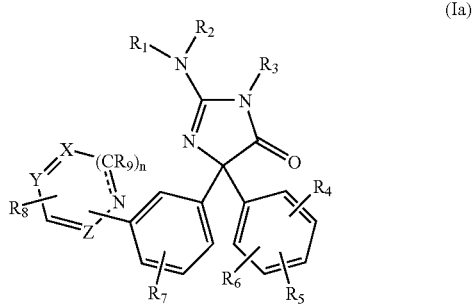

wherein, $R_5$ is $OR_{13}$ or optionally substituted $C_1$-$C_6$ alkyl.

6. The compound according to claim 1 having the structure Ib

7. The compound according to claim 6 wherein $R_3$ is methyl.

8. The compound according to claim 7 wherein Y is $CR_{11}$ and $R_1$ and $R_2$ are H.

9. The compound according to claim 1 selected from the group consisting of:
2-amino-5-(4-fluoro-3-pyrimidin-5-ylphenyl)-5-(4-methoxy-3-methylphenyl)-3-methyl-3,5-dihydro-4H-imidazol-4-one;
(5S)-2-amino-5-[3-(2-fluoropyridin-3-yl)phenyl]-5-(4-methoxy-3-methylphenyl)-3-methyl-3,5-dihydro-4H-imidazol-4-one;
2-amino-5-(4-methoxy-3-methylphenyl)-3-methyl-5-(3-pyrimidin-5-ylphenyl)-3,5-dihydro-4H-imidazol-4-one;
(5S)-2-amino-5-(4-methoxy-3-methylphenyl)-3-methyl-5-(3-pyrimidin-5-ylphenyl)-3,5-dihydro-4H-imidazol-4-one;
(5R)-2-amino-5-(4-fluoro-3-pyrimidin-5-ylphenyl)-3-methyl-5-[4-(trifluoromethoxy)phenyl]-3,5-dihydro-4H-imidazol-4-one;
4-[2-amino-4-(4-methoxy-3-methylphenyl)-1-methyl-5-oxo-4,5-dihydro-1H-imidazol-4-yl]-2-pyridin-3-ylbenzonitrile;
2-amino-5-(4-methoxy-3-methylphenyl)-3-methyl-5-(4-methyl-3-pyridin-3-ylphenyl)-3,5-dihydro-4H-imidazol-4-one;
2-amino-5-[4-methoxy-3-(trifluoromethyl)phenyl]-3-methyl-5-(3-pyridin-3-ylphenyl)-3,5-dihydro-4H-imidazol-4-one;
2-amino-3-ethyl-5-(4-methoxy-3-methylphenyl)-5-(3-pyridin-3-ylphenyl)-3,5-dihydro-4H-imidazol-4-one;
2-amino-5-(4-methoxy-3-methylphenyl)-3-methyl-5-(3-pyrazin-2-ylphenyl)-3,5-dihydro-4H-imidazol-4-one;
2-amino-3-methyl-5-(3-pyrimidin-2-ylphenyl)-5-[4-(trifluoromethoxy)phenyl]-3,5-dihydro-4H-imidazol-4-one;
2-amino-5-(4-hydroxy-3-methylphenyl)-3-methyl-5-(3-pyridin-3-ylphenyl)-3,5-dihydro-4H-imidazol-4-one;
2-amino-5-[4-methoxy-3-(trifluoromethyl)phenyl]-3-methyl-5-(3-pyrazin-2-ylphenyl)-3,5-dihydro-4H-imidazol-4-one;
(5R)-2-amino-5-(4-methoxy-3-methylphenyl)-3-methyl-5-(3-pyrimidin-5-ylphenyl)-3,5-dihydro-4H-imidazol-4-one;
2-amino-5-(4-methoxy-3-methylphenyl)-3-methyl-5-(3-pyridin-3-ylphenyl)-3,5-dihydro-4H-imidazol-4-one;
2-amino-5-(3,4-diethoxyphenyl)-3-methyl-5-(3-pyridin-3-ylphenyl)-3,5-dihydro-4H-imidazol-4-one;
2-amino-5-(3,4-dimethoxyphenyl)-3-methyl-5-(3-pyridin-3-ylphenyl)-3,5-dihydro-4H-imidazol-4-one;
2-amino-5-(3-cyclopentyl-4-methoxyphenyl)-3-methyl-5-(3-pyridin-3-ylphenyl)-3,5-dihydro-4H-imidazol-4-one;
2-amino-5-(4-methoxy-3-propoxyphenyl)-3-methyl-5-(3-pyridin-3-ylphenyl)-3,5-dihydro-4H-imidazol-4-one;
2-amino-5-(3-butoxy-4-methoxyphenyl)-3-methyl-5-(3-pyridin-3-ylphenyl)-3,5-dihydro-4H-imidazol-4-one;
2-amino-5-(3-isopropoxy-4-methoxyphenyl)-3-methyl-5-(3-pyridin-3-ylphenyl)-3,5-dihydro-4H-imidazol-4-one;
2-amino-5-(1,3-benzodioxol-5-yl)-3-methyl-5-(3-pyridin-3-ylphenyl)-3,5-dihydro-4H-imidazol-4-one;
2-amino-5-(2,3-dihydro-1-benzofuran-5-yl)-3-methyl-5-(3-pyridin-3-ylphenyl)-3,5-dihydro-4H-imidazol-4-one;
2-amino-5-[3-(cyclopentyloxy)-4-methoxyphenyl]-3-methyl-5-(3-pyridin-3-ylphenyl)-3,5-dihydro-4H-imidazol-4-one;
5-[2-amino-1-methyl-5-oxo-4-(3-pyridin-3-ylphenyl)-4,5-dihydro-1H-imidazol-4-yl]-2-methoxybenzonitrile;
2-amino-5-(3-fluoro-4-methoxyphenyl)-3-methyl-5-(3-pyridin-3-ylphenyl)-3,5-dihydro-4H-imidazol-4-one;
2-amino-5-(2,3-dihydro-1,4-benzodioxin-6-yl)-3-methyl-5-(3-pyridin-3-ylphenyl)-3,5-dihydro-4H-imidazol-4-one;
2-amino-5-(3-chloro-4-methoxyphenyl)-3-methyl-5-(3-pyridin-3-ylphenyl)-3,5-dihydro-4H-imidazol-4-one;
2-amino-3-methyl-5-(3-pyridin-3-ylphenyl)-5-(3,4,5-trimethoxyphenyl)-3,5-dihydro-4H-imidazol-4-one;
2-amino-5-(4-methoxy-3-methylphenyl)-3-methyl-5-(3-pyridin-4-ylphenyl)-3,5-dihydro-4H-imidazol-4-one;
2-amino-5-(3-ethoxy-4-methoxyphenyl)-3-methyl-5-(3-pyridin-3-ylphenyl)-3,5-dihydro-4H-imidazol-4-one;
2-amino-3-methyl-5-(3-pyridin-3-ylphenyl)-5-[4-(trifluoromethoxy)phenyl]-3,5-dihydro-4H-imidazol-4-one;
2-amino-3-methyl-5-(3-pyridin-3-ylphenyl)-5-[(4-trifluoromethoxy-3-trifluoromethyl)phenyl]-3,5-dihydro-4H-imidazol-4-one;
2-amino-5-(3,4-diethoxyphenyl)-5-(4-fluoro-3-pyridin-3-ylphenyl)-3-methyl-3,5-dihydro-4H-imidazol-4-one;
2-amino-5-(3-chloro-4-trifluoromethoxyphenyl)-5-(4-fluoro-3-pyridin-3-ylphenyl)-3-methyl-3,5-dihydro-4H-imidazol-4-one;
a tautomer thereof; a stereoisomer thereof; and
a pharmaceutically acceptable salt thereof.

10. A method for the treatment of Alzheimer's disease in a patient which comprises providing said patient with a therapeutically effective amount of a compound of formula I (I)

wherein W is CO;
X is N, NO or $CR_{10}$;
Y is N, NO or $CR_{11}$;
Z is N, NO or $CR_{19}$ with the proviso that no more than two of X, Y or Z may be N or NO;
$R_1$ and $R_2$ are each independently H, $COR_{20}$, $CO_2R_{21}$ or an optionally substituted $C_1$-$C_4$alkyl group;
$R_3$ is H, $OR_{12}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl($C_1$-$C_6$)alkyl group each optionally substituted;
$R_4$ and $R_5$ are each independently H, halogen, $NO_2$, CN, $OR_{13}$, $NR_{14}R_{15}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted or when attached to adjacent carbon atoms $R_4$ and $R_5$ may be taken together with the atoms to which they are attached to form an optionally substituted 5- to 7-membered ring optionally containing one or two heteroatoms selected from O, N or S;

$R_6$, $R_7$, $R_8$, $R_9$, $R_{10}$, $R_{11}$ and $R_{19}$ are each independently H, halogen, $NO_2$, CN, $OR_{16}$, $NR_{17}R_{18}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;

n is 0 or 1;

═ is a single bond when n is 0 or a double bond when n is 1;

$R_{12}$, $R_{13}$, $R_{16}$, $R_{20}$ and $R_{21}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each optionally substituted; and $R_{14}$, $R_{15}$, $R_{17}$ and $R_{18}$ are each independently H or $C_1$-$C_4$alkyl; or a tautomer thereof, a stereoisomer thereof or a pharmaceutically acceptable salt thereof.

11. The method according to claim 10 having a formula I compound wherein the structure is

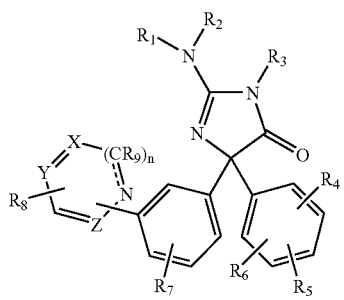

(Ia)

wherein $R_5$ is $OR_{13}$ or optionally substituted $C_1$-$C_6$alkyl.

12. The method according to claim 10 having a formula I compound wherein the structure is

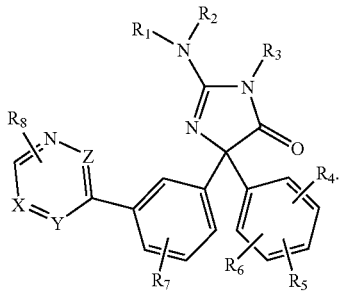

(Ib)

13. A pharmaceutical composition which comprises a pharmaceutically acceptable carrier and an effective amount of a compound of formula I

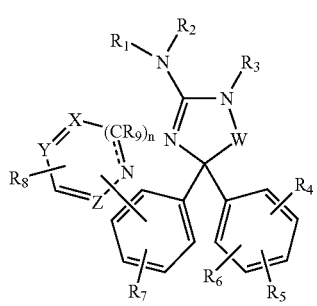

(I)

wherein W is CO;

X is N, NO or $CR_{10}$;

Y is N, NO or $CR_{11}$;

Z is N, NO or $CR_{19}$ with the proviso that no more than two of X, Y or Z may be N or NO;

$R_1$ and $R_2$ are each independently H, $COR_{20}$, $CO_2R_{21}$ or an optionally substituted $C_1$-$C_4$alkyl group;

$R_3$ is H, $OR_{12}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl ($C_1$-$C_6$)alkyl group each optionally substituted;

$R_4$ and $R_5$ are each independently H, halogen, $NO_2$, CN, $OR_{13}$, $NR_{14}R_{15}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted or when attached to adjacent carbon atoms $R_4$ and $R_5$ may be taken together with the atoms to which they are attached to form an optionally substituted 5- to 7-membered ring optionally containing one or two heteroatoms selected from O, N or S; $R_6$, $R_7$, $R_8$, $R_9$, $R_{10}$, $R_{11}$ and $R_{19}$ are each independently H, halogen, $NO_2$, CN, $OR_{16}$, $NR_{17}R_{18}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;

n is 0 or 1;

═ is a single bond when n is 0 or a double bond when n is 1;

$R_{12}$, $R_{13}$, $R_{16}$, $R_{20}$ and $R_{21}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each optionally substituted; and $R_{14}$, $R_{15}$, $R_{17}$ and $R_{18}$ are each independently H or $C_1$-$C_4$alkyl; or a tautomer thereof, a stereoisomer thereof or a pharmaceutically acceptable salt thereof.

14. The composition according to claim 13 having a formula I compound wherein the structure is Ia

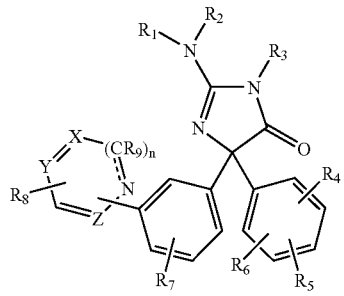

(Ia)

wherein, $R_5$ is $OR_{13}$ or optionally substituted $C_1$-$C_6$alkyl.

15. The composition according to claim 13 having a formula I compound wherein the structure is Ib

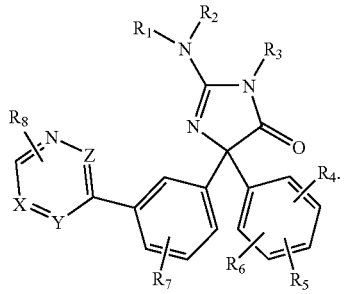

(Ib)

16. The composition according to claim 15 wherein $R_1$ and $R_2$ are H; $R_3$ is methyl; and Y is $CR_{11}$.

17. The composition according to claim 13 having a formula I compound selected from the group consisting of:

2-amino-5-(4-fluoro-3-pyrimidin-5-ylphenyl)-5-(4-methoxy-3-methylphenyl)-3-methyl-3,5-dihydro-4H-imidazol-4-one;

(5S)-2-amino-5-[3-(2-fluoropyridin-3-yl)phenyl]-5-(4-methoxy-3-methylphenyl)-3-methyl-3,5-dihydro-4H-imidazol-4-one;

2-amino-5-(4-methoxy-3-methylphenyl)-3-methyl-5-(3-pyrimidin-5-ylphenyl)-3,5-dihydro-4H-imidazol-4-one;

(5S)-2-amino-5-(4-methoxy-3-methylphenyl)-3-methyl-5-(3-pyrimidin-5-ylphenyl)-3,5-dihydro-4H-imidazol-4-one;

(5R)-2-amino-5-(4-fluoro-3-pyrimidin-5-ylphenyl)-3-methyl-5-[4-(trifluoromethoxy)phenyl]-3,5-dihydro-4H-imidazol-4-one;

4-[2-amino-4-(4-methoxy-3-methylphenyl)-1-methyl-5-oxo-4,5-dihydro-1H-imidazol-4-yl]-2-pyridin-3-ylbenzonitrile;

2-amino-5-(4-methoxy-3-methylphenyl)-3-methyl-5-(4-methyl-3-pyridin-3-ylphenyl)-3,5-dihydro-4H-imidazol-4-one;

2-amino-5-[4-methoxy-3-(trifluoromethyl)phenyl]-3-methyl-5-(3-pyridin-3-ylphenyl)-3,5-dihydro-4H-imidazol-4-one;

2-amino-3-ethyl-5-(4-methoxy-3-methylphenyl)-5-(3-pyridin-3-ylphenyl)-3,5-dihydro-4H-imidazol-4-one;

2-amino-5-(4-methoxy-3-methylphenyl)-3-methyl-5-(3-pyrazin-2-ylphenyl)-3,5-dihydro-4H-imidazol-4-one;

2-amino-3-methyl-5-(3-pyrimidin-2-ylphenyl)-5-[4-(trifluoromethoxy)phenyl]-3,5-dihydro-4H-imidazol-4-one;

2-amino-5-(4-hydroxy-3-methylphenyl)-3-methyl-5-(3-pyridin-3-ylphenyl)-3,5-dihydro-4H-imidazol-4-one;

2-amino-5-[4-methoxy-3-(trifluoromethyl)phenyl]-3-methyl-5-(3-pyrazin-2-ylphenyl)-3,5-dihydro-4H-imidazol-4-one;

(5R)-2-amino-5-(4-methoxy-3-methylphenyl)-3-methyl-5-(3-pyrimidin-5-ylphenyl)-3,5-dihydro-4H-imidazol-4-one;

2-amino-5-(4-methoxy-3-methylphenyl)-3-methyl-5-(3-pyridin-3-ylphenyl)-3,5-dihydro-4H-imidazol-4-one;

2-amino-5-(3,4-diethoxyphenyl)-3-methyl-5-(3-pyridin-3-ylphenyl)-3,5-dihydro-4H-midazol-4-one;

2-amino-5-(3,4-dimethoxyphenyl)-3-methyl-5-(3-pyridin-3-ylphenyl)-3,5-dihydro-4H-imidazol-4-one;

2-amino-5-(3-cyclopentyl-4-methoxyphenyl)-3-methyl-5-(3-pyridin-3-ylphenyl)-3,5-dihydro-4H-imidazol-4-one;

2-amino-5-(4-methoxy-3-propoxyphenyl)-3-methyl-5-(3-pyridin-3-ylphenyl)-3,5-dihydro-4H-imidazol-4-one;

2-amino-5-(3-butoxy-4-methoxyphenyl)-3-methyl-5-(3-pyridin-3-ylphenyl)-3,5-dihydro-4H-imidazol-4-one;

2-amino-5-(3-isopropoxy-4-methoxyphenyl)-3-methyl-5-(3-pyridin-3-ylphenyl)-3,5-dihydro-4H-imidazol-4-one;

2-amino-5-(1,3-benzodioxol-5-yl)-3-methyl-5-(3-pyridin-3-ylphenyl)-3,5-dihydro-4H-imidazol-4-one;

2-amino-5-(2,3-dihydro-1-benzofuran-5-yl)-3-methyl-5-(3-pyridin-3-ylphenyl)-3,5-dihydro-4H-imidazol-4-one;

2-amino-5-[3-(cyclopentyloxy)-4-methoxyphenyl]-3-methyl-5-(3-pyridin-3-ylphenyl)-3,5-dihydro-4H-imidazol-4-one;

5-[2-amino-1-methyl-5-oxo-4-(3-pyridin-3-ylphenyl)-4,5-dihydro-1H-imidazol-4-yl]-2-methoxybenzonitrile;

2-amino-5-(3-fluoro-4-methoxyphenyl)-3-methyl-5-(3-pyridin-3-ylphenyl)-3,5-dihydro-4H-imidazol-4-one;

2-amino-5-(2,3-dihydro-1,4-benzodioxin-6-yl)-3-methyl-5-(3-pyridin-3-ylphenyl)-3,5-dihydro-4H-imidazol-4-one;

2-amino-5-(3-chloro-4-methoxyphenyl)-3-methyl-5-(3-pyridin-3-ylphenyl)-3,5-dihydro-4H-imidazol-4-one;

2-amino-3-methyl-5-(3-pyridin-3-ylphenyl)-5-(3,4,5-trimethoxyphenyl)-3,5-dihydro-4H-imidazol-4-one;

2-amino-5-(4-methoxy-3-methylphenyl)-3-methyl-5-(3-pyridin-4-ylphenyl)-3,5-dihydro-4H-imidazol-4-one;

2-amino-5-(3-ethoxy-4-methoxyphenyl)-3-methyl-5-(3-pyridin-3-ylphenyl)-3,5-dihydro-4H-imidazol-4-one;

2-amino-3-methyl-5-(3-pyridin-3-ylphenyl)-5-[4-(trifluoromethoxy)phenyl]-3,5-dihydro-4H-imidazol-4-one;

2-amino-3-methyl-5-(3-pyridin-3-ylphenyl)-5-[(4-trifluoromethoxy-3-trifluoromethyl)phenyl]-3,5-dihydro-4H-imidazol-4-one;

2-amino-5-(3,4-diethoxyphenyl)-5-(4-fluoro-3-pyridin-3-ylphenyl)-3-methyl-3,5-dihydro-4H-imidazol-4-one;

2-amino-5-(3-chloro-4-trifluoromethoxyphenyl)-5-(4-fluoro-3-pyridin-3-ylphenyl)-3-methyl-3,5-dihydro-4H-imidazol-4-one;

a tautomer thereof; a stereoisomer thereof; and a pharmaceutically acceptable salt thereof.

18. A process for the preparation of a compound of formula I

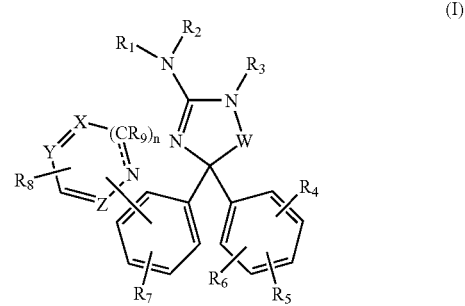

wherein W is CO;

X is N, NO or $CR_{10}$;

Y is N, NO or $CR_{11}$;

Z is N, NO or $CR_{19}$ with the proviso that no more than two of X, Y or Z may be N or NO;

$R_1$ and $R_2$ are each independently H, $COR_{20}$, $CO_2R_{21}$ or an optionally substituted $C_1$-$C_4$alkyl group;

$R_3$ is H, $OR_{12}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl($C_1$-$C_6$)alkyl group each optionally substituted;

$R_4$ and $R_5$ are each independently H, halogen, $NO_2$, CN, $OR_{13}$, $NR_{14}R_{15}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted or when attached to adjacent carbon atoms $R_4$ and $R_5$ may be taken together with the atoms to which they are attached to form an optionally substituted 5- to 7-membered ring optionally containing one or two heteroatoms selected from O, N or S;

$R_6$, $R_7$, $R_8$, $R_9$, $R_{10}$, $R_{11}$ and $R_{19}$ are each independently H, halogen, $NO_2$, CN, $OR_{16}$, $NR_{17}R_{18}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;

n is 0 or 1;

═ is a single bond when n is 0 or a double bond when n is 1;

$R_{12}$, $R_{13}$, $R_{16}$, $R_{20}$ and $R_{21}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each optionally substituted; and $R_{14}$, $R_{15}$, $R_{17}$ and $R_{18}$ are each independently H or $C_1$-$C_4$alkyl which process comprises reacting a compound of formula II

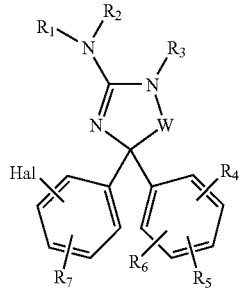

(II)

wherein Ha is Cl or Br and W, $R_1$, $R_2$, $R_3$, $R_4$, $R_5$, $R_6$ and $R_7$ are as described for formula I hereinabove with a compound of formula III

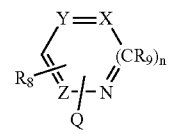

(III)

wherein Q is $B(OH)_2$, $Sn(n.Bu)_3$ or $Sn(CH_3)_3$ and X, Y, Z, $R_8$, $R_9$ and n are as described for formula I hereinabove in the presence of a palladium catalyst optionally in the presence of a solvent.

* * * * *